United States Patent
Biton et al.

(10) Patent No.: US 11,202,641 B2
(45) Date of Patent: Dec. 21, 2021

(54) ADJUSTABLE DRILLING DEVICE AND A METHOD FOR USE THEREOF

(71) Applicant: T.A.G. Medical Devices—Agriculture Cooperative Ltd., Kibbutz Gaaton (IL)

(72) Inventors: Dror Biton, Karmiel (IL); Ran Weisman, Kfar-Vradim (IL); Roy Zilberman, Qadarim (IL); Hagay Botansky, Haifa (IL); Hagay Sitry, Haifa (IL)

(73) Assignee: T.A.G. Medical Devices—Agriculture Cooperative Ltd., Kibbutz Gaaton (IL)

( * ) Notice: Subject to any disclaimer, the term of this patent is extended or adjusted under 35 U.S.C. 154(b) by 0 days.

(21) Appl. No.: 17/264,895

(22) PCT Filed: Aug. 1, 2019

(86) PCT No.: PCT/IL2019/050876
§ 371 (c)(1),
(2) Date: Feb. 1, 2021

(87) PCT Pub. No.: WO2020/026252
PCT Pub. Date: Feb. 6, 2020

(65) Prior Publication Data
US 2021/0298768 A1  Sep. 30, 2021

Related U.S. Application Data

(60) Provisional application No. 62/713,014, filed on Aug. 1, 2018.

(51) Int. Cl.
*A61B 17/16* (2006.01)
*A61B 17/00* (2006.01)

(52) U.S. Cl.
CPC .......... *A61B 17/1617* (2013.01); *A61B 17/16* (2013.01); *A61B 17/1637* (2013.01);
(Continued)

(58) Field of Classification Search
CPC .. A61B 17/1637; A61B 17/1617; A61B 17/16
See application file for complete search history.

(56) References Cited

U.S. PATENT DOCUMENTS

| | | | | |
|---|---|---|---|---|
| 854,956 A | * | 5/1907 | Martin | A61B 17/1617 606/80 |
| 1,006,468 A | | 10/1911 | Des Isles | |

(Continued)

FOREIGN PATENT DOCUMENTS

| CN | 1203518 | 12/1998 |
|---|---|---|
| CN | 2469895 | 1/2002 |

(Continued)

OTHER PUBLICATIONS

Relatorio de Busca e Parecer [Search Report and Opinion] dated Mar. 24, 2021 From the Servico Publico Federal, Ministerio da Economia, Instituto Nacional da Propriedade Industrial do Brasil, INPI Re. Application No. BR122020008361-1 and Its Translation Into English. (8 Pages).

(Continued)

*Primary Examiner* — Christian A Sevilla

(57) ABSTRACT

A bone removal device, including:
an elongated shaft having a longitudinal axis, a distal end and a proximal end;
a bone borer having a distal drilling tip configured to drill into a bone tissue and at least one proximal reamer, wherein the bone borer is movably coupled to a distal end of the elongated shaft, wherein the bone borer is configured to move between a drilling state in which the drilling tip is placed in contact with bone tissue, and reaming states in which the at least one proximal reamer is placed in contact with the bone tissue.

19 Claims, 46 Drawing Sheets

(52) U.S. Cl.
CPC .............. *A61B 2017/00367* (2013.01); *A61B 2017/00477* (2013.01)

(56) References Cited

U.S. PATENT DOCUMENTS

| | | | |
|---|---|---|---|
| 1,106,767 A | 8/1914 | Young | |
| 1,173,882 A | 2/1916 | Smith | |
| 1,204,330 A | 11/1916 | Adair | |
| 1,237,142 A | 8/1917 | Aase | |
| 1,958,399 A | 5/1934 | Stephens | |
| 3,540,324 A | 11/1970 | Johansson | |
| 3,690,357 A | 9/1972 | Lugo | |
| 3,702,611 A | 11/1972 | Fishbein | |
| 3,945,076 A | 3/1976 | Sung | |
| 4,541,423 A | 9/1985 | Barber | |
| 4,635,737 A | 1/1987 | Miyanaga | |
| 4,710,070 A | 12/1987 | Alsen et al. | |
| 4,738,255 A | 4/1988 | Goble et al. | |
| 4,883,048 A | 11/1989 | Purnell et al. | |
| 4,920,958 A | 5/1990 | Walt et al. | |
| 4,992,010 A | 2/1991 | Fischer | |
| 4,998,981 A | 3/1991 | Miyanaga | |
| 5,112,337 A | 5/1992 | Paulos et al. | |
| 5,330,468 A | 6/1994 | Burkhart | |
| 5,507,606 A | 4/1996 | Steiner | |
| 5,643,273 A | 7/1997 | Clark | |
| 5,645,589 A | 7/1997 | Li | |
| 5,681,320 A | 10/1997 | McGuire | |
| 5,817,095 A | 10/1998 | Smith | |
| 5,839,860 A | 11/1998 | Steiner | |
| 6,015,411 A | 1/2000 | Ohkoshi et al. | |
| 6,120,511 A | 9/2000 | Chan | |
| 6,162,227 A * | 12/2000 | Eckhardt | A61B 17/1668 407/30 |
| 6,210,415 B1 | 4/2001 | Bester | |
| 6,358,251 B1 | 3/2002 | Mirza | |
| 6,383,188 B2 | 5/2002 | Kuslich et al. | |
| 6,679,886 B2 | 1/2004 | Weikel et al. | |
| 6,746,451 B2 | 6/2004 | Middleton et al. | |
| 6,780,175 B1 | 8/2004 | Sachdeva et al. | |
| 6,923,813 B2 | 8/2005 | Phillips et al. | |
| 7,097,648 B1 | 8/2006 | Globerman et al. | |
| 7,172,374 B2 | 2/2007 | Burr et al. | |
| 7,179,024 B2 | 2/2007 | Greenhalgh | |
| 7,637,910 B2 | 12/2009 | Schmieding et al. | |
| 7,682,378 B2 | 3/2010 | Truckai et al. | |
| 7,914,545 B2 | 3/2011 | Ek | |
| 7,927,332 B2 | 4/2011 | Huebner et al. | |
| 7,938,835 B2 | 5/2011 | Boucher et al. | |
| RE42,757 E | 9/2011 | Kuslich et al. | |
| 8,038,678 B2 * | 10/2011 | Schmieding | A61B 17/1675 606/80 |
| 8,038,679 B2 | 10/2011 | Wieland | |
| 8,048,079 B2 * | 11/2011 | Iannarone | A61B 17/1675 606/80 |
| 8,388,621 B2 | 3/2013 | Bourque et al. | |
| 9,198,676 B2 | 12/2015 | Pilgeram et al. | |
| 9,381,021 B2 | 7/2016 | Wagner et al. | |
| 9,795,395 B2 | 10/2017 | Lizardi et al. | |
| 9,950,445 B2 | 4/2018 | Miyanaga | |
| 10,405,872 B2 * | 9/2019 | Victor | A61B 17/164 |
| 2002/0165550 A1 | 11/2002 | Frey et al. | |
| 2002/0183758 A1 * | 12/2002 | Middleton | A61B 17/1664 606/79 |
| 2002/0193799 A1 | 12/2002 | Chappuis et al. | |
| 2004/0126196 A1 | 7/2004 | Burr et al. | |
| 2004/0208717 A1 | 10/2004 | Greenhalgh | |
| 2004/0254585 A1 | 12/2004 | Whittaker et al. | |
| 2005/0113836 A1 | 5/2005 | Lozier et al. | |
| 2005/0131345 A1 | 6/2005 | Miller | |
| 2005/0240193 A1 | 10/2005 | Layne et al. | |
| 2006/0025774 A1 | 2/2006 | Fishbein et al. | |
| 2006/0149268 A1 | 7/2006 | Truckai et al. | |
| 2006/0195112 A1 | 8/2006 | Ek | |
| 2006/0241629 A1 | 10/2006 | Krebs et al. | |
| 2006/0264957 A1 | 11/2006 | Cragg et al. | |
| 2007/0123889 A1 * | 5/2007 | Malandain | A61B 17/320016 606/79 |
| 2007/0276392 A1 | 11/2007 | Beyar et al. | |
| 2007/0282345 A1 | 12/2007 | Yedlicka et al. | |
| 2008/0103506 A1 | 5/2008 | Volpi et al. | |
| 2008/0114364 A1 | 5/2008 | Goldin et al. | |
| 2008/0154271 A1 | 6/2008 | Berberich et al. | |
| 2008/0183174 A1 | 7/2008 | Sikora et al. | |
| 2009/0018468 A1 | 1/2009 | Janssens | |
| 2009/0254092 A1 * | 10/2009 | Albiol Llorach | A61B 17/1617 606/87 |
| 2010/0168747 A1 | 7/2010 | Lynch et al. | |
| 2010/0241124 A1 | 9/2010 | Housman et al. | |
| 2010/0249785 A1 | 9/2010 | Betts | |
| 2010/0268234 A1 | 10/2010 | Aho et al. | |
| 2011/0087257 A1 | 4/2011 | To et al. | |
| 2011/0098709 A1 | 4/2011 | Malandain et al. | |
| 2011/0130760 A1 | 6/2011 | Anderson et al. | |
| 2011/0164937 A1 * | 7/2011 | Byrne | B23B 51/08 408/200 |
| 2011/0166575 A1 | 7/2011 | Assell et al. | |
| 2011/0166581 A1 | 7/2011 | Van Der Merwe et al. | |
| 2011/0190832 A1 | 8/2011 | Taylor et al. | |
| 2011/0251616 A1 | 10/2011 | Osman et al. | |
| 2012/0022568 A1 | 1/2012 | Koblish et al. | |
| 2012/0059382 A1 | 3/2012 | Paulos | |
| 2012/0209274 A1 | 8/2012 | Belaney et al. | |
| 2012/0239072 A1 | 9/2012 | Rodriguez | |
| 2012/0245585 A1 | 9/2012 | Kaiser et al. | |
| 2013/0030442 A1 | 1/2013 | Pilgeram et al. | |
| 2013/0150859 A1 | 6/2013 | Kehres et al. | |
| 2013/0165935 A1 | 6/2013 | Griffiths et al. | |
| 2014/0039552 A1 | 2/2014 | Pilgeram | |
| 2014/0194880 A1 | 7/2014 | Schmieding et al. | |
| 2014/0257297 A1 | 9/2014 | Koogle, Jr. et al. | |
| 2014/0276844 A1 | 9/2014 | Bourque et al. | |
| 2014/0316413 A1 | 10/2014 | Burger et al. | |
| 2014/0324052 A1 | 10/2014 | Garrison et al. | |
| 2015/0073417 A1 | 3/2015 | Norton et al. | |
| 2015/0150570 A1 | 6/2015 | Okuno et al. | |
| 2015/0265287 A1 | 9/2015 | Berberich | |
| 2016/0038157 A1 | 2/2016 | Mirochnik et al. | |
| 2017/0128086 A1 | 5/2017 | Slobitker et al. | |
| 2017/0224359 A1 | 8/2017 | Mirochnik et al. | |
| 2017/0245869 A1 | 8/2017 | Mirochnik et al. | |
| 2018/0360467 A1 | 12/2018 | Slobitker et al. | |
| 2019/0059910 A1 | 2/2019 | Adams et al. | |
| 2019/0167281 A1 | 6/2019 | Zilberman et al. | |
| 2019/0388102 A1 | 12/2019 | Slobitker et al. | |
| 2020/0163684 A1 | 5/2020 | Mirochnik et al. | |
| 2020/0246023 A1 * | 8/2020 | Forsell | A61B 17/1666 |
| 2020/0275939 A1 | 9/2020 | Slobitker et al. | |
| 2020/0405327 A1 | 12/2020 | Zilberman et al. | |

FOREIGN PATENT DOCUMENTS

| | | |
|---|---|---|
| CN | 1925798 | 3/2007 |
| CN | 201394046 | 2/2010 |
| CN | 101677823 | 3/2010 |
| CN | 101795629 | 8/2010 |
| CN | 201617897 | 11/2010 |
| EP | 1535579 | 1/2005 |
| EP | 1785103 | 5/2007 |
| ES | 2351563 | 2/2011 |
| JP | 2003-531676 | 10/2003 |
| JP | 2006-523542 | 10/2006 |
| JP | 2008-521511 | 6/2008 |
| JP | 2009-533159 | 9/2009 |
| JP | S48-62067 | 1/2012 |
| JP | 2012-522604 | 9/2012 |
| JP | 2012-187384 | 10/2012 |
| JP | 2013-516275 | 5/2013 |
| JP | 2016-516524 | 6/2016 |
| WO | WO 01/58629 | 8/2001 |
| WO | WO 01/82838 | 11/2001 |
| WO | WO 2006/060420 | 6/2006 |
| WO | WO 2007/120903 | 10/2007 |
| WO | WO 2010/065047 | 6/2010 |

(56) References Cited

FOREIGN PATENT DOCUMENTS

| WO | WO 2010/115134 | 10/2010 |
|---|---|---|
| WO | WO 2013/192080 | 12/2013 |
| WO | WO 2014/089198 | 6/2014 |
| WO | WO 2014/174521 | 10/2014 |
| WO | WO 2016/063279 | 4/2016 |
| WO | WO 2016/162869 | 10/2016 |
| WO | WO 2017/137998 | 8/2017 |
| WO | WO 2017/187436 | 11/2017 |
| WO | WO 2018/051356 | 3/2018 |
| WO | WO 2020/026252 | 2/2020 |

OTHER PUBLICATIONS

Advisory Action Before the Filing of An Appeal Brief dated Apr. 1, 2019 From the US Patent and Trademark Office Re. U.S. Appl. No. 15/318,677. (8 pages).
Advisory Action Before the Filing of An Appeal Brief dated Feb. 28, 2018 From the US Patent and Trademark Office Re. U.S. Appl. No. 15/498,731. (3 pages).
Applicant-Initiated Interview Summary dated Jul. 18, 2018 From the US Patent and Trademark Office Re. U.S. Appl. No. 15/498,731. (4 pages).
Applicant-Initiated Interview Summary dated Feb. 26, 2019 From the US Patent and Trademark Office Re. U.S. Appl. No. 15/318,677. (3 pages).
Communication Pursuant to Article 94(3) EPC dated Mar. 1, 2018 From the European Patent Office Re. Application No. 15804626.8. (3 Pages).
Communication Pursuant to Article 94(3) EPC dated Jun. 8, 2018 From the European Patent Office Re. Application No. 17205443.9. (5 Pages).
Communication Pursuant to Article 94(3) EPC dated Mar. 16, 2021 From the European Patent Office Re. Application No. 17205443.9. (6 Pages).
Communication Relating to the Results of the Partial International Search dated May 19, 2016 From the International Searching Authority Re. Application No. PCT/IL2015/051033.
European Search Report and the European Search Opinion dated Mar. 2, 2021 From the European Patent Office Re. Application No. 20209453.8. (5 Pages).
European Search Report dated Apr. 30, 2018 From the European Patent Office Re. Application No. 17205443.9. (5 Pages).
Examination Report dated Jan. 15, 2020 From the Servico Publico Federal, Ministerio da Economia, Instituto Nacional da Propriedade Industrial do Brasil Re. Application No. BR112015026975-3 and Its Summary in English. (4 Pages).
Examination Report Under Sections 12 & 13 of the Patents Act, 1970 and the Patents Rules, 2003 dated Mar. 5, 2021 From the Government of India, Intellectual Property India, Patents, Designs, Trade Marks, Geographical Indications, The Patent Office Re. Application No. 201727016824. (7 Pages).
Examination Report Under Sections 12 & 13 of the Patents Act, 1970 and the Patents Rules, 2003 dated Sep. 28, 2020 From the Government of India, Intellectual Property Indis, Patents, Designs, Trade Marks, Geographical Indications, The Patent Office Re. Application No. 2954/MUMNP/2015. (7 Pages).
Final Office Action dated May 11, 2021 From the Japan Patent Office Re. Application No. 2018-241087 and Its Translation Into English. (4 Pages).
International Preliminary Report on Patentability dated May 4, 2017 From the International Bureau of WIPO Re. Application No. PCT/IL2015/051033. (11 Pages).
International Preliminary Report on Patentability dated Nov. 5, 2015 From the International Bureau of WIPO Re. Application No. PCT/IL2014/050381.
International Preliminary Report on Patentability dated Feb. 11, 2021 From the International Bureau of WIPO Re. Application No. PCT/IL2019/050876. (11 Pages).
International Preliminary Report on Patentability dated Oct. 19, 2017 From the International Bureau of WIPO Re. Application No. PCT/IL2016/050370. (12 Pages).
International Preliminary Report on Patentability dated Aug. 23, 2018 From the International Bureau of WIPO Re. Application No. PCT/IL2017/050170. (16 Pages).
International Search Report and the Written Opinion dated Aug. 4, 2016 From the International Searching Authority Re. Application No. PCT/IL2015/051033.
International Search Report and the Written Opinion dated Oct. 7, 2016 From the International Searching Authority Re. Application No. PCT/IL2016/050370.
International Search Report and the Written Opinion dated Sep. 10, 2014 From the International Searching Authority Re. Application No. PCT/IL2014/050381.
International Search Report and the Written Opinion dated Aug. 11, 2017 From the International Searching Authority Re. Application No. PCT/IL2017/050170. (24 Pages).
International Search Report and the Written Opinion dated Jan. 22, 2020 From the International Searching Authority Re. Application No. PCT/IL2019/050876. (19 Pages).
International Search Report and the Written Opinion dated Aug. 29, 2017 From the International Searching Authority Re. Application No. PCT/IL2017/050469. (17 Pages).
Interview Summary dated Dec. 11, 2020 from the US Patent and Trademark Office Re. U.S. Appl. No. 16/090,820. (2 pages).
Invitation to Pay Additional Fees dated Aug. 1, 2016 From the International Searching Authority Re. Application No. PCT/IL2016/050370.
Invitation to Pay Additional Fees dated Nov. 13, 2019 From the International Searching Authority Re. Application No. PCT/IL2019/050876. (3 Pages).
Invitation to Pay Additional Fees dated May 17, 2017 From the International Searching Authority Re. Application No. PCT/IL2017/050170. (2 Pages).
Notice Of Allowance dated Jan. 16, 2020 From the US Patent and Trademark Office Re. U.S. Appl. No. 16/059,098. (23 pages).
Notice of Allowance dated Feb. 18, 2021 From the US Patent and Trademark Office Re. U.S. Appl. No. 16/740,597. (44 Pages).
Notice of Allowance dated Oct. 22, 2020 From the US Patent and Trademark Office Re. U.S. Appl. No. 16/090,820. (12 Pages).
Notice of Decision of Rejection dated Sep. 4, 2018 From the Japan Patent Office Re. Application No. 2016-509605. (4 Pages).
Notice of Reason for Rejection dated Feb. 27, 2018 From the Japan Patent Office Re. Application No. 2016-509605. (2 Pages).
Notice of Reasons for Rejection dated Dec. 1, 2020 From the Japan Patent Office Re. Application No. 2017-552067 and Its Translation Into English. (9 Pages).
Notice of Reasons for Rejection dated Jul. 7, 2020 From the Japan Patent Office Re. Application No. 2017-521086. (3 Pages).
Notice of Reasons for Rejection dated Dec. 8, 2020 From the Japan Patent Office Re. Application No. 2018-241087. (4 Pages).
Notice of Reasons for Rejection dated Dec. 10, 2019 From the Japan Patent Office Re. Application No. 2017-521086. (7 Pages).
Notice of Reasons for Rejection dated Mar. 10, 2020 From the Japan Patent Office Re. Application No. 2018-241087 and Its Translation Into English. (13 Pages.
Notice of Reasons for Rejection dated Feb. 18, 2020 From the Japan Patent Office Re. Application No. 2017-552067 and Its Translation Into English. (18 Pages).
Notice of Reasons for Rejection dated Aug. 20, 2019 From the Japan Patent Office Re. Application No. 2017-521086. (7 Pages).
Notice of Reasons for Rejection dated Jan. 21, 2020 From the Japan Patent Office Re. Application No. 2016-509605. (3 Pages).
Notification of Office Action and Search Report dated Aug. 1, 2019 From the State Intellectual Property Office of the People's Republic of China Re. Application No. 201680027825.X. (7 Pages).
Notification of Office Action and Search Report dated Jun. 1, 2020 From the State Intellectual Property Office of the People's Republic of China Re. Application No. 201810460549.7. (8 Pages).
Notification of Office Action and Search Report dated May 6, 2020 From the State Intellectual Property Office of the People's Republic of China Re. Application No. 201680027825.X. (6 Pages).

(56) References Cited

OTHER PUBLICATIONS

Notification of Office Action and Search Report dated Jul. 9, 2019 From the State Intellectual Property Office of the People's Republic of China Re. Application No. 201580069380.7. (5 Pages).
Notification of Office Action and Search Report dated Nov. 10, 2020 From the State Intellectual Property Office of the People's Republic of China Re. Application No. 201680027825.X. (4 Pages).
Notification of Office Action and Search Report dated Aug. 15, 2017 From the State Intellectual Property Office of the People's Republic of China Re. Application No. 201480035299.2. (6 Pages).
Notification of Office Action dated Dec. 4, 2018 From the State Intellectual Property Office of the People's Republic of China Re. Application No. 201580069380.7 and Its Translation Into English. (4 Pages).
Notification of Office Action dated Nov. 30, 2020 From the State Intellectual Property Office of the People's Republic of China Re. Application No. 201810460549.7. (5 Pages).
Official Action dated Nov. 2, 2016 From the US Patent and Trademark Office Re. U.S. Appl. No. 14/919,921.
Official Action dated Nov. 8, 2017 From the US Patent and Trademark Office Re. U.S. Appl. No. 15/318,677. (17 pages).
Official Action dated Dec. 13, 2017 From the US Patent and Trademark Office Re. U.S. Appl. No. 15/498,731. (12 pages).
Official Action dated Jul. 17, 2017 From the US Patent and Trademark Office Re. U.S. Appl. No. 15/498,731. (13 Pages).
Official Action dated Apr. 18, 2017 From the US Patent and Trademark Office Re. U.S. Appl. No. 15/318,677. (21 pages).
Official Action dated Jan. 23, 2019 From the US Patent and Trademark Office Re. U.S. Appl. No. 15/318,677. (16 pages).
Official Action dated May 24, 2019 From the US Patent and Trademark Office Re. U.S. Appl. No. 15/519,844. (28 pages).
Official Action dated Mar. 27, 2018 From the US Patent and Trademark Office Re. U.S. Appl. No. 15/318,677. (15 pages).
Official Action dated Aug. 29, 2018 From the US Patent and Trademark Office Re. U.S. Appl. No. 15/318,677. (17 pages).
Official Action dated Mar. 29, 2018From the US Patent and Trademark Office Re. U.S. Appl. No. 15/498,731. (15 pages).
Restriction Official Action dated Jul. 8, 2016 From the US Patent and Trademark Office Re. U.S. Appl. No. 14/919,921.
Restriction Official Action dated Feb. 11, 2016 From the US Patent and Trademark Office Re. U.S. Appl. No. 14/919,921.
Restriction Official Action dated Jul. 2, 2020 from the US Patent and Trademark Office Re. U.S. Appl. No. 16/090,820. (7 pages).
Search Report and Explanation dated Apr. 16, 2020 From the Servico Publico Federal, Ministerio da Economia, Instituto Nacional da Propriedade Industrial do Brasil Re. Application No. BR112017008135-0 and Its Summary in English. (5 Pages).
Supplementary European Search Report and the European Search Opinion dated Apr. 6, 2020 From the European Patent Office Re. Application No. 17788940.9. (5 Pages).
Supplementary European Search Report and the European Search Opinion dated Dec. 13, 2018 From the European Patent Office Re. Application No. 16776225.1. (8 Pages).
Supplementary European Search Report and the European Search Opinion dated Jan. 30, 2019 From the European Patent Office Re. Application No. 17749987.8. (6 Pages).
Translation Dated Jun. 4, 2020 of Notification of Office Action dated May 6, 2020 From the State Intellectual Property Office of the People's Republic of China Re. Application No. 201680027825.X. (4 Pages).
Translation Dated Sep. 4, 2019 of Notice of Reasons for Rejection dated Aug. 20, 2019 From the Japan Patent Office Re. Application No. 2017-521086. (7 Pages).
Translation Dated Oct. 5, 2018 of Notice of Decision of Rejection dated Sep. 4, 2018 From the Japan Patent Office Re. Application No. 2016-509605. (4 Pages).
Translation Dated Feb. 7, 2020 of Notice of Reasons for Rejection dated Jan. 21, 2020 From the Japan Patent Office Re. Application No. 2016-509605. (3 Pages).
Translation Dated Dec. 9, 2020 of Notification of Office Action dated Nov. 30, 2020 From the State Intellectual Property Office of the People's Republic of China Re. Application No. 201810460549.7. (6 Pages).
Translation Dated Jan. 9, 2020 of Notice of Reasons for Rejection dated Dec. 10, 2019 From the Japan Patent Office Re. Application No. 2017-521086. (8 Pages).
Translation Dated Jul. 14, 2019 of Notification of Office Action dated Jul. 9, 2019 From the State Intellectual Property Office of the People's Republic of China Re. Application No. 201580069380.7. (1 Page).
Translation Dated Jun. 22, 2020 of Notification of Office Action dated Jun. 1, 2020 From the State Intellectual Property Office of the People's Republic of China Re. Application No. 201810460549.7. (4 Pages).
Translation Dated Mar. 22, 2018 of Notice of Reason for Rejection dated Feb. 27, 2018 From the Japan Patent Office Re. Application No. 2016-509605. (2 Pages).
Translation Dated Aug. 23, 2019 of Notification of Office Action dated Aug. 1, 2019 From the State Intellectual Property Office of the People's Republic of China Re. Application No. 201680027825.X. (4 Pages).
Translation Dated Nov. 26, 2020 of Notification of Office Action dated Nov. 10, 2020 From the State Intellectual Property Office of the People's Republic of China Re. Application No. 201680027825.X, (3 Pages).
Translation Dated Dec. 30, 2020 of Notice of Reasons for Rejection dated Dec. 8, 2020 From the Japan Patent Office Re. Application No. 2018-241087. (4 Pages).
Translation of Notification of Office Action dated Aug. 15, 2017 From the State Intellectual Property Office of the People's Republic of China Re. Application No. 201480035299.2. (3 Pages).
Communication Pursuant to Article 94(3) EPC dated May 17, 2021 From the European Patent Office Re. Application No. 17788940.9. (6 Pages).

* cited by examiner

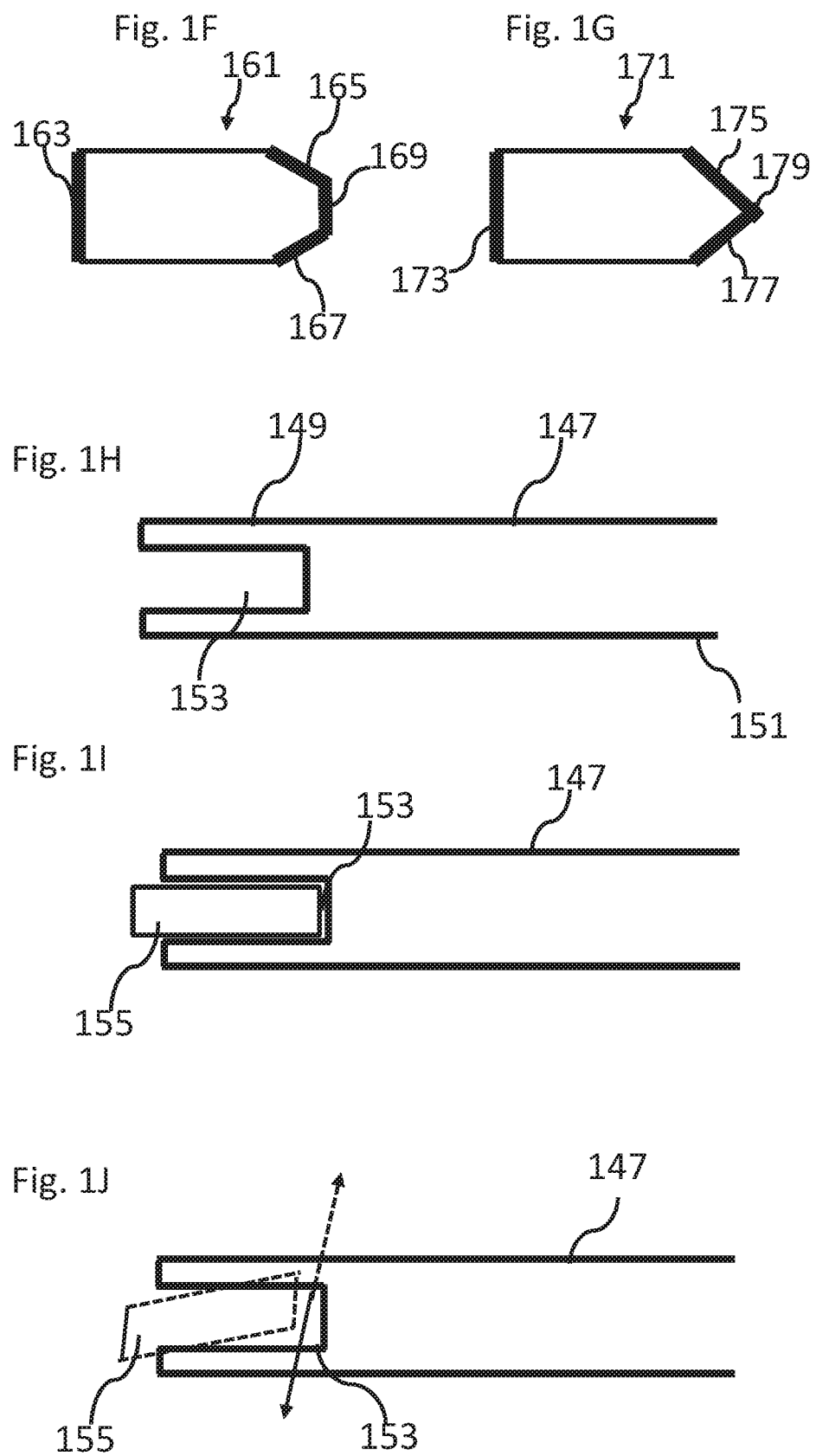

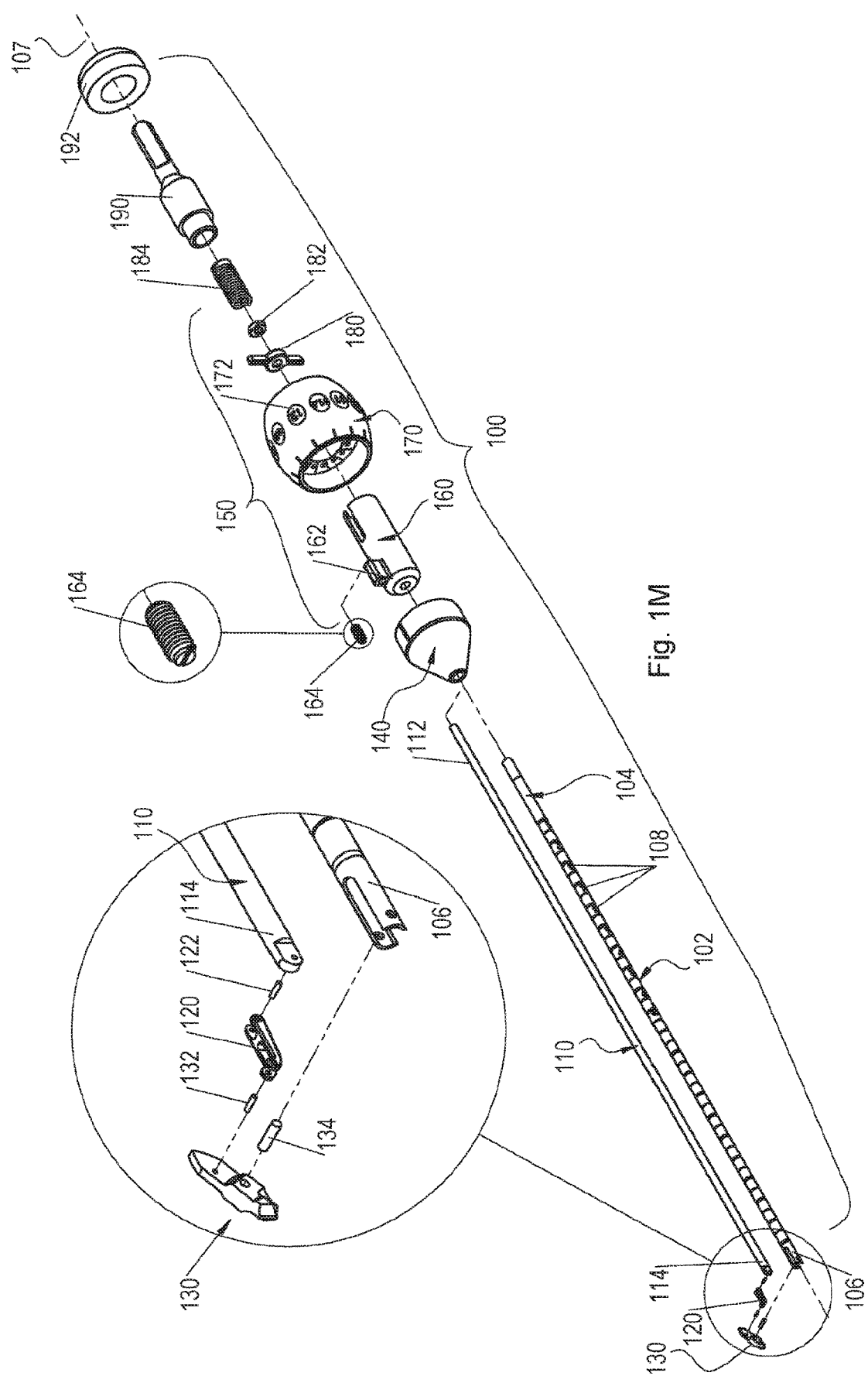

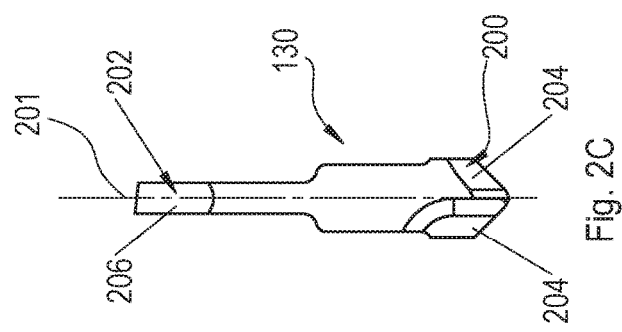
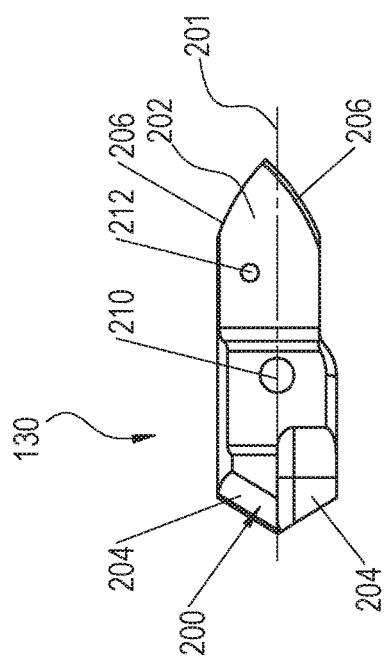
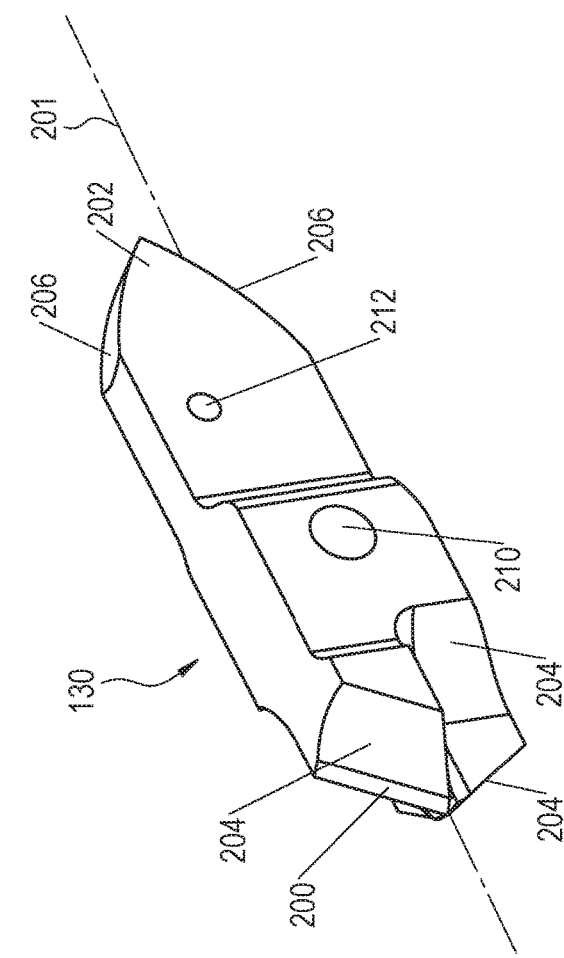

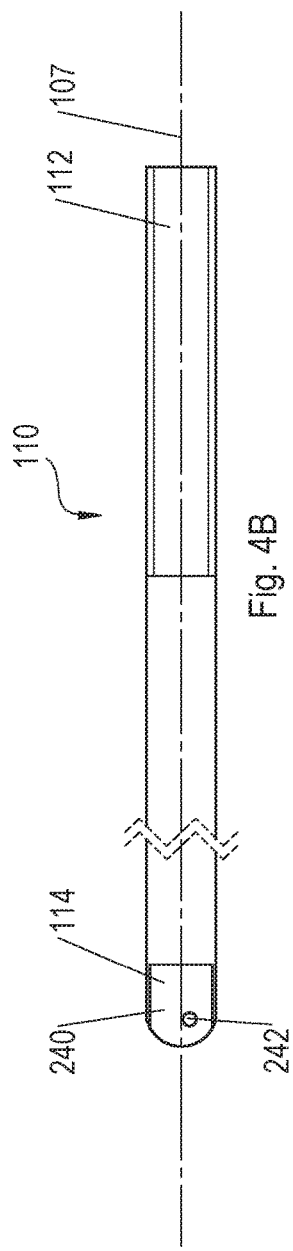
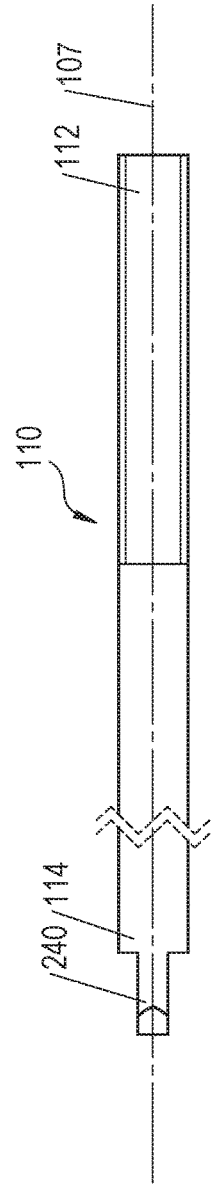
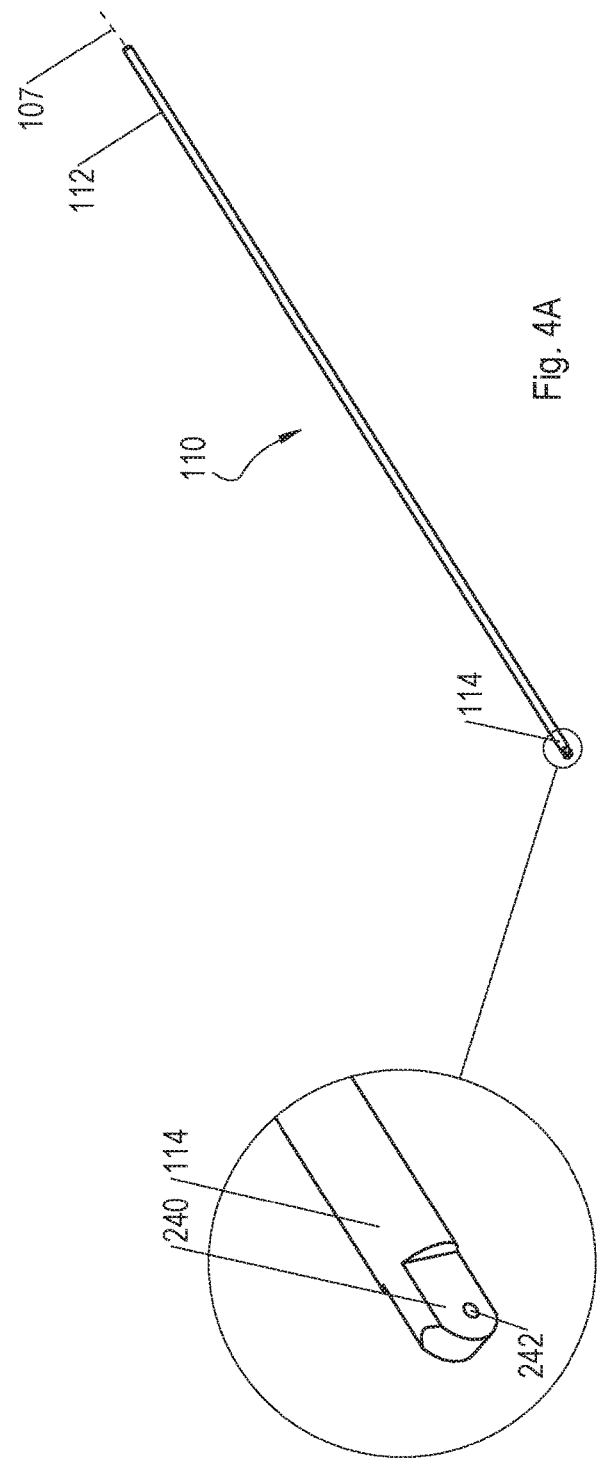

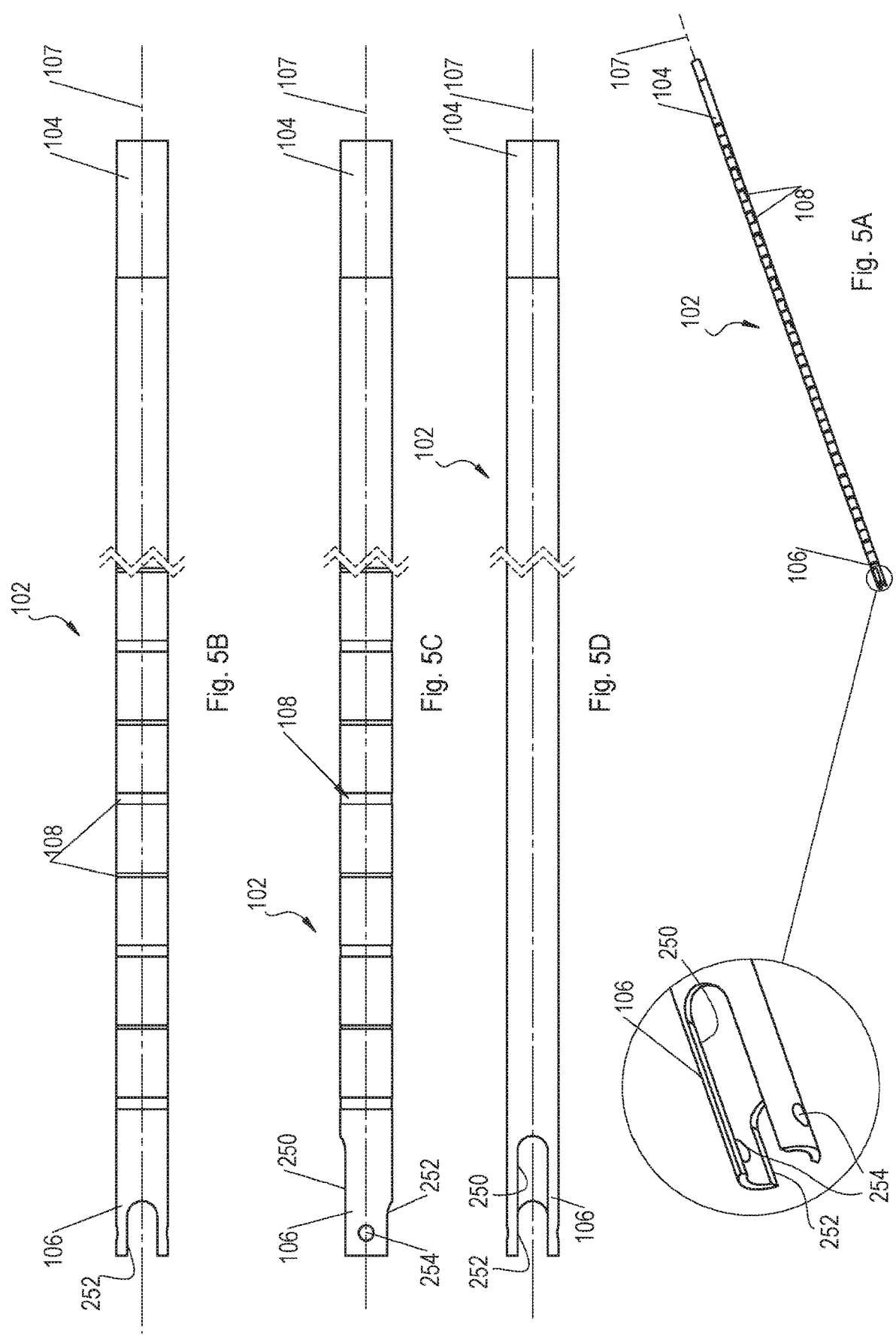

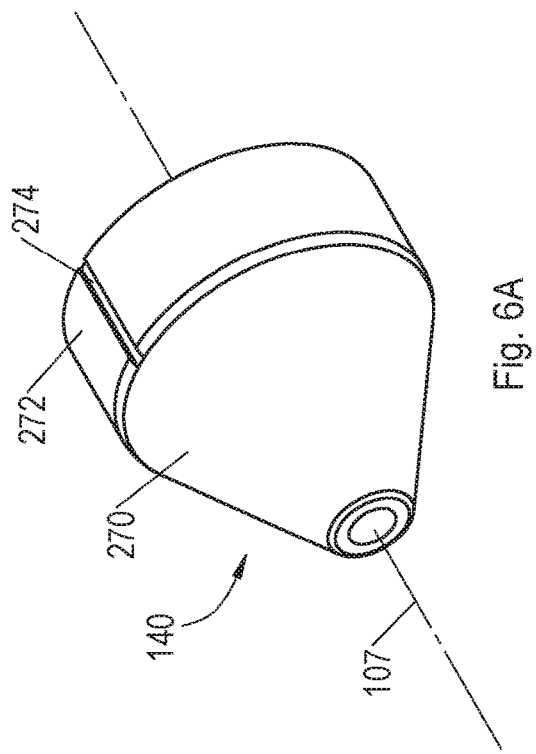
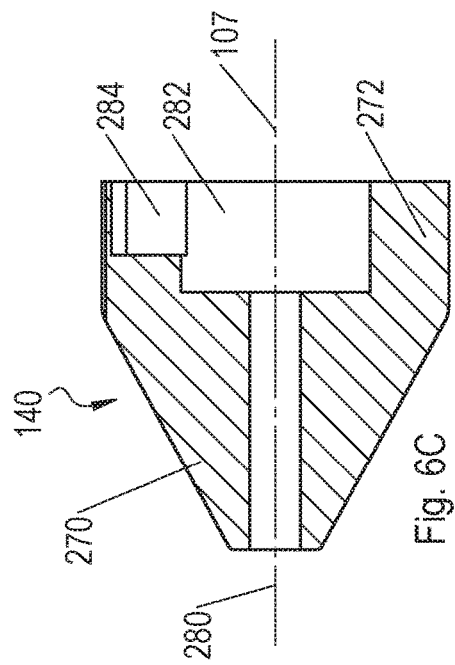
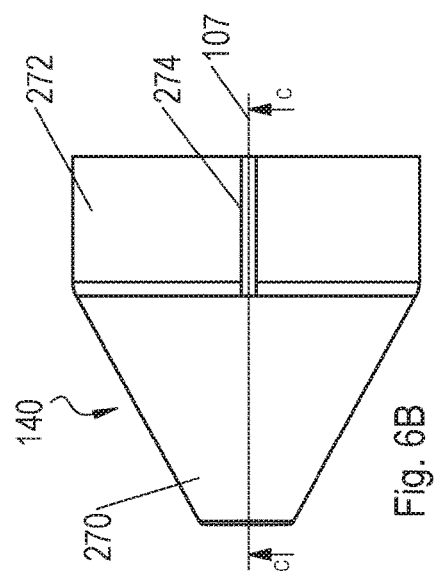

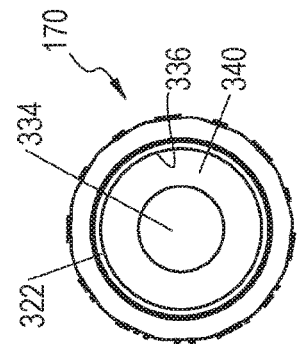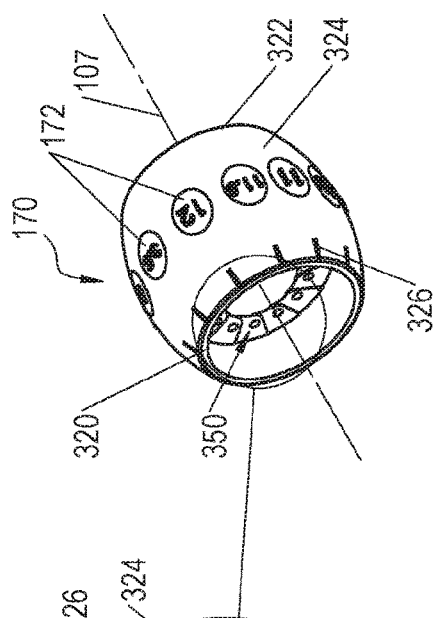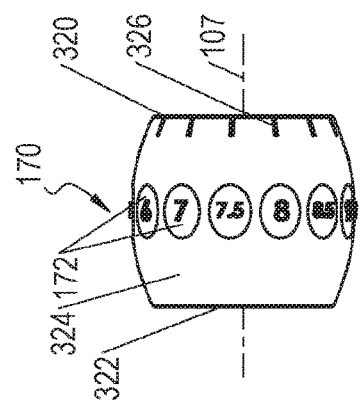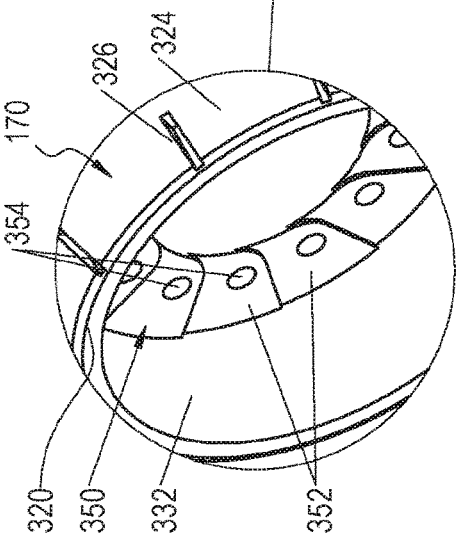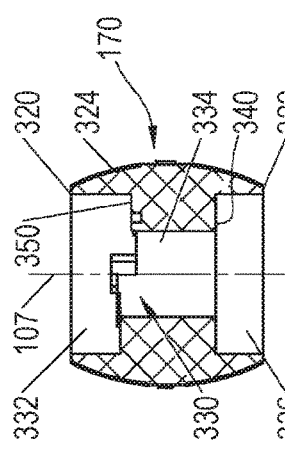

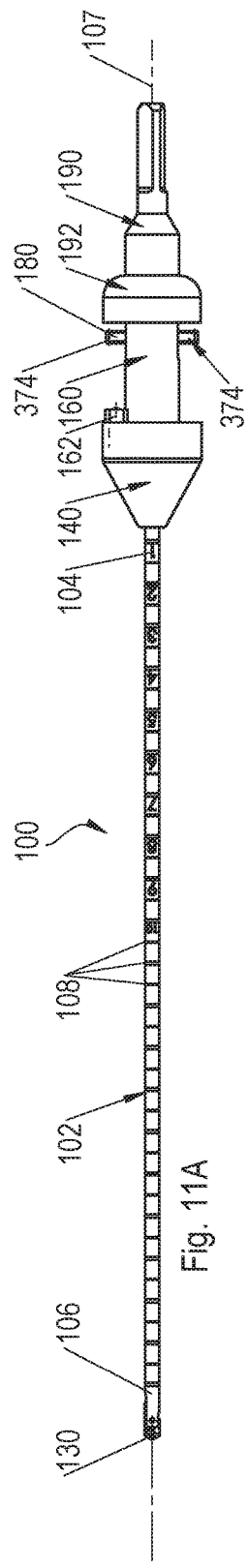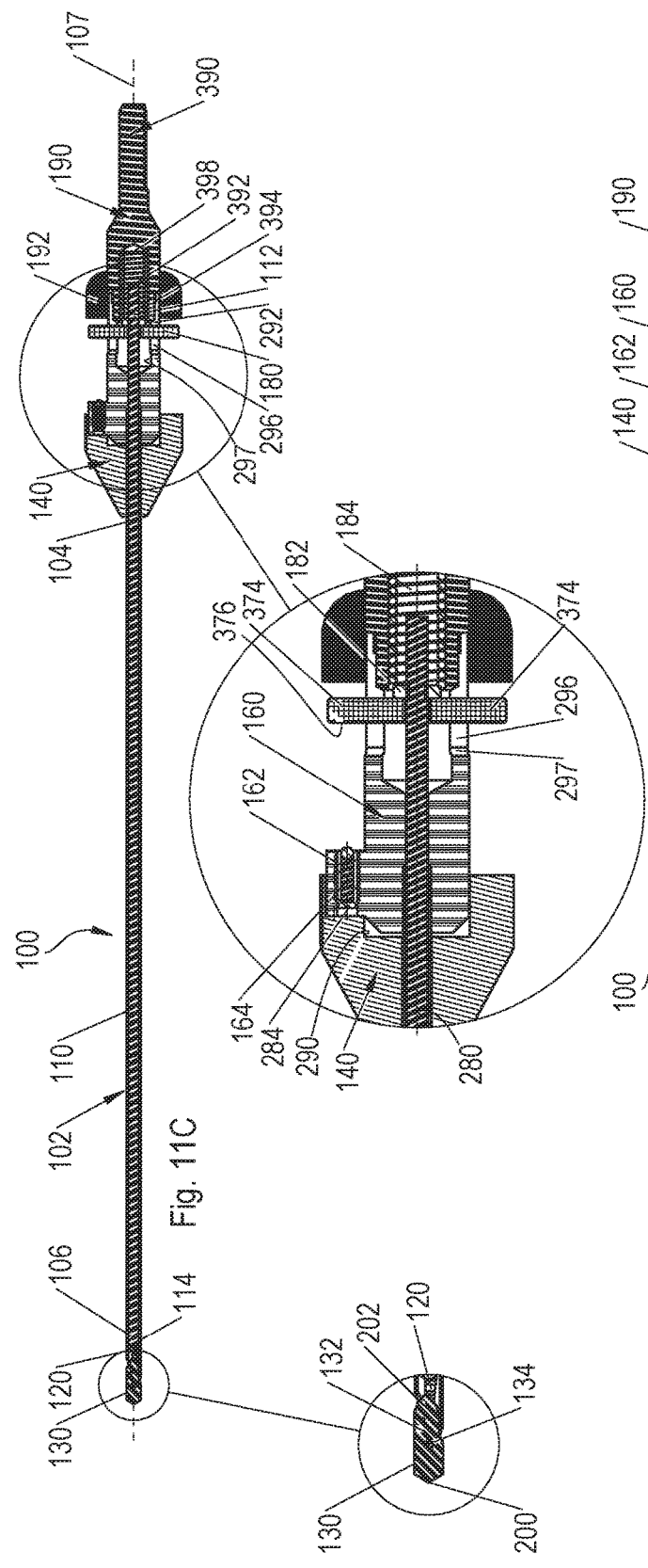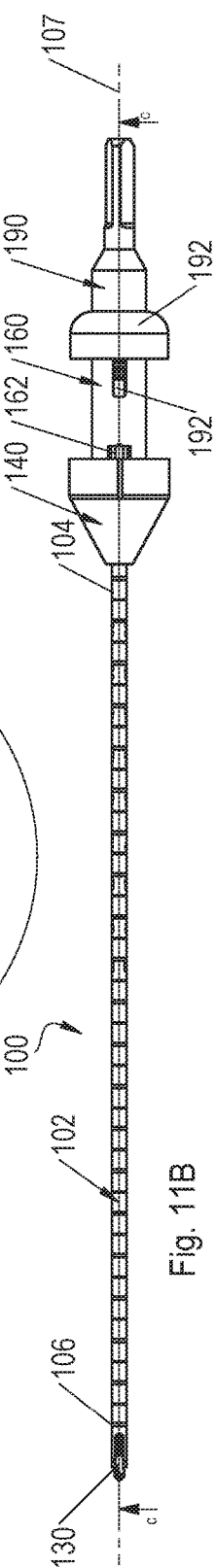

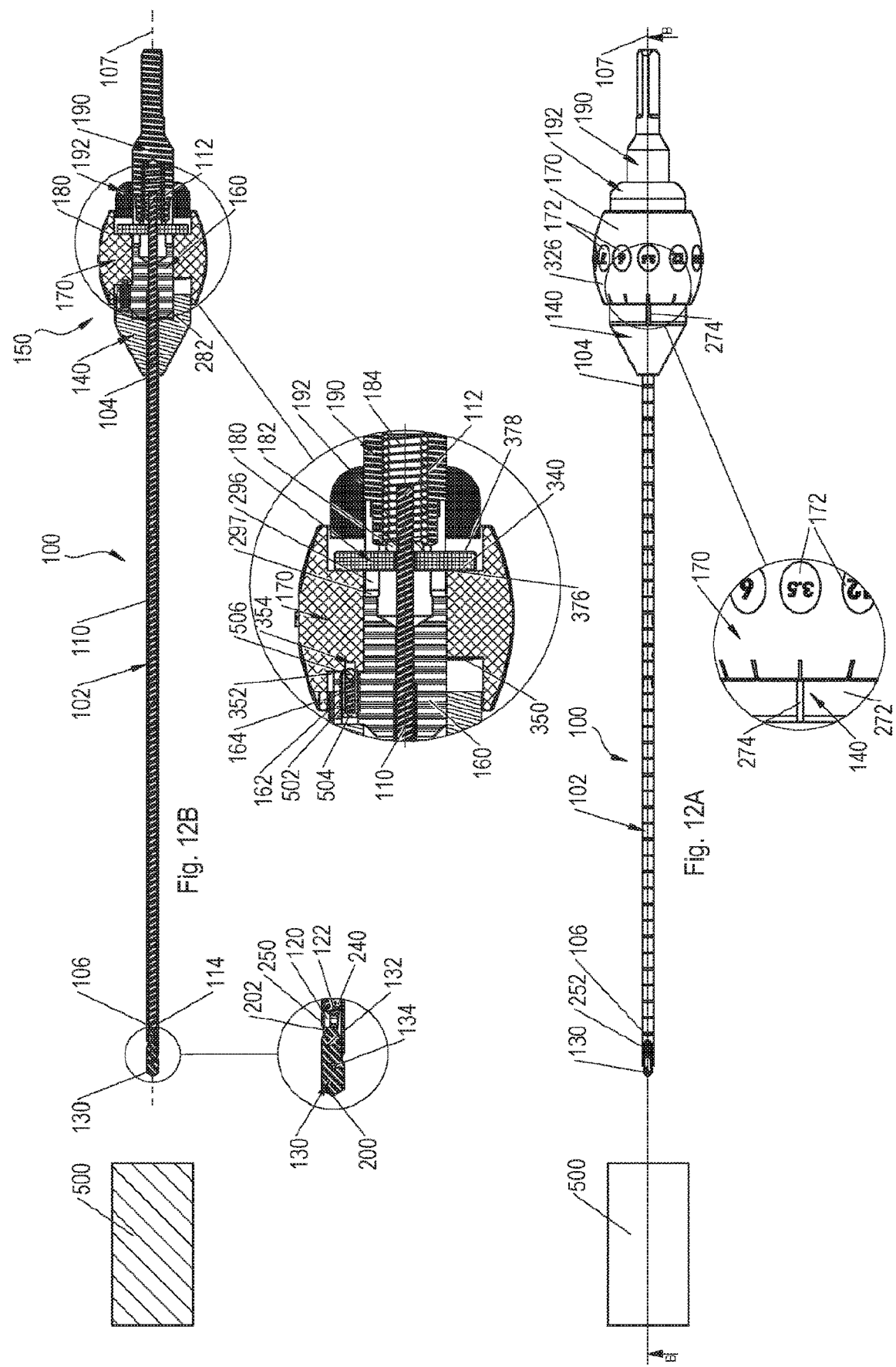

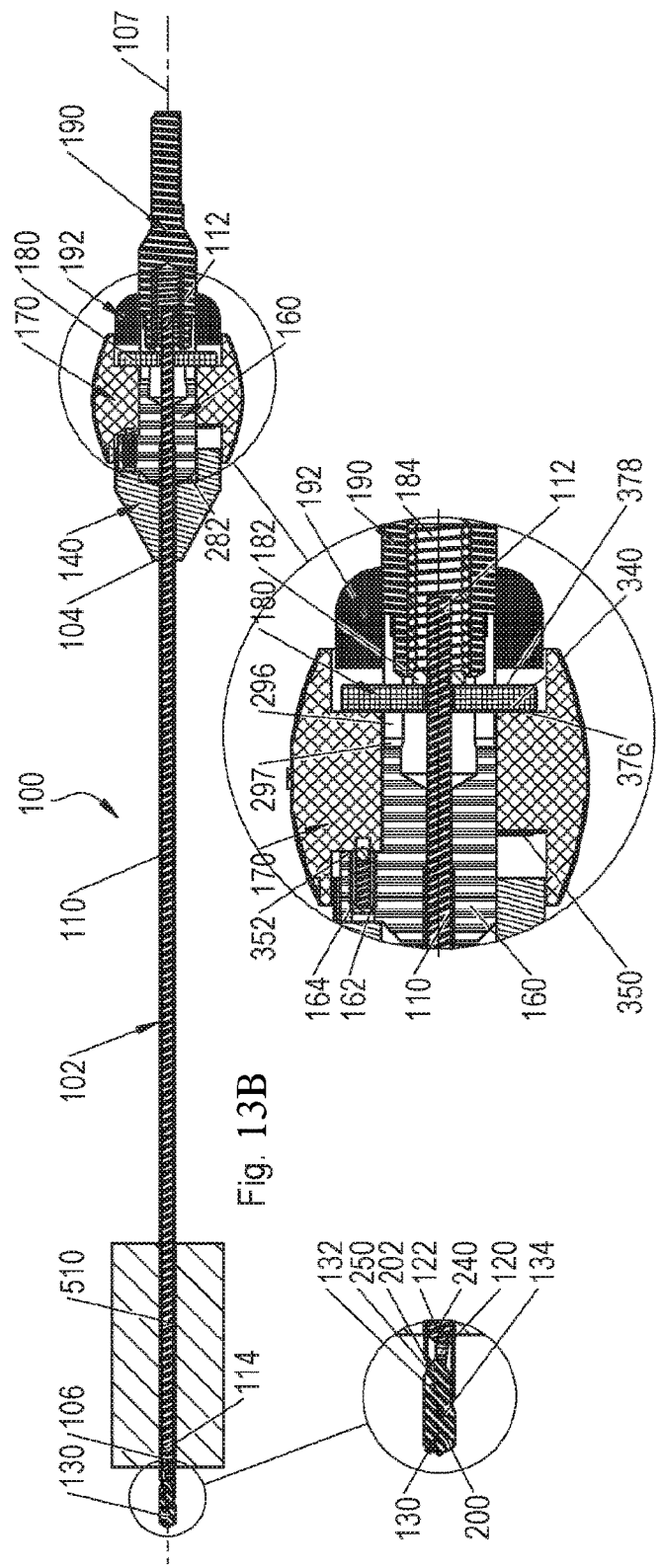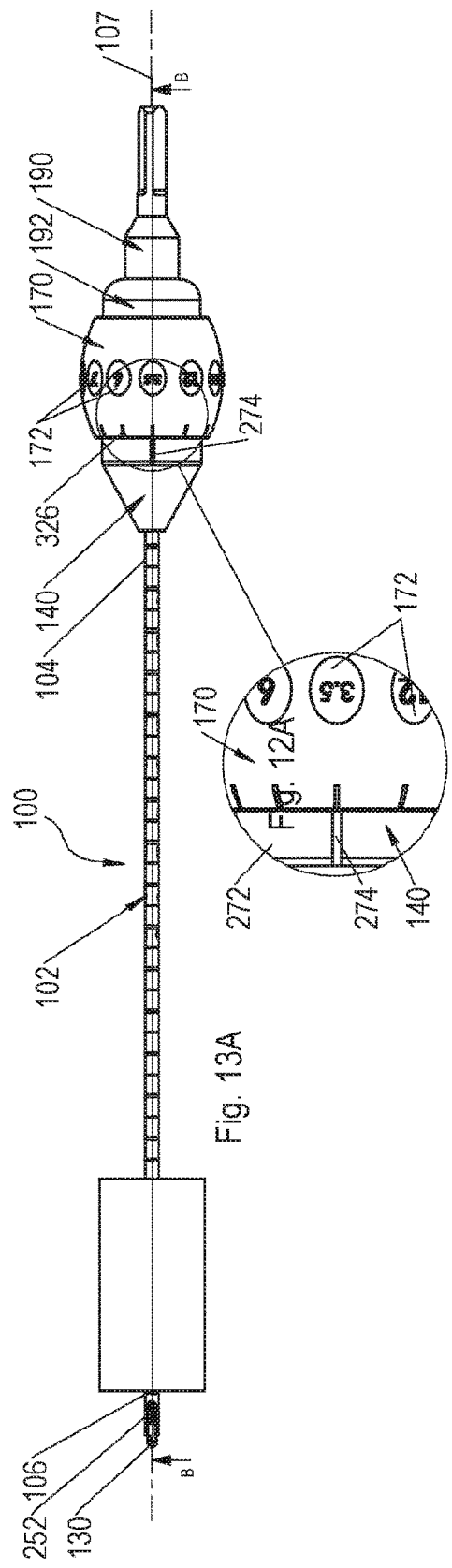
Fig. 13B
Fig. 13A

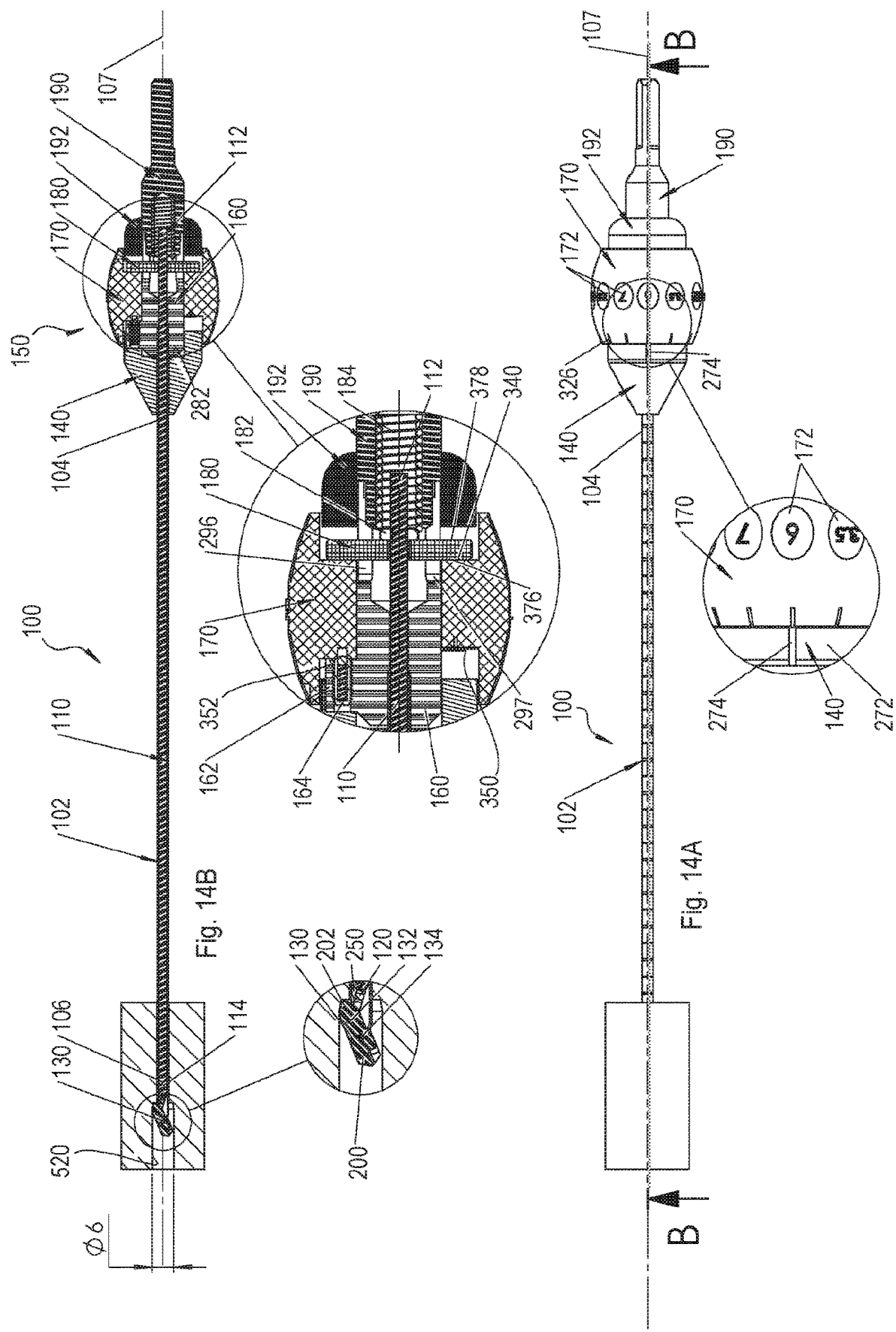

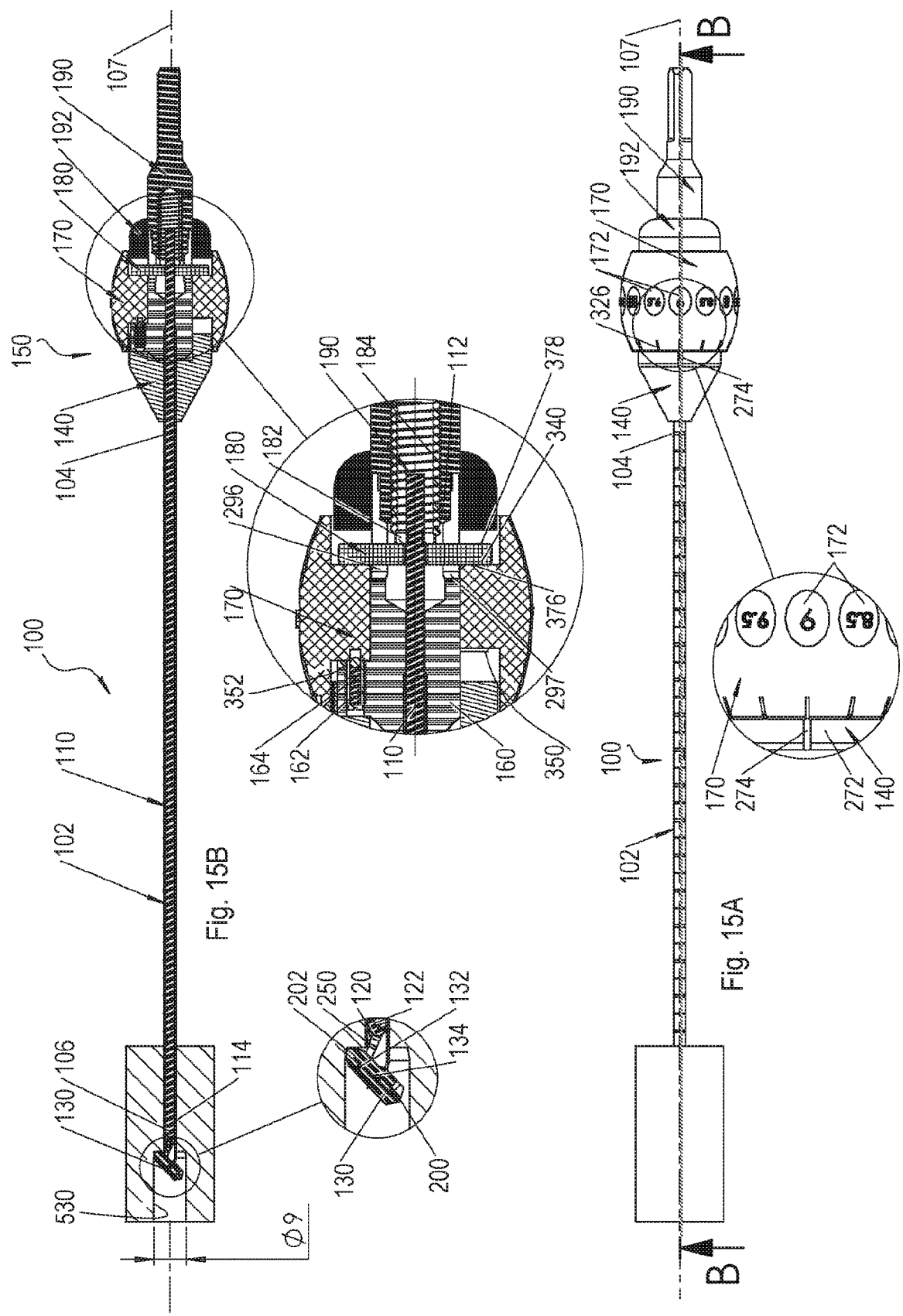

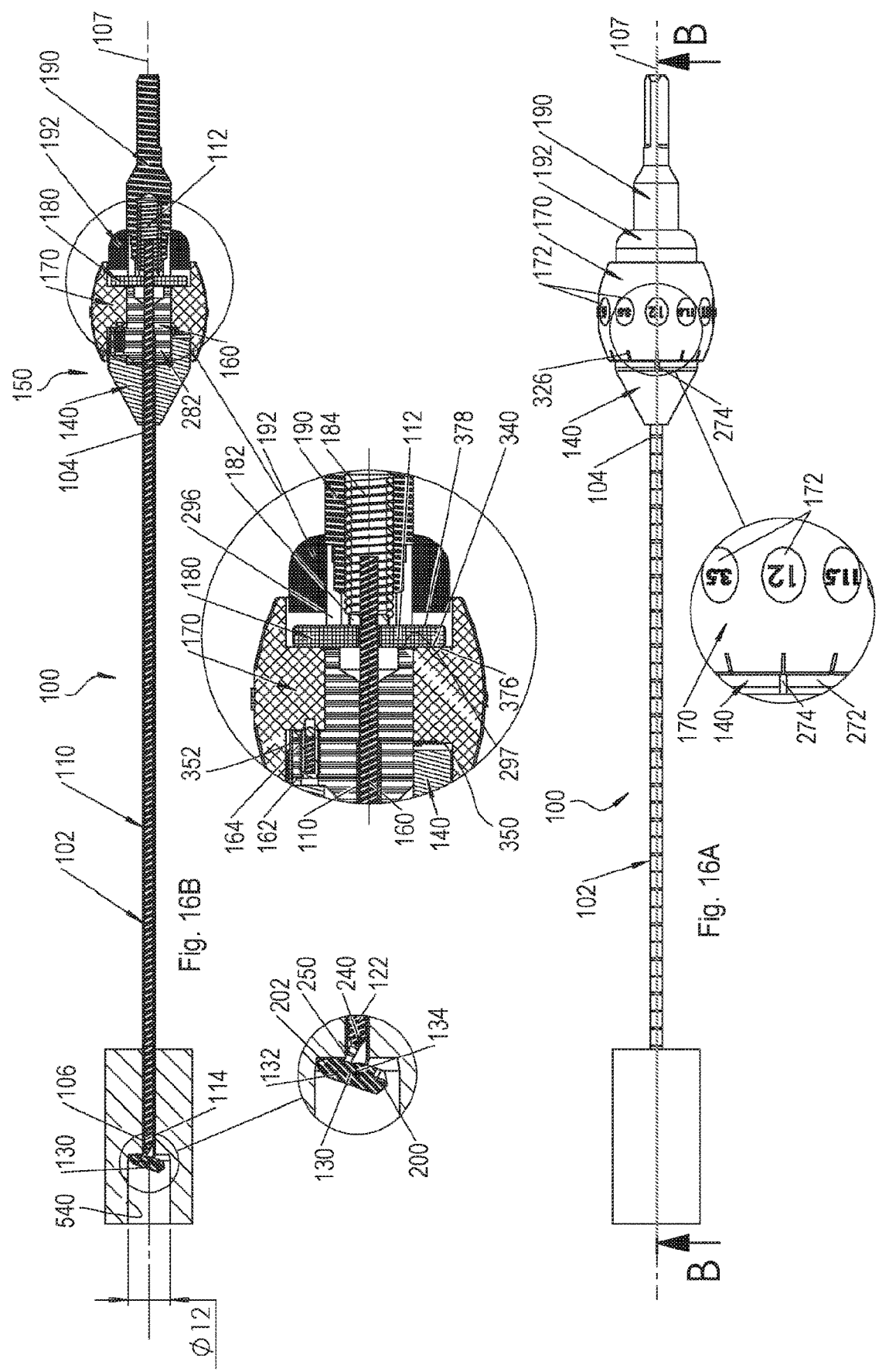

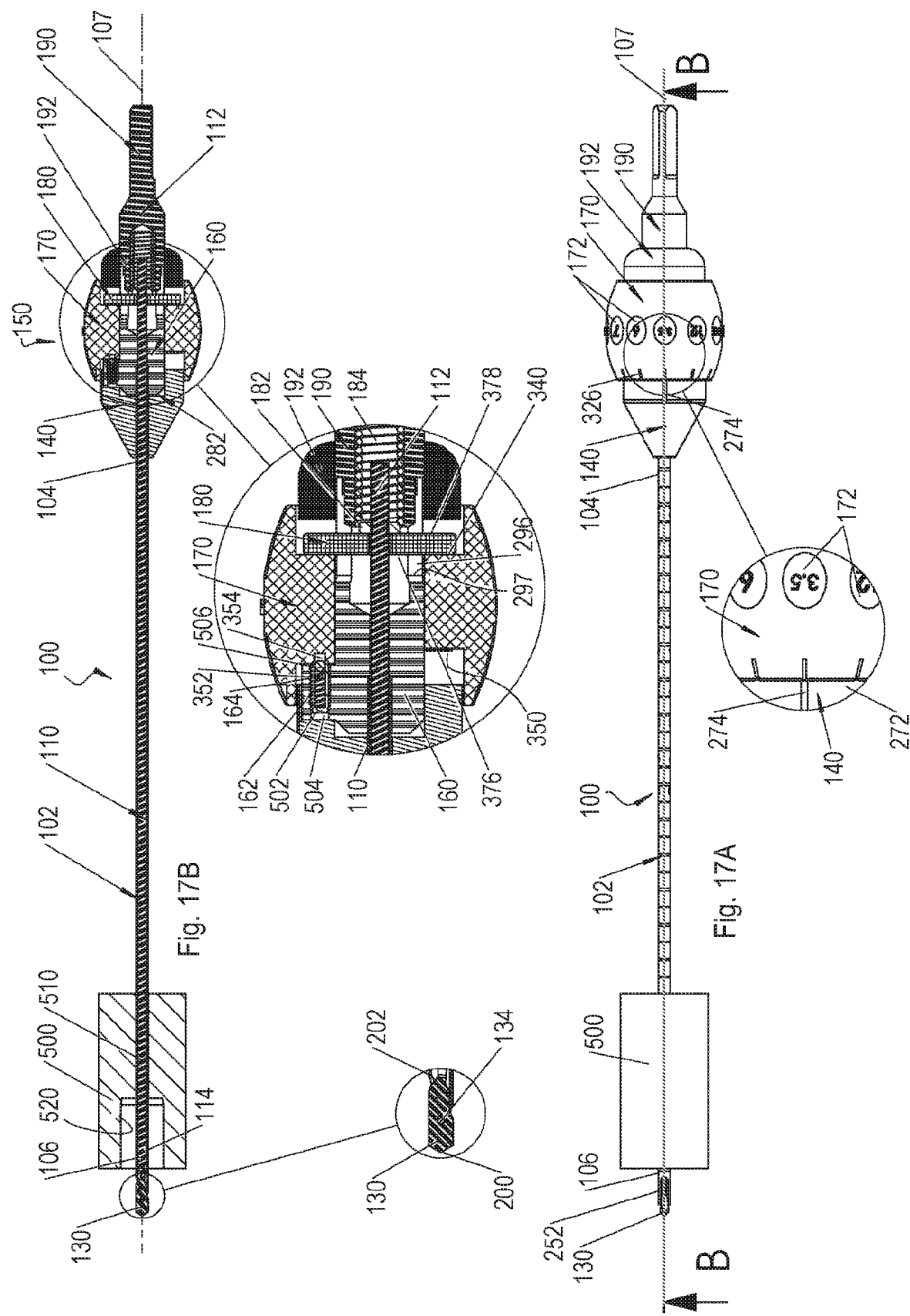

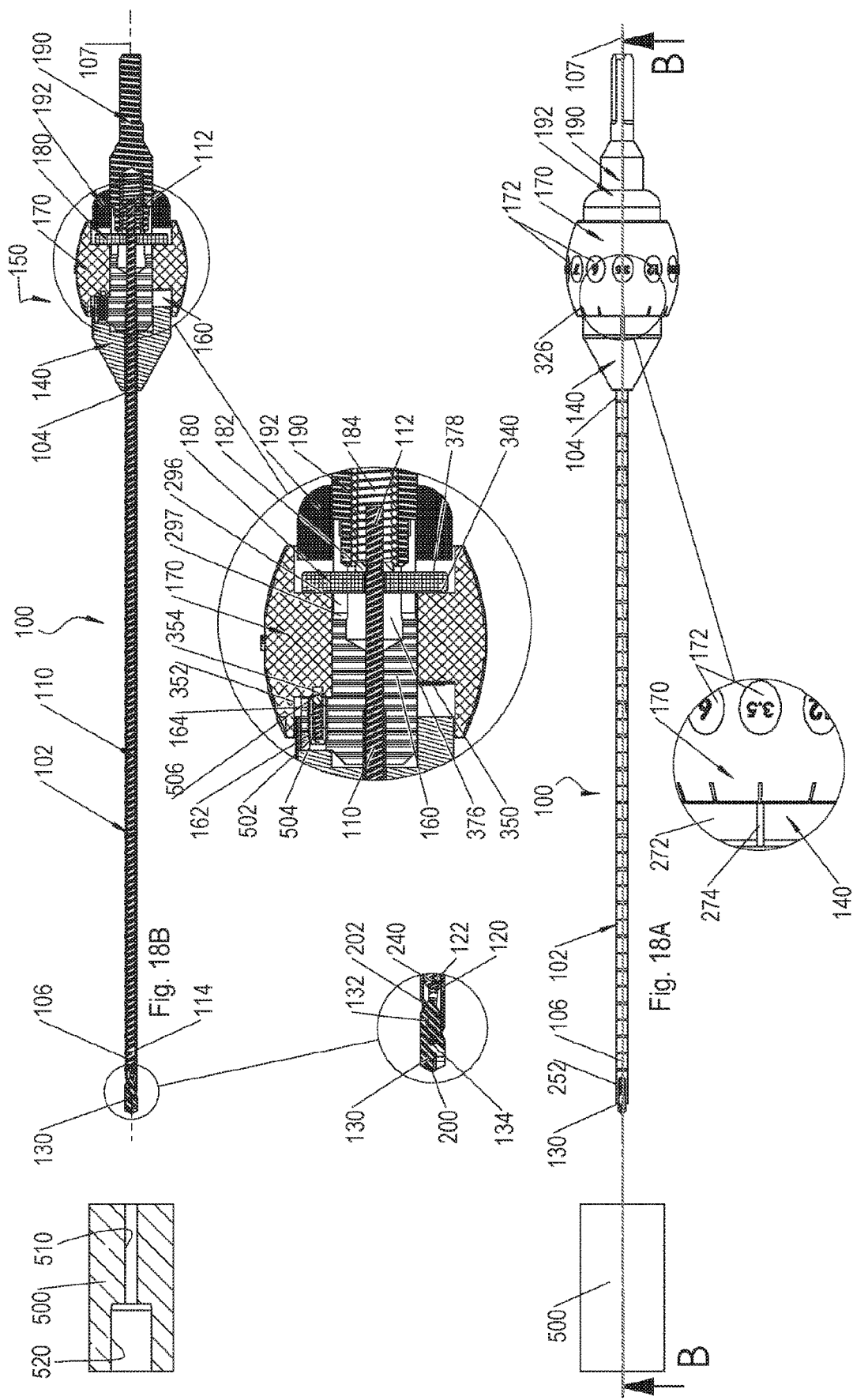

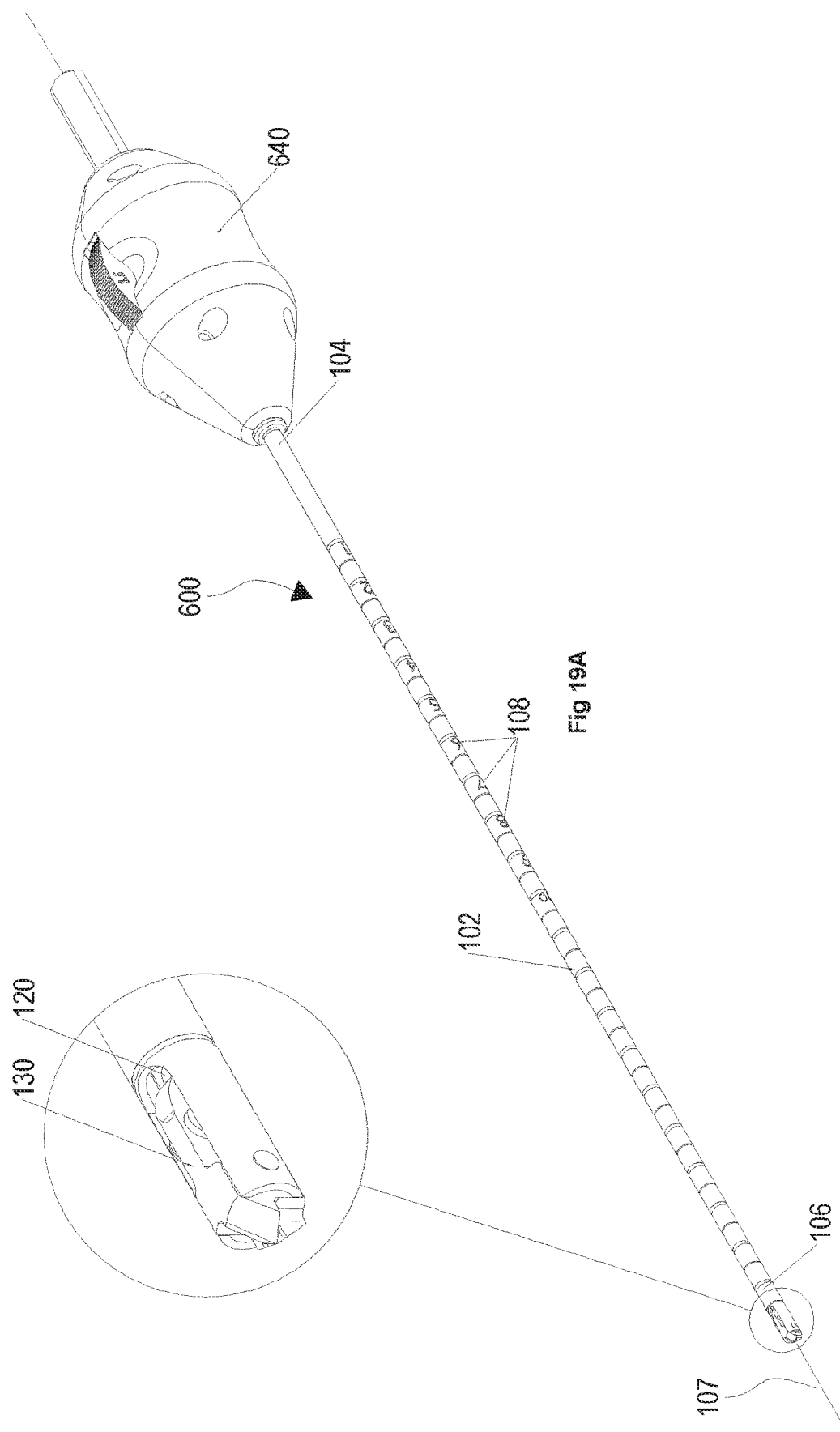

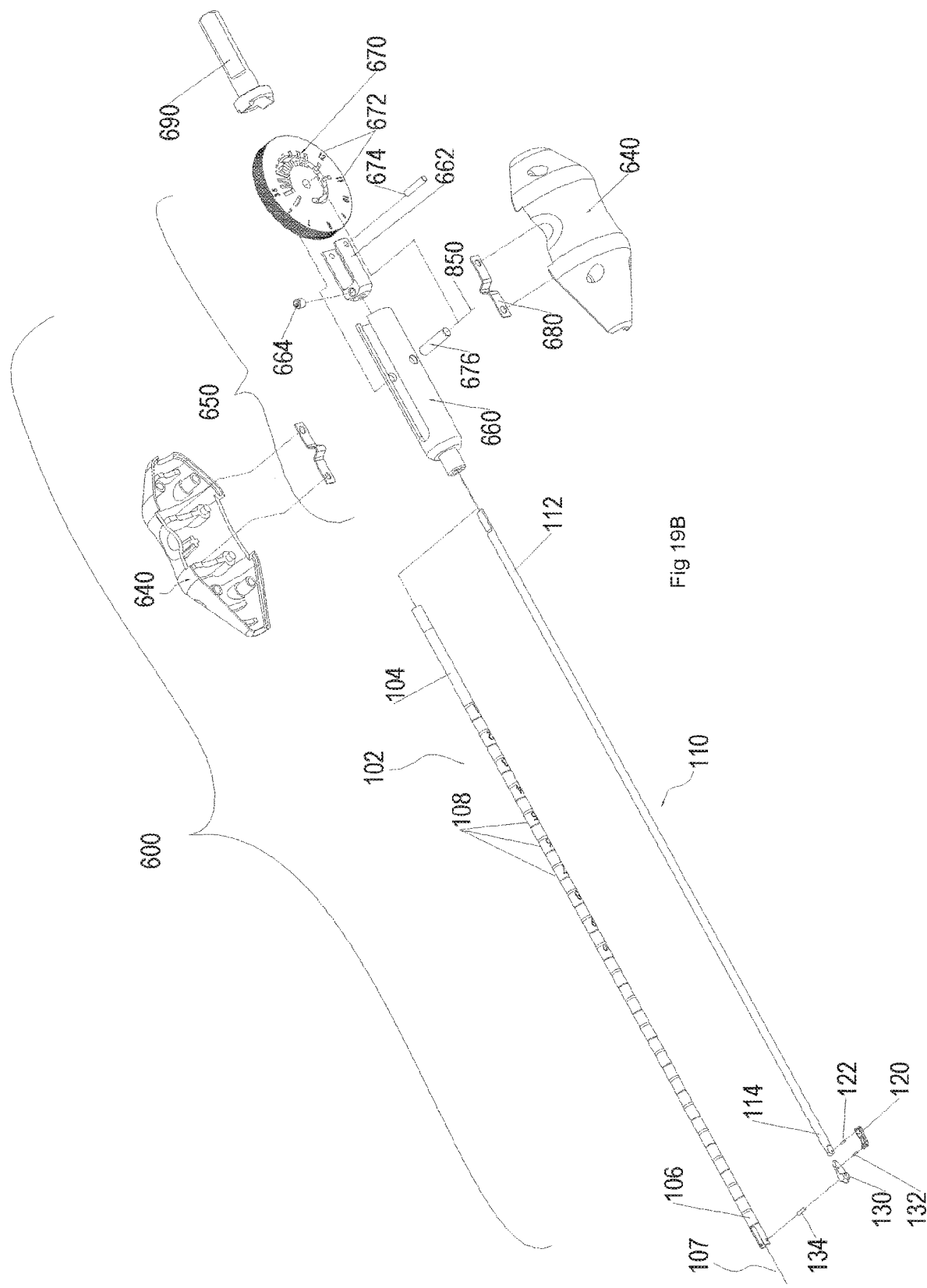

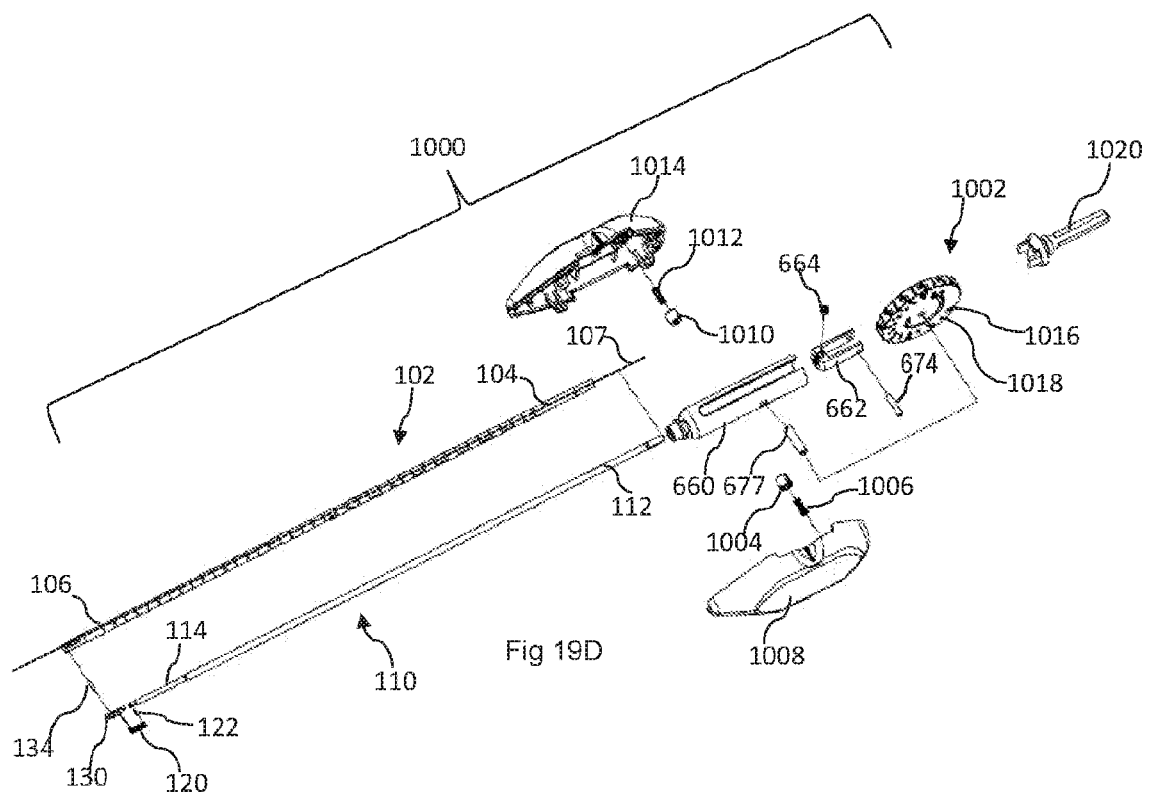

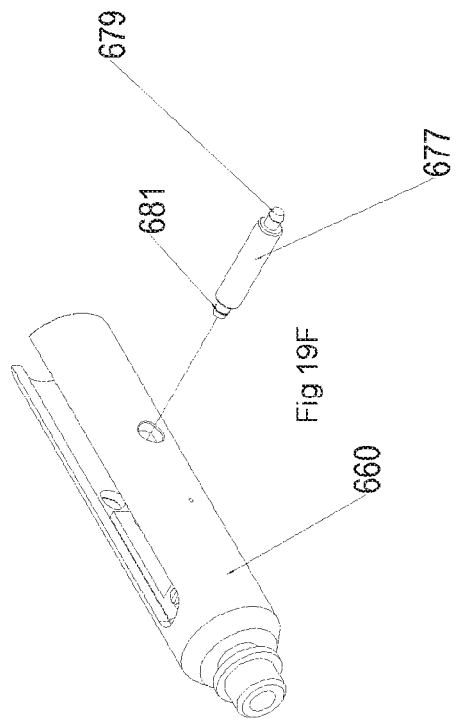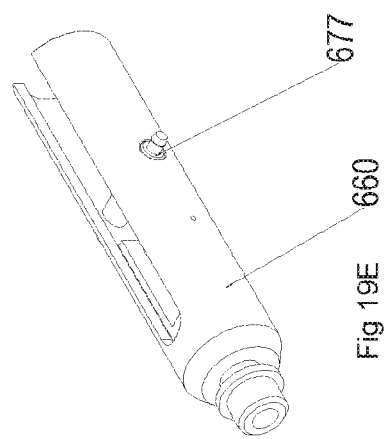

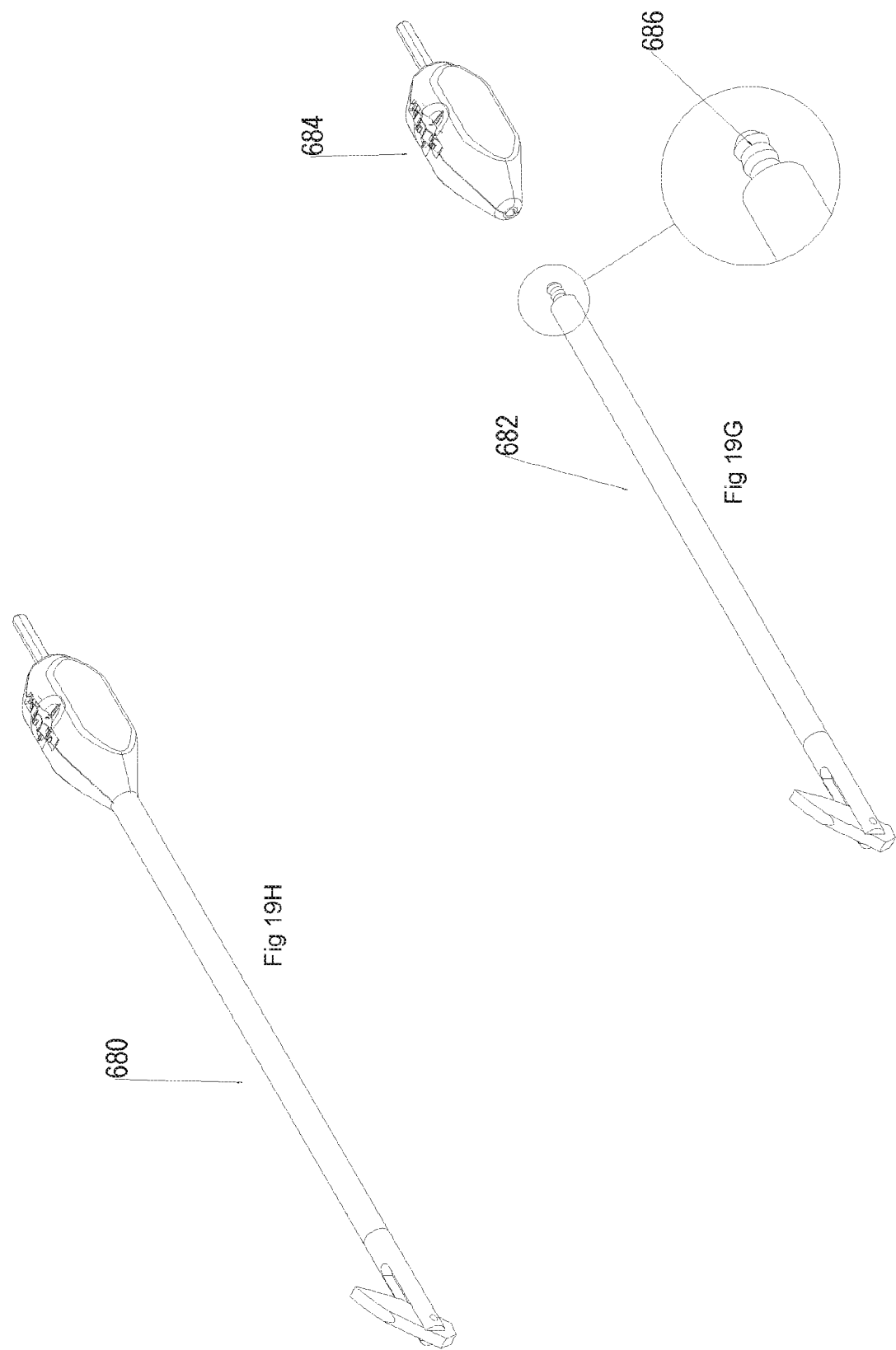

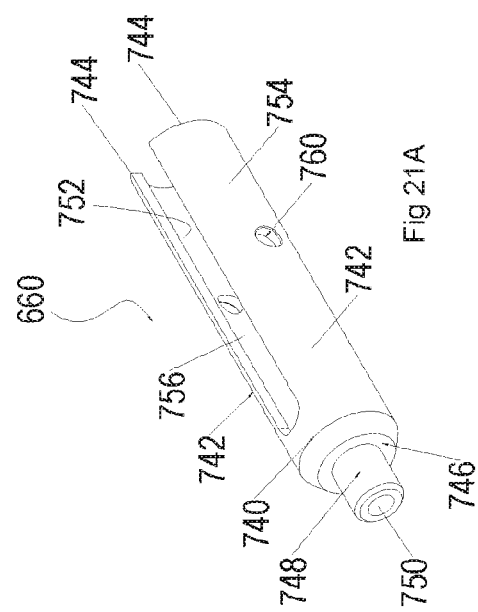
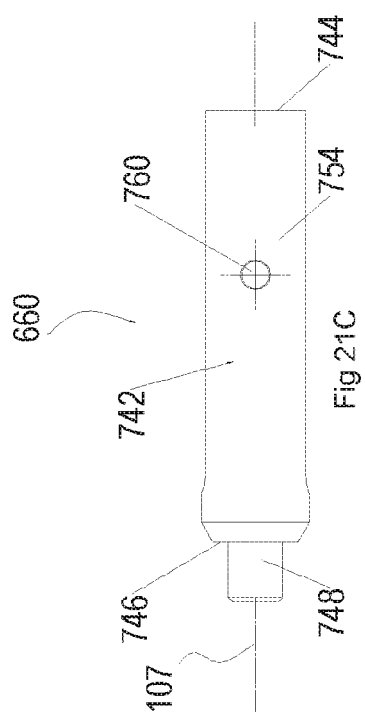
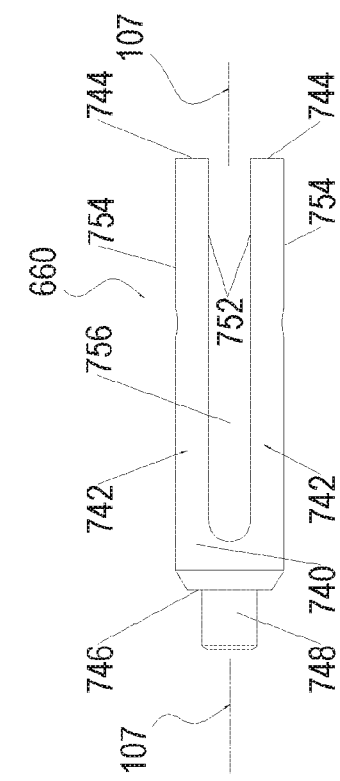

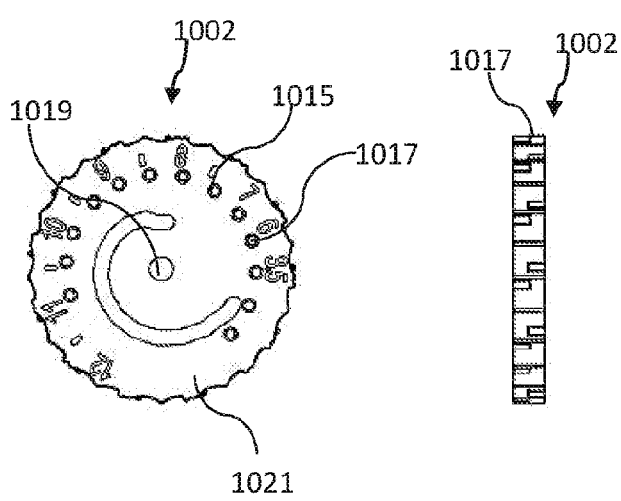
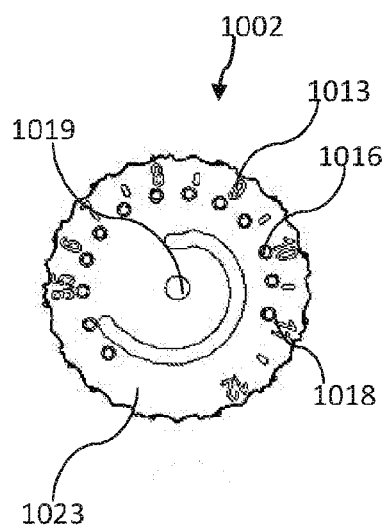
Fig. 22D   Fig. 22E   Fig. 22F

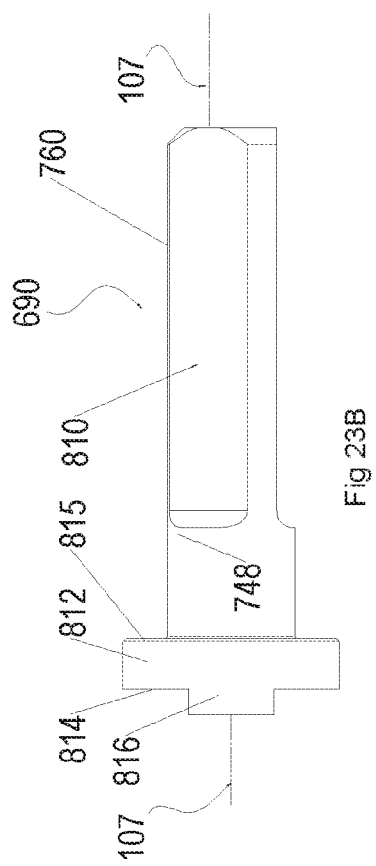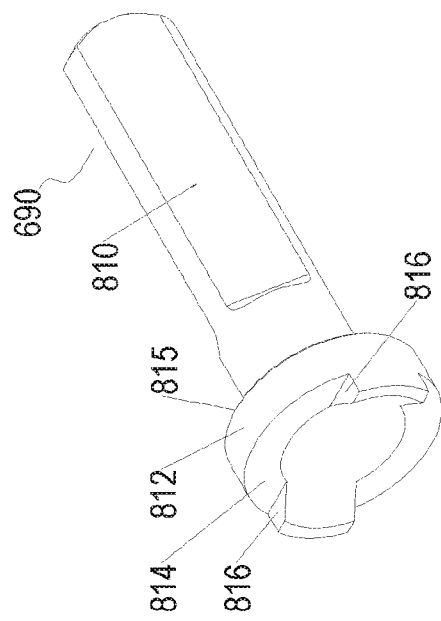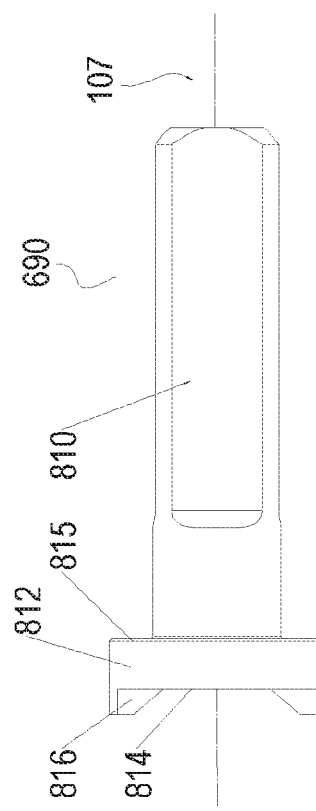

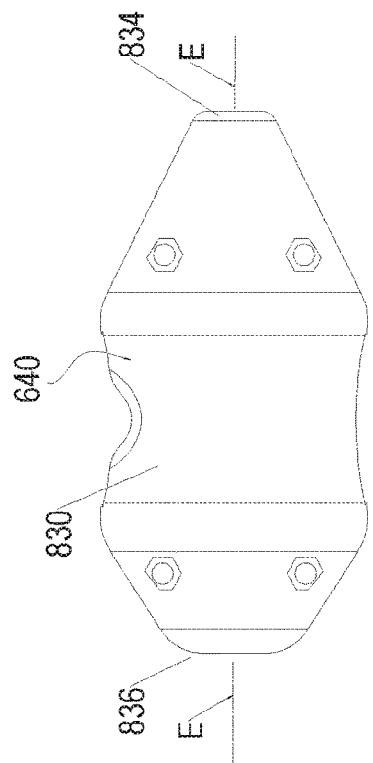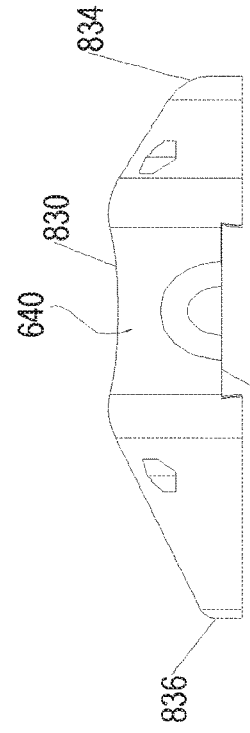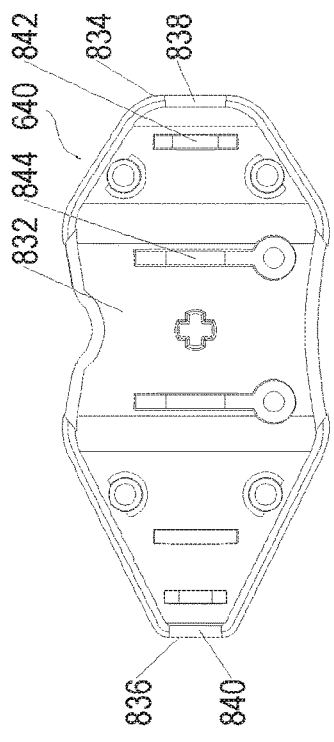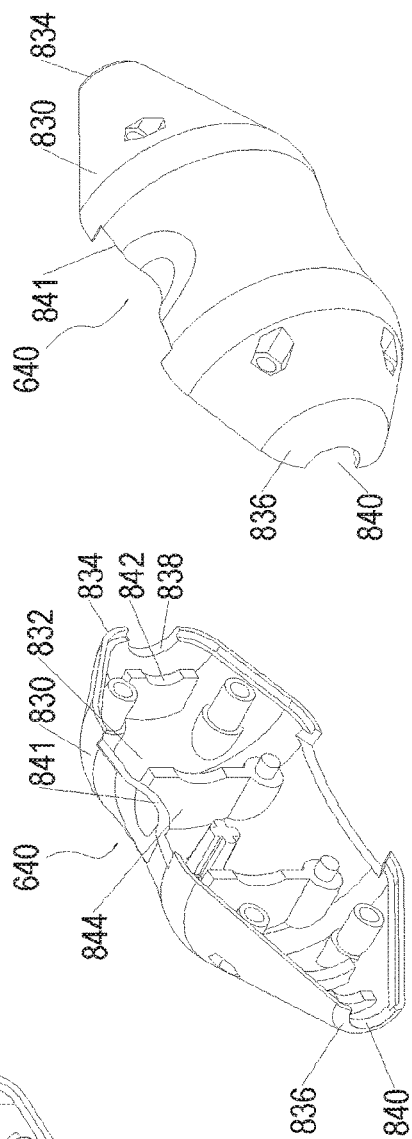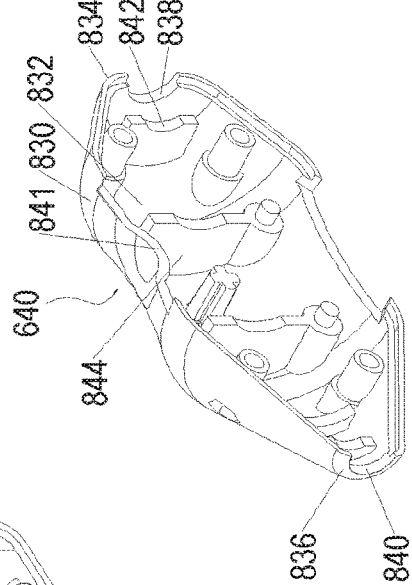

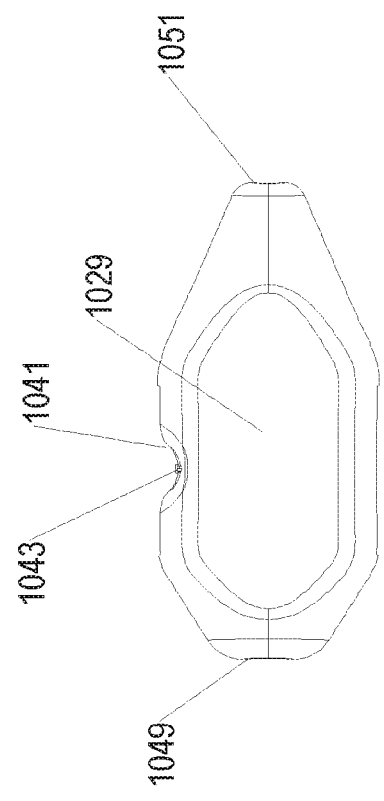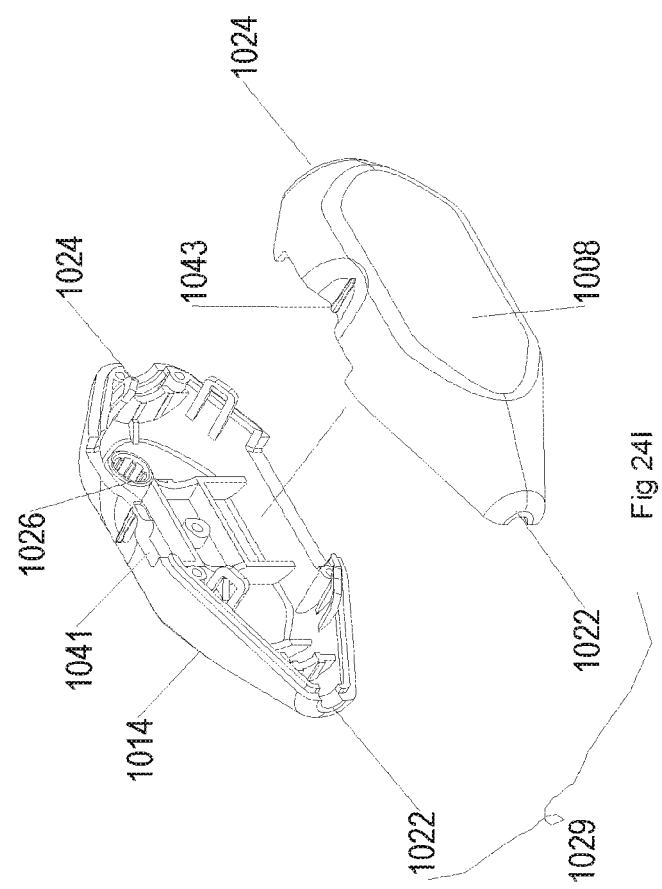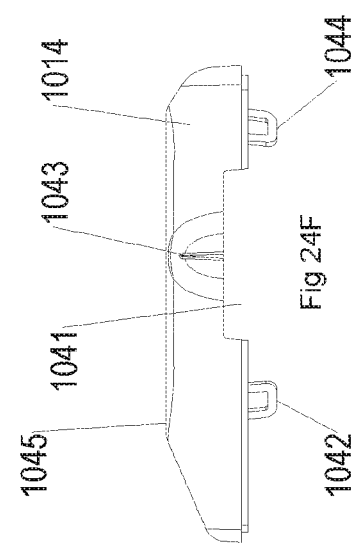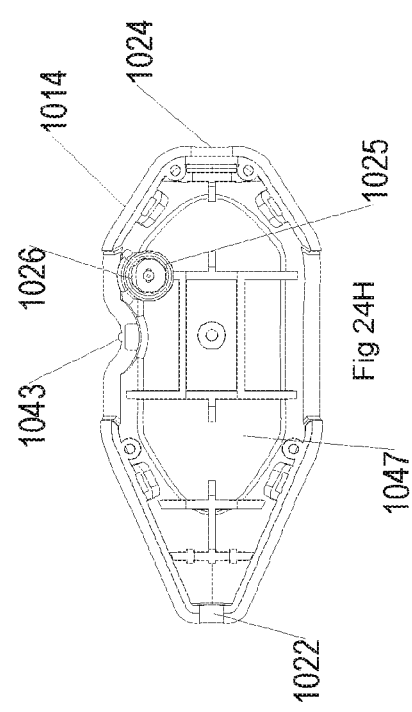

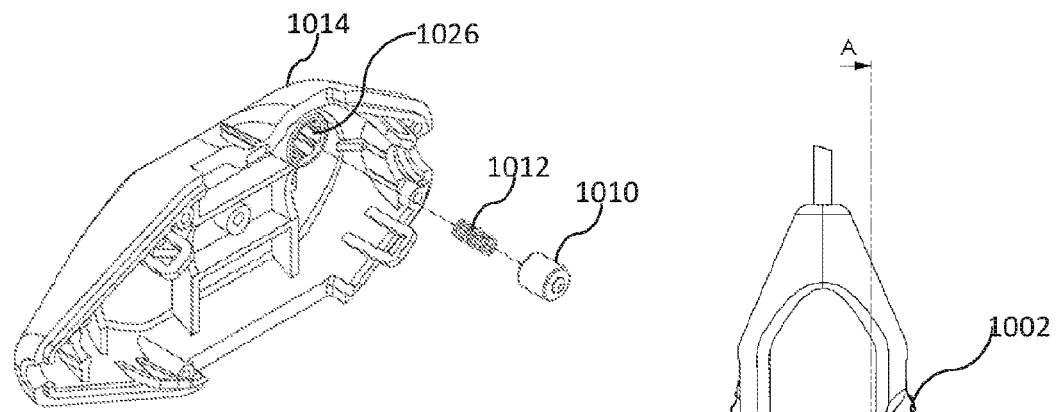
Fig. 24J
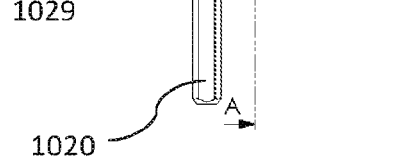
Fig. 24K
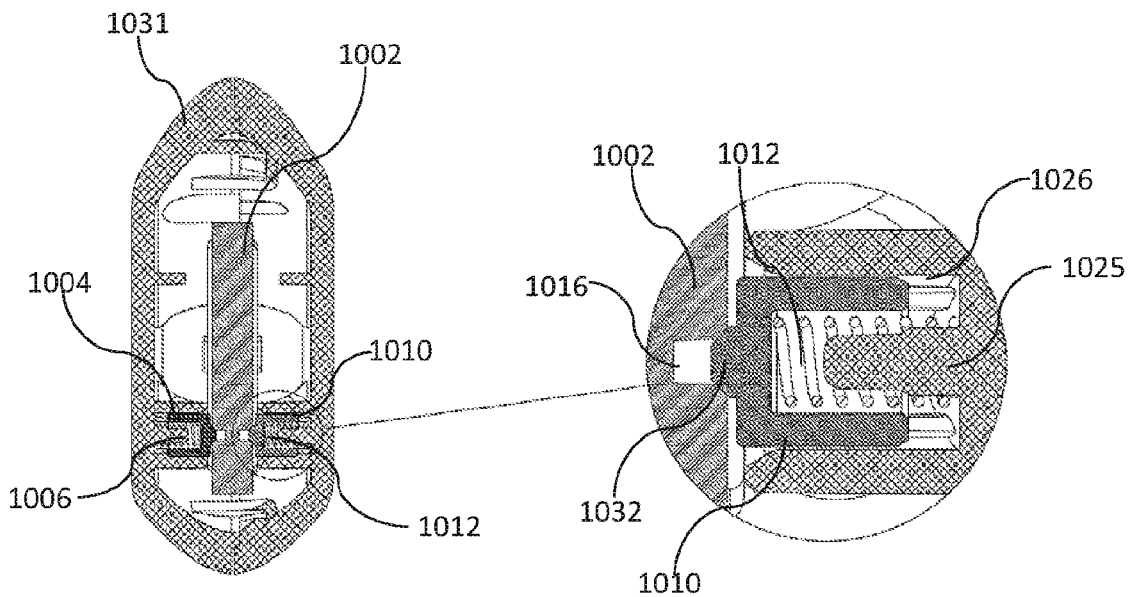
Fig. 24L
Fig. 24M

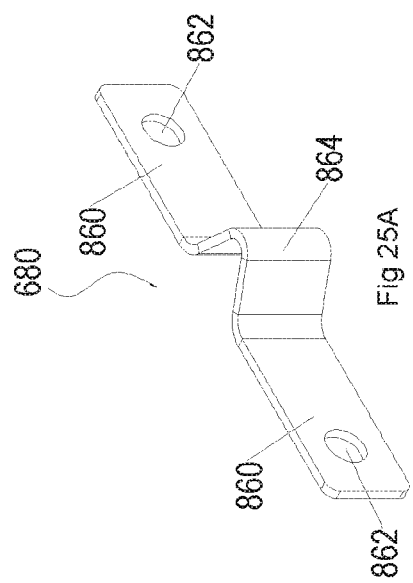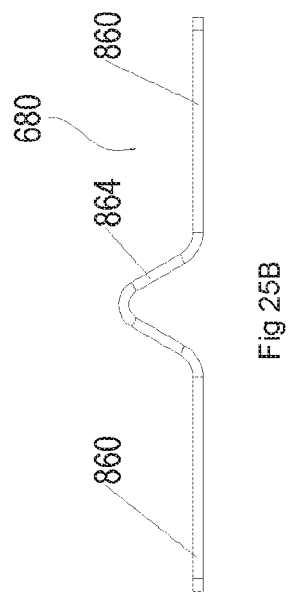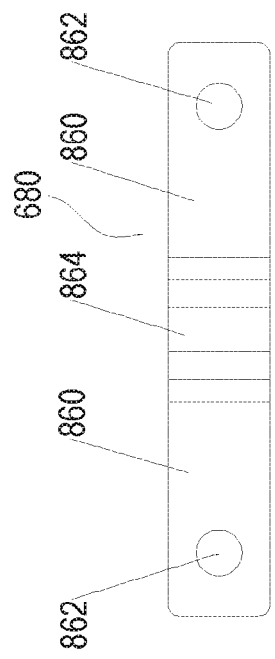

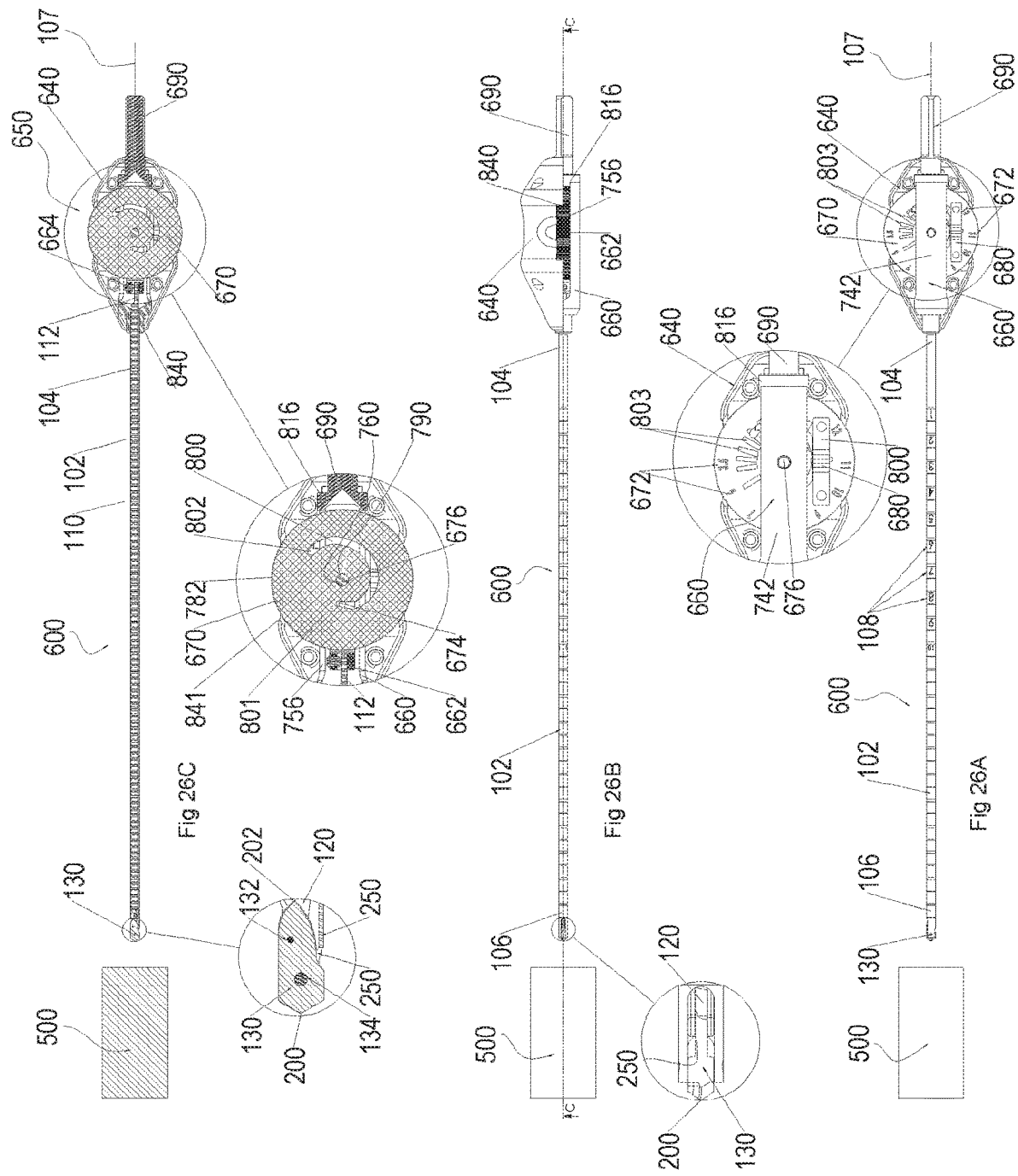

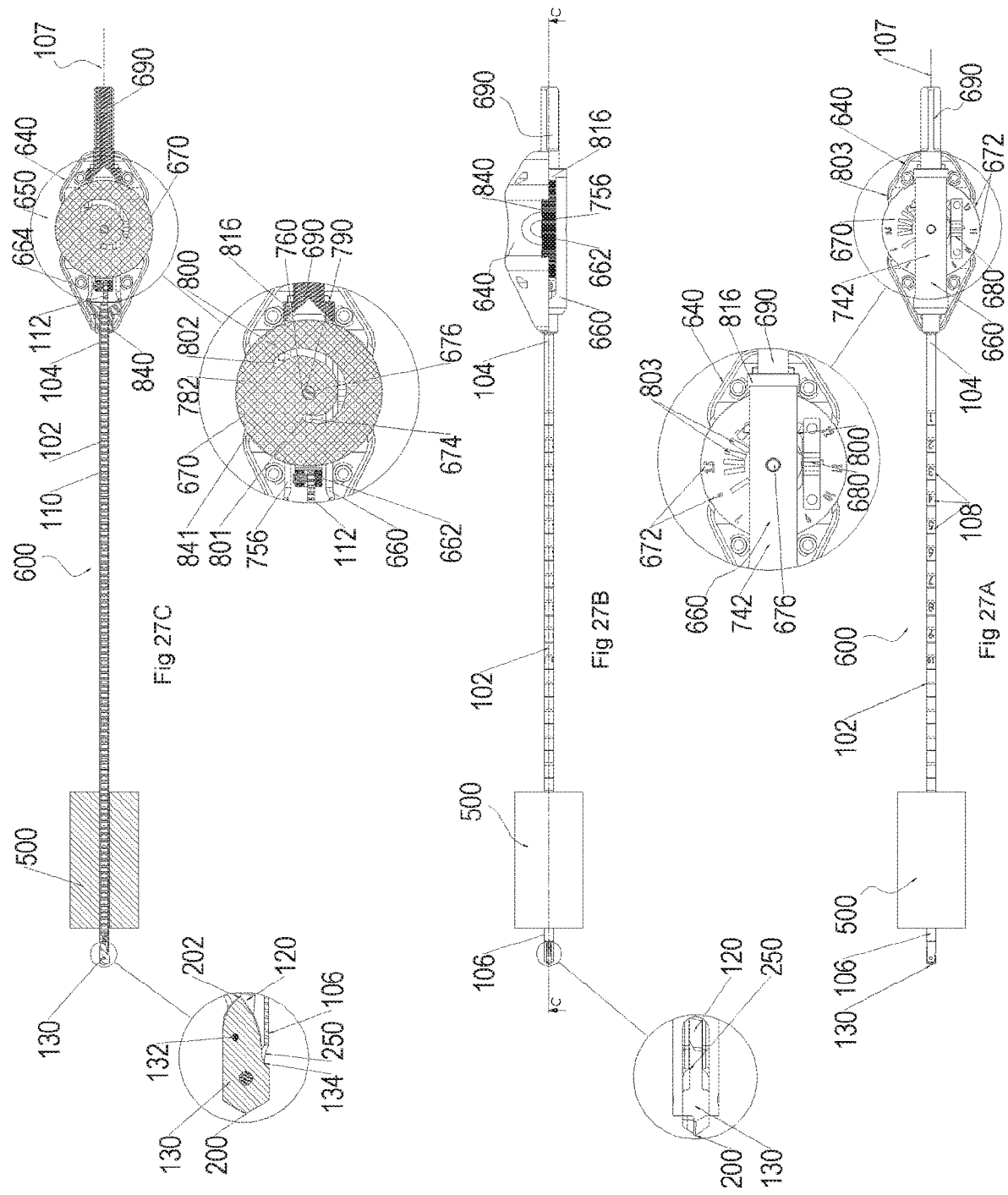

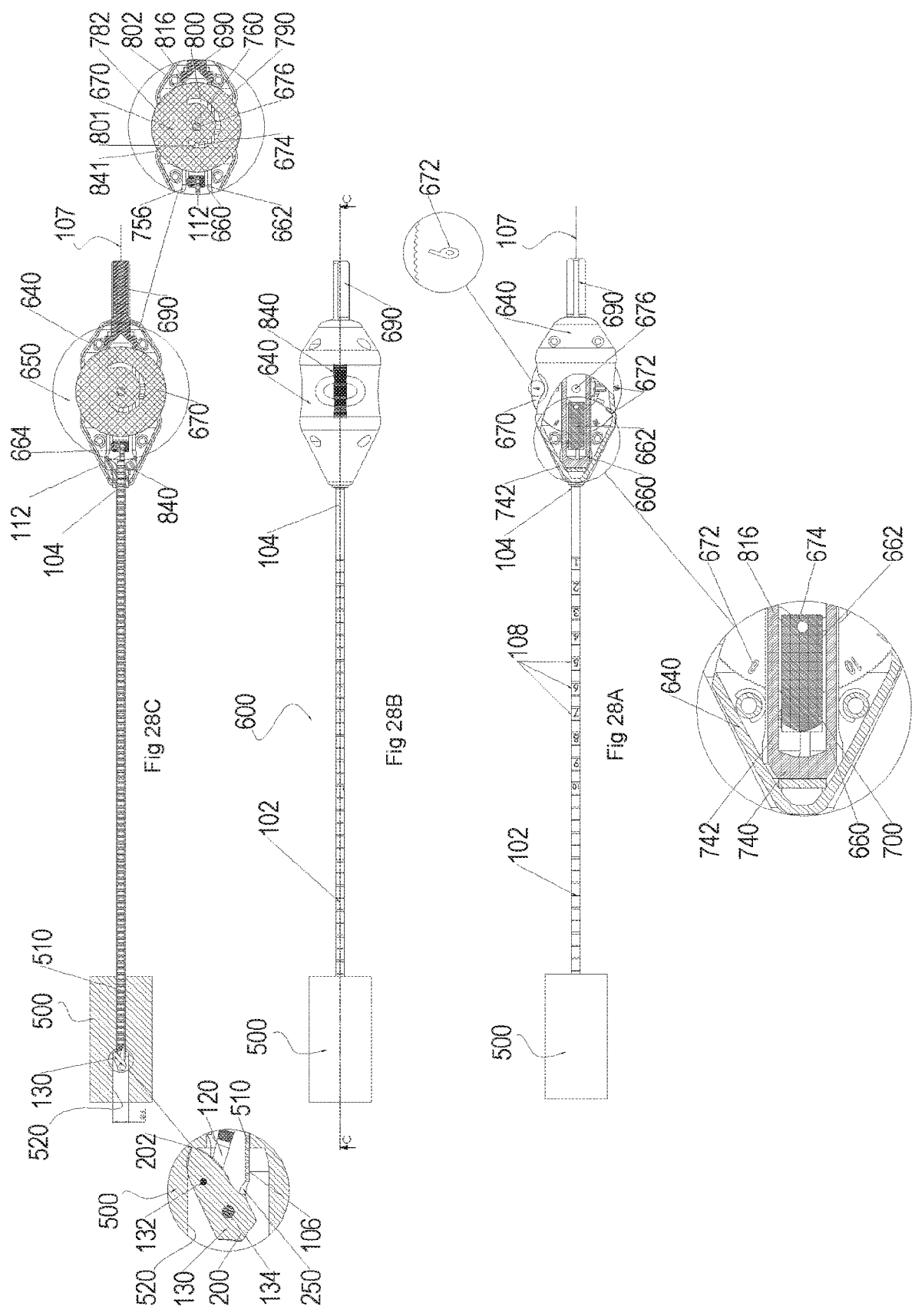

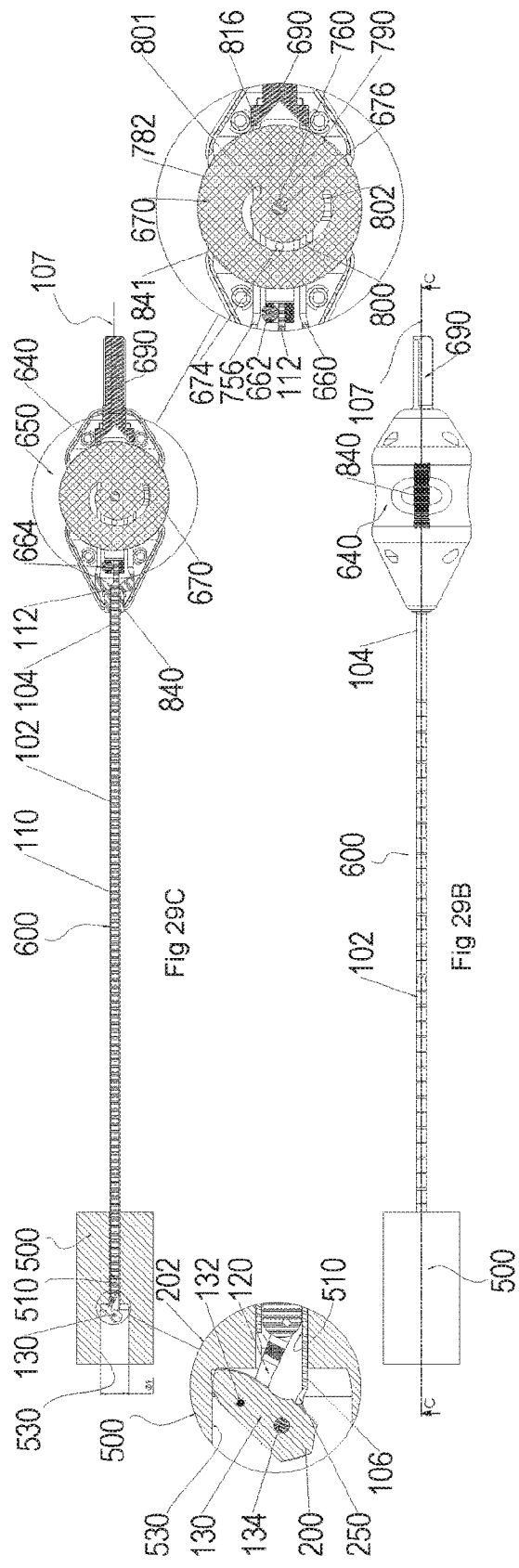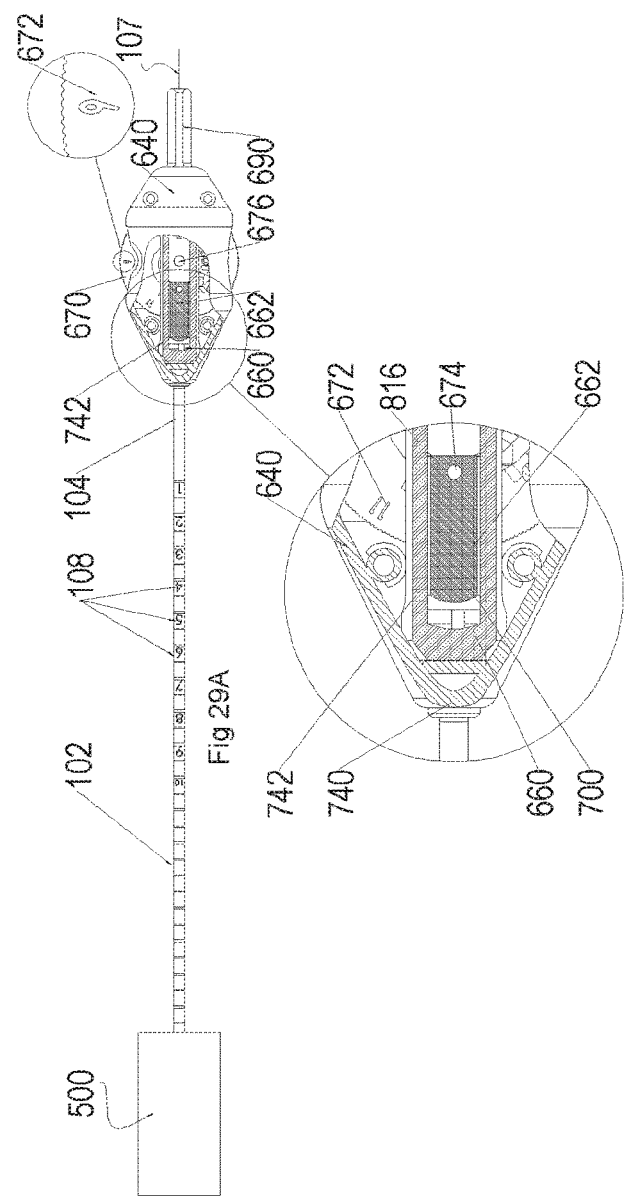

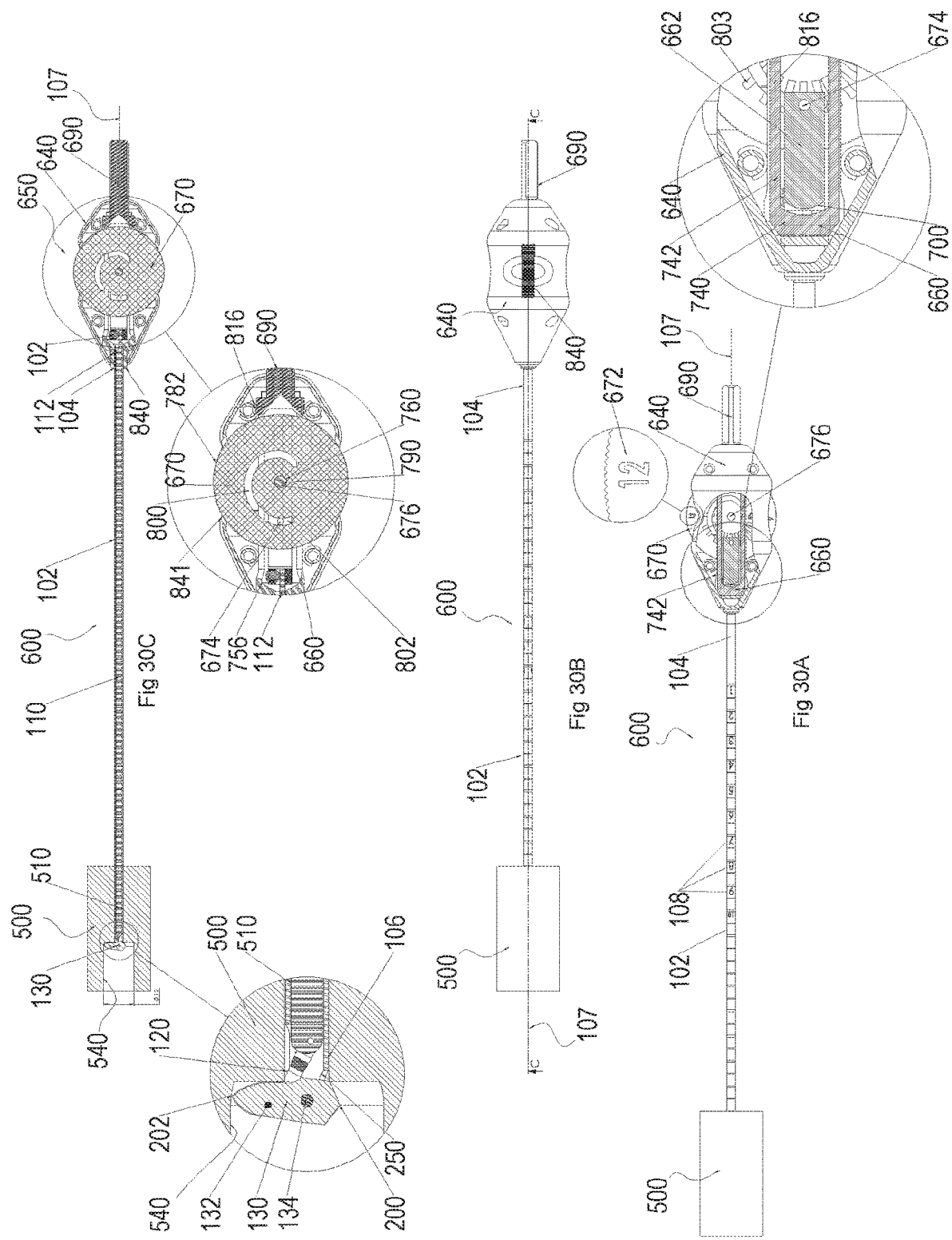

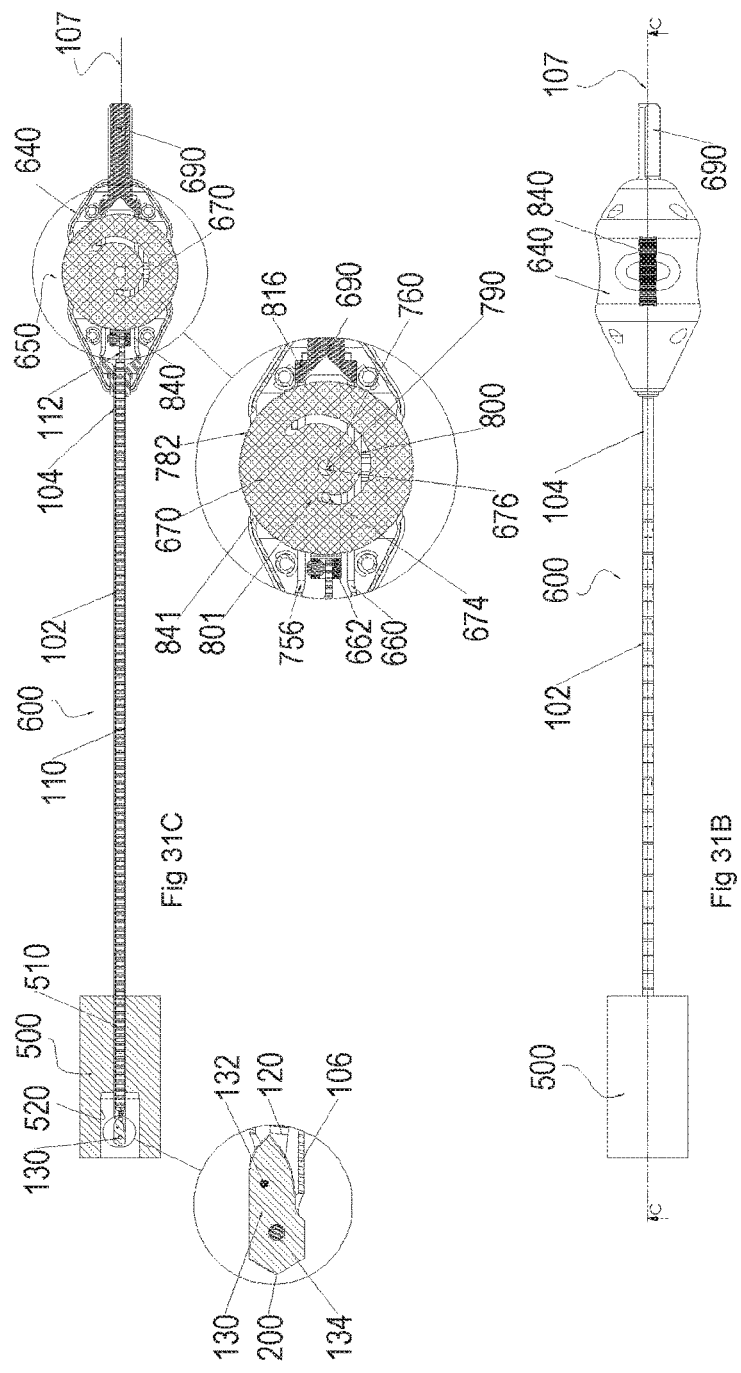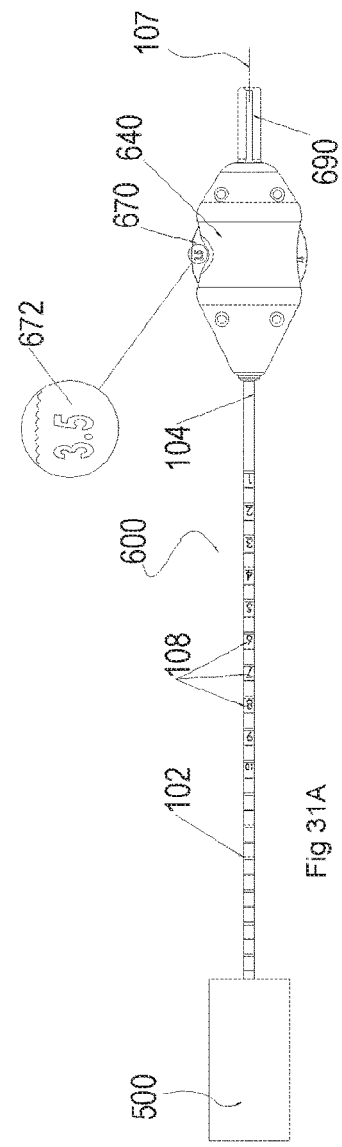
Fig 31C
Fig 31B
Fig 31A

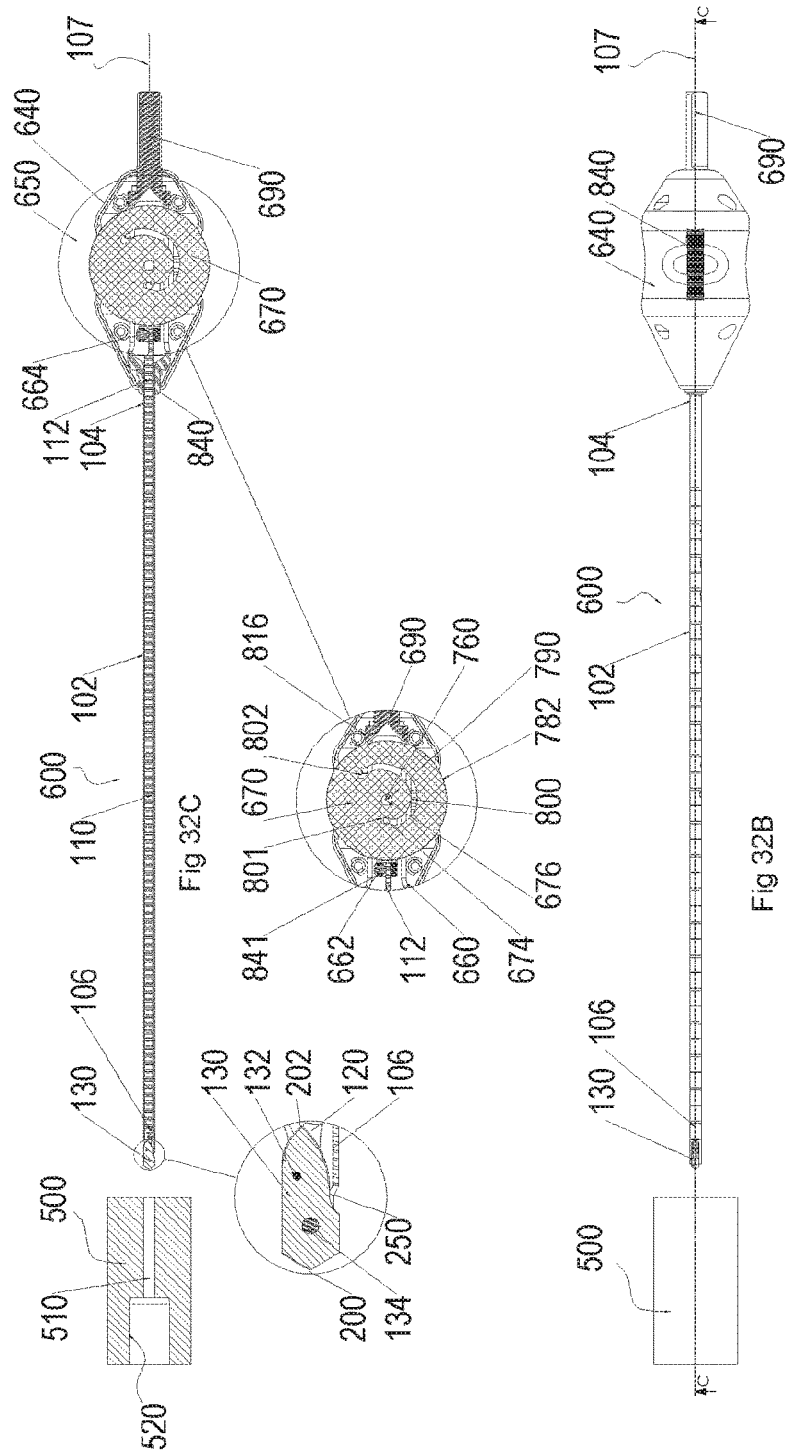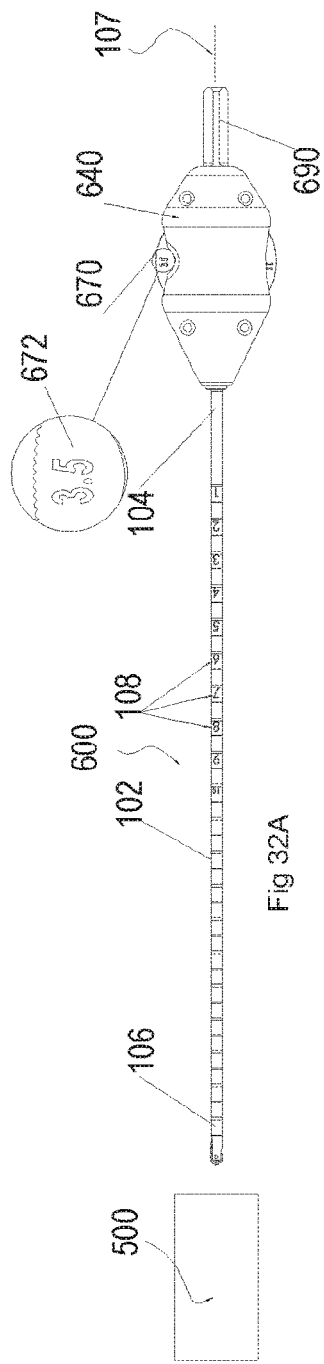

ADJUSTABLE DRILLING DEVICE AND A METHOD FOR USE THEREOF

RELATED APPLICATIONS

This application is a National Phase of PCT Patent Application No. PCT/IL2019/050876 having International filing date of Aug. 1, 2019, which claims the benefit of priority under 35 USC § 119(e) of U.S. Provisional Patent Application No. 62/713,014 filed on Aug. 1, 2018. The contents of the above applications are all incorporated by reference as if fully set forth herein in their entirety.

FIELD AND BACKGROUND OF THE INVENTION

The present invention generally relates to bone removal tools, for example, tools which change effective diameter and particularly relates to drills.

During various arthroscopic procedures drilling of a bore is required within a bone of a patient. In many occasions this bore has to have various diameters, such as an enlarged diameter for one or more of the following surgical procedures: insertion of an anchor, administration of a drug, insertion of a graft and insertion of an implant in AVN treatment procedures.

SUMMARY OF THE INVENTION

Some examples of some embodiments of the invention are listed below:

Example 1. A bone removal device, comprising:
an elongated shaft having a longitudinal axis, a distal end and a proximal end;
a bone borer having a distal drilling tip configured to drill into a bone tissue and at least one proximal reamer, wherein said bone borer is movably coupled to a distal end of said elongated shaft, wherein said bone borer is configured to move between a drilling state in which said drilling tip is placed in contact with bone tissue, and reaming states in which said at least one proximal reamer is placed in contact with the bone tissue.

Example 2. A device according to example 1, comprising a pusher element mechanically coupled to said elongated shaft and to said bone borer, wherein said pusher element is configured to tilt said bone borer relative to said longitudinal axis of said elongated shaft so as to provide said distal drilling tip in a forwardly facing position during said drilling state, and said at least one reamer in a radially extending position during said reaming states.

Example 3. A device according to example 2, wherein said pusher element is configured to tilt said bone borer in 30° degrees relative to said longitudinal axis of said elongated shaft.

Example 4. A device according to any one of example 2 or 3, comprising a rotatable adjuster coupled to said pusher element, wherein said rotatable adjuster is configured to rotate between two or more pre-determined stopping states each defines a different tilting angle of said bone borer relative to said longitudinal axis of said elongated shaft.

Example 5. A device according to example 4, wherein said rotatable adjuster rotates along an axis which is different from a rotation axis of said device.

Example 6. A device according to any one of examples 4 or 5, wherein said rotatable adjuster is configured to rotate around an axis different from a rotation axis of said bone removal device.

Example 7. A device according to any one of examples 4 to 6, wherein said adjuster comprises one or more visual indications for marking said two or more pre-determined stopping states.

Example 8. A device according to any one of examples 4 to 7, wherein said rotatable adjuster comprises a plurality of indentations each of said plurality of indentations corresponds to a single stopping state, and wherein said device comprises at least one elastic element configured to engage said plurality of indentations.

Example 9. A device according to example 8, wherein said adjuster is a disc-shaped adjuster, and wherein said plurality of indentations are located on at least one side wall of said disc-shaped adjuster.

Example 10. A device according to any one of examples 8 or 9, wherein said elastic element comprises a leaf spring or a spring plunger.

Example 11. A device according to any one of examples 2 to 10, comprising a crank having a longitudinal axis, a distal end with two distal protrusions shaped and sized to be pivotally connectable to said bone borer, and a proximal end with two spaced apart protrusions shaped and sized to be pivotally connectable to said pusher element.

Example 12. A device according to example 11, wherein said two distal protrusions are angled relative to said longitudinal axis of said crank.

Example 13. A device according to any one of the previous examples, comprising a bit connector mechanically coupled to said proximal end of said elongated shaft, wherein said bit connector is shaped and sized to be connected to a motorized or a manual driving unit of the device.

Example 14. A device according to any one of the previous examples, wherein said elongated shaft comprises an opening at said distal end, and wherein said bone borer is movably coupled to said elongated shaft within said distal opening.

Example 15. A device according to any one of the previous examples, wherein said movable bone borer is configured to be tilted at angle of up to 90° degrees relative to said longitudinal axis of said shaft.

Example 16. A device according to any one of the previous examples, wherein at a maximal tilting angle said bone borer radially extends to a distance of up to 6 mm from said elongated shaft.

Example 17. A device according to any one of the previous examples, wherein a length of said elongated shaft between said distal end to said proximal end is in a range of 5-30 cm.

Example 18. A device according to any one of the previous examples, wherein a maximal width of said elongated shaft is in a range of 1-7 mm.

Example 19. A device according to any one of the previous examples, comprising a crank having two side walls, configured to mechanically couple said bone borer to said elongated shaft.

Example 20. A device according to example 19, wherein said crank comprises at least two spaced-apart angled protrusions shaped and sized to hold said movable bone borer on both of said two side walls.

Example 21. A bone removal device, comprising:
an elongated shaft having a longitudinal axis, a distal end and a proximal end;
a movable bone borer movably coupled to said distal end of said elongated shaft, wherein said movable bone borer is configured to rotate around said longitudinal axis;
a rotatable bone borer adjuster coupled to said elongated shaft and to said movable bone borer, wherein said adjuster is configured to rotate around an axis which is different from a rotation axis of the movable bone borer.

Example 22. A device according to example 21, wherein a rotation axis of said adjuster is perpendicular to said rotation axis of the bone removal device.

Example 23. A device according to any one of examples 21 or 22, wherein said rotatable bone borer adjuster is configured to rotate between a plurality of stopping position, each of said plurality of stopping positions defines a discrete tilting angle of said bone borer relative to said longitudinal axis of said elongated shaft.

Example 24. A device according to any one of the previous examples, comprising a crank having two side walls, configured to mechanically couple said movable bone borer to said elongated shaft.

Example 25. A device according to example 24, wherein said crank comprises at least two spaced-apart angled protrusions shaped and sized to hold said movable bone borer on both of said two side walls.

Example 26. A bone removal device, comprising:
an elongated shaft having a longitudinal axis, a distal end having an opening crossing side to side through said elongated shaft and a proximal end;
a movable bone borer comprising a proximal reamer and is movably connected to said distal end and at least partly within said opening, wherein said movable bone borer is configured to move between a closed state in which said movable bone borer closes at least 90% of said opening in said shaft, and one or more open states in which said movable bone borer moves and defines a window of at least 10% of said opening.

Example 27. A device according to example 26, wherein said opening is shaped and sized to allow bone fragments to move from one side of said shaft to an opposite side of said shaft through said opening during reaming.

Example 28. A device according to any one of examples 26 or 27, wherein said movable bone borer comprises one or more curved reaming edges at a proximal end of said movable bone borer, configured to contact a bone tissue surface when said movable bone borer is in said one or more open states.

Example 29. A device according to example 28, wherein said one or more curved reaming edges have an angle smaller than 45° degrees relative to said bone tissue surface.

Example 30. A bone borer of a bone removal device, having a longitudinal axis, a distal end, and a proximal end, comprising:
at least one forwardly facing drilling tip having a width of less than 10 mm, at said distal end, shaped and sized to drill into a bone;
a proximal reamer spaced-apart from said drilling tip, shaped and sized to remove bone fragments during reaming.

Example 31. A bone borer according to example 28, wherein said reamer comprise two or more bone cutting edges, each of said two bone cutting edges is positioned on an opposite side wall of said proximal end.

Example 32. A bone borer according to example 31, wherein at least some of said two or more bone cutting edges converge to a single location.

Example 33. A bone borer according to any one of examples 30 to 32, wherein a maximal width of said bone borer distal end is in a range of 1-8 mm.

Example 34. A bone removal device, comprising:
an elongated body having a longitudinal axis, a distal end comprising an opening and a proximal end;
a movable bone borer movable within said opening;
a crank having two side walls, configured to mechanically couple said movable bone borer to said elongated body, wherein said crank comprises at least two spaced-apart protrusions shaped and sized to hold said movable bone borer on both of said two side walls.

Example 35. A device according to example 34, wherein each of said at least two spaced-apart protrusions are attached to a different side wall of said movable bone borer.

Example 36. A device according to any one of examples 34 or 35, wherein said at least two spaced-apart protrusions are curved.

Example 37. A bone removal kit, comprising:
a removable elongated shaft having a longitudinal axis, a distal end and a proximal end, comprising a movable bone borer coupled to said distal end;
a bone borer movement adjuster configured to adjust a movement of said bone borer relative to said elongated shaft;
at least one reversibly coupling connector coupled to said elongated shaft and/or to said bone borer movement adjuster; wherein said proximal end of said elongated shaft is removably coupled to said bone borer movement adjuster by said at least one reversibly coupling connector.

Example 38. A kit according to example 37, wherein said at least one reversibly coupling connector comprises a snap connector.

Example 39. A kit according to any one of examples 37 or 38, wherein said removable elongated shaft comprises a pusher element coupled to said bone borer, wherein said pusher element is configured to be removably coupled to said bone borer movement adjuster.

Example 40. A method for bone boring, comprising:
drilling into a bone using a bone borer of a drilling device to generate a bone opening;
tilting said bone borer relative to said drilling device;
reaming said bone opening by rotating said tilted bone borer.

Example 41. A method according to example 40, comprising:
fixing said tilted bone borer in a selected tilting angle prior to said reaming.

Example 42. A method for manufacturing a bone removal device, comprising: providing a movable cutting tooth, and a cutting tooth tilting angle adjuster;
aligning said movable cutting tooth and said adjuster in an alignment state;
functionally coupling said cutting tooth with said adjuster in said aligned state.

Example 43. A method according to example 42, wherein said aligning comprises placing said cutting tooth in a selected tilting angle relative to said device, and positioning said adjuster in a selected stopping state while keeping said cutting tooth in said selected tilting angle.

Example 44. A method according to any one of examples 42 or 43, wherein said functionally coupling comprises locking a screw to couple said cutting tooth to said adjuster.

Example 45. A method for assembly of a bone removal device, comprising:
determining a treatment type and/or a treatment region;
selecting an elongated shaft comprising a bone borer according to said determined treatment type and/or said determined treatment region;
removably coupling said elongated shaft to a bone borer movement adjuster of a bone removal device.

Example 46. A method according to example 45, wherein said removably coupling comprises removably coupling a pusher element controlling a tilting angle of said bone borer to said bone borer movement adjuster.

Example 47. A method according to any one of examples 45 or 46, comprising: decoupling said elongated shaft from said bone borer movement adjuster.

Example 48. A method of treatment using a bone removal device, comprising: determining a treatment type and/or a treatment region;

selecting an elongated shaft comprising a bone borer according to said determined treatment type and/or said determined treatment region;

removably coupling said elongated shaft to a bone borer movement adjuster of a bone removal device.

Example 49. A method according to example 48, wherein said removably coupling comprises removably coupling a pusher element controlling a tilting angle of said bone borer to said bone borer movement adjuster.

Example 50. A method according to any one of examples 48 or 49, comprising:

decoupling said elongated shaft from said bone borer movement adjuster.

The present invention seeks to provide an improved adjustable drilling device.

There is thus provided in accordance with an embodiment of the present invention an adjustable drilling device, including a pusher element arranged along a longitudinal axis and having a proximal end and a distal end; an adjusting element operatively attached to the proximal end of the pusher element and having an adjusting path; a cutting tooth operatively pivotably connected to the pusher element and wherein the pusher element is positionable in a distal operative orientation, upon axial displacement of the adjusting element, thereby causing the cutting tooth to assume at least a partially open operative orientation.

Preferably, the drilling device also includes a shaft element which at least partially surrounds the pusher element. Further preferably, the cutting tooth is disposed distally with respect to the shaft element. Still further preferably, the adjusting element is operatively engageable with an adjuster retainer, for example a plunger element, thus defining the extent of radial extension of the cutting tooth with respect to the shaft element. Yet further preferably, axial displacement of the adjusting element is urged by a spring.

In accordance with an embodiment of the present invention, an adjustable drilling device, including a shaft element arranged along a longitudinal axis and having a proximal end and a distal end; a cutting tooth operatively pivotably connected to the shaft element; an adjusting element operatively associated with the cutting tooth; and a spring which is configured for axially displacing the adjusting element in a distal operative direction.

Preferably, axial force of the spring permits radial extension of the cutting tooth with respect to the shaft element. Further preferably, the extent of the radial extension is defined by the extent of rotation of the adjusting element.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIGS. 1F and 1G are schematic illustrations of a bone borer, for example a cutting tooth, according to some exemplary embodiments of the invention;

FIG. 1H is a schematic illustration of shaft having a distal cut-out opening, according to some embodiments of the invention;

FIGS. 1I and 1J, are schematic illustrations of a bone borer within the distal cut-out opening of the shaft shown in FIG. 1H, according to some embodiments of the invention;

FIGS. 1L & 1M are respective simplified pictorial illustrations of an assembled view and an exploded view of a drilling device, constructed and operative, according to some embodiments of the invention;

FIGS. 2A-2C are a respective simplified pictorial illustration and two different plan views of a cutting tooth, forming part of the drilling device of FIGS. 1L & 1M, and according to some embodiments of the invention;

FIGS. 4A-4C are a respective simplified pictorial illustration and two different plan views of a pusher element, forming part of the drilling device of FIGS. 1L & 1M, and according to some embodiments of the invention;

FIGS. 5A-5D are a respective simplified pictorial illustration and three different plan views of a shaft element, forming part of the drilling device of FIGS. 1L & 1M, and according to some embodiments of the invention;

FIGS. 6A-6C are a respective simplified pictorial illustration, a plan view and a sectional view of a cover element, forming part of the drilling device of FIGS. 1L & 1M, the sectional view being taken along lines C-C in FIG. 6B, and according to some embodiments of the invention;

FIGS. 8A-8E are a respective simplified pictorial illustration, three different plan views and a sectional view of an adjusting element, forming part of the drilling device of FIGS. 1L & 1M, the sectional view being taken along lines E-E in FIG. 8C, and according to some embodiments of the invention;

FIGS. 11A-11C are respective simplified two different plan views and a sectional view of a sub-assembly of the drilling device of FIGS. 1L & 1M not showing the adjusting element of FIGS. 8A-8E, the sectional view being taken along lines C-C in FIG. 11B, and according to some embodiments of the invention;

FIGS. 12A & 12B are respective plan view and sectional view illustrations of the drilling device of FIGS. 1L & 1M shown in a closed operative orientation, before insertion into a bone of a patient, sectional view is taken along lines B-B in FIG. 12A, and according to some embodiments of the invention;

FIGS. 13A & 13B are respective simplified planar and sectional view illustrations of the drilling device of FIGS. 1L & 1M shown in the closed operative orientation, following forward drilling into the bone of the patient, sectional view is taken along lines B-B in FIG. 13A, and according to some embodiments of the invention;

FIGS. 14A & 14B are respective simplified planar and sectional view illustrations of the drilling device of FIGS. 1L & 1M shown in a first partially open operative orientation inserted into the bone of the patient, sectional view is taken along lines B-B in FIG. 14A, and according to some embodiments of the invention;

FIGS. 15A & 15B are respective simplified planar and sectional view illustrations of the drilling device of FIGS. 1L & 1M shown in a second partially open operative orientation inserted into the bone of the patient, sectional view is taken along lines B-B in FIG. 15A, and according to some embodiments of the invention;

FIGS. 16A & 16B are respective simplified planar and sectional view illustrations of the drilling device of FIGS. 1L & 1M shown in a fully open operative orientation inserted into the bone of the patient, sectional view is taken along lines B-B in FIG. 16A, and according to some embodiments of the invention;

FIGS. 17A & 17B are respective simplified planar and sectional view illustrations of the drilling device of FIGS. 1L & 1M shown in a closed operative orientation before removal from the bone of the patient, sectional view is taken along lines B-B in FIG. 17A, and according to some embodiments of the invention;

FIGS. 18A & 18B are respective simplified planar and sectional view illustrations of the drilling device of FIGS. 1L & 1M shown in a closed operative orientation following removal from the bone of the patient, sectional view is taken along lines B-B in FIG. 18A, and according to some embodiments of the invention;

FIGS. 19A & 19B are respective simplified pictorial illustrations of an assembled view and an exploded view of a drilling device, constructed and operative according to some embodiments of the invention;

FIG. 19D is a respective simplified pictorial illustration of an exploded view of a drilling device having a pin with an interference locking portion for securing the adjusting element, according to some embodiments of the invention;

FIGS. 19E and 19F are simplified pictorial illustrations of a pin with an interference locking portion coupled to a retainer of a drilling device, according to some embodiments of the invention;

FIGS. 19G and 19H are simplified pictorial illustrations of a drilling device having a replaceable shaft, according to some exemplary embodiments of the invention;

FIGS. 21A-21C are a respective simplified pictorial illustration and two different plan views of a retainer, forming part of the drilling device of FIGS. 19A & 19B, and according to some embodiments of the invention;

FIGS. 22D-22F are a respective simplified pictorial illustration and two different plan views of an adjuster, for example an adjusting element, configured to interact with one or more adjuster retainers, for example plungers, forming part of the drilling device of FIG. 19C, and according to some embodiments of the invention;

FIGS. 23A-23C are a respective simplified pictorial illustration and three different plan views of a bit connector, forming part of the drilling device of FIGS. 19A & 19B, and according to some embodiments of the invention;

FIGS. 24A-24E are a respective simplified pictorial illustration, two different plan views, and two sectional views of a cover element, forming part of the drilling device of FIGS. 19A & 19B, the sectional views being taken along lines E-E in FIG. 24B, and according to some embodiments of the invention;

FIGS. 24F-24I are a respective simplified pictorial illustration, including plan views and sectional views of a cover element, forming part of the drilling device of FIG. 19C, and according to some embodiments of the invention;

FIGS. 24J-24M are respective simplified pictorial illustrations of a spring plunger and an interaction between the spring plunger, an adjuster and a socket of a cover, forming part of the drilling device of FIG. 19C, and according to some embodiments of the invention;

FIGS. 25A-25C are a respective simplified pictorial illustration, and two different plan views of a leaf spring, forming part of the drilling device of FIGS. 19A & 19B, and according to some embodiments of the invention;

FIGS. 26A-26C are respective two different plan views and a sectional view illustration of the drilling device of FIGS. 19A & 19B shown in a closed operative orientation, before insertion into a bone of a patient, sectional view is taken along lines B-B in FIG. 26B, and according to some embodiments of the invention;

FIGS. 27A-27C are respective two different plan views and a sectional view illustration of the drilling device of FIGS. 19A & 19B shown in the closed operative orientation, following forward drilling into the bone of the patient, sectional view is taken along lines B-B in FIG. 27B, and according to some embodiments of the invention;

FIGS. 28A-28C are respective two different plan views and a sectional view illustration of the drilling device of FIGS. 19A & 19B shown in a first partially open operative orientation inserted into the bone of the patient, sectional view is taken along lines B-B in FIG. 28B, and according to some embodiments of the invention;

FIGS. 29A-29C are respective two different plan views and a sectional view illustration of the drilling device of FIGS. 19A & 19B shown in a second partially open operative orientation inserted into the bone of the patient, sectional view is taken along lines B-B in FIG. 29B, and according to some embodiments of the invention;

FIGS. 30A-30C are respective two different plan views and a sectional view illustration of the drilling device of FIGS. 19A & 19B shown in a fully open operative orientation inserted into the bone of the patient, sectional view is taken along lines B-B in FIG. 30B, and according to some embodiments of the invention;

FIGS. 31A-31C are respective two different plan views and a sectional view illustration of the drilling device of FIGS. 19A & 19B shown in a closed operative orientation before removal from the bone of the patient, sectional view is taken along lines B-B in FIG. 31B, and according to some embodiments of the invention; and FIGS. 32A-32C are respective two different plan views and a sectional view illustration of the drilling device of FIGS. 19A & 19B shown in a closed operative orientation following removal from the bone of the patient, sectional view is taken along lines B-B in FIG. 32B, and according to some embodiments of the invention.

DESCRIPTION OF SPECIFIC EMBODIMENTS OF THE INVENTION

Figure 1A:
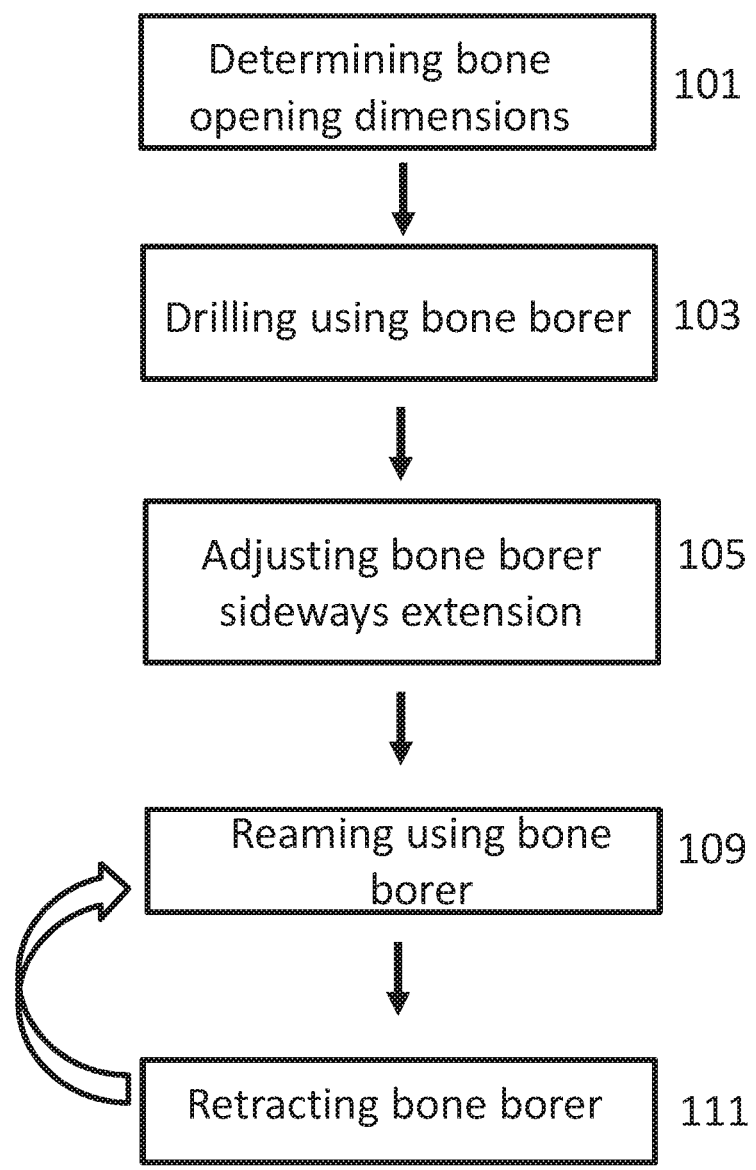
FIG. 1A is a flow chart of a drilling and reaming process, according to some embodiments of the invention.

The present invention generally relates to bone removal tools, for example, tools which change effective diameter and particularly relates to drills.

An aspect of some embodiments relates to bone removal device, for example a drilling device, having a bone borer for both bore drilling and selectively reaming, for example retrograde reaming. In some embodiments, the bone borer comprises at least one drilling tip and at least one separate reamer, comprising one or more reaming edges. In some embodiments, the bone borer moves between a drilling state and one or more reaming states by changing an orientation of the bone borer relative to the drilling device. In some embodiments, in each state one or both of the at least one drilling tip and the at least one reaming edge, are placed in contact with the tissue, for example bone tissue, cartilage tissue, muscle tissue or any other soft tissue of the body.

According to some embodiments, in a drilling state, the bone borer is axially aligned with a longitudinal axis of the drilling device. Optionally, in a drilling state, only the at least one drilling tip is placed in contact with the tissue. In some embodiments, in the one or more bore widening states, for example reaming states, the bone borer is tilted, for example at least a portion of the bone borer extends sideways relative to the longitudinal axis of the drilling device. In some embodiments, in the one or more bore widening states, the at least one reaming edge extends sideways and is placed in contact with the tissue. Optionally, in the one or more bore widening states, only the at least one reaming edge is placed in contact with the tissue. In some embodiments, when the bone borer is tilted, the bone borer or a longitudinal axis of the bone borer is positioned in an angle relative to the body, for example a shaft of the bone removal device or relative to a longitudinal axis of the shaft.

According to some embodiments, the bone borer moves between 2 or more sideways extension states, for example radial extension states, for example 2, 3, 4, 5, 6 or any larger number of sideways extension states. In some embodiments, the sideways extension states are pre-determined extension states. In some embodiments, each of the extension states is used to generate a potential bone opening with a different width, for example a diameter of an opening in the bone tissue. In some embodiments, when the bone borer is axially aligned with the longitudinal axis of the device, a width of the bone opening is similar to the maximal width of the forwardly facing end of the bone borer. Alternatively, when the bone borer is axially aligned with the longitudinal axis of the device, a width of the bone opening is larger in up to 10%, for example up to 10%, up to 5%, up to 2%, up to 1% or any intermediate, smaller or larger value, from the maximal width of the forwardly facing end of the bone borer.

According to some embodiments, sideways extending of the bone borer relative to the longitudinal axis of drilling device, for example while the bone borer rotates, increases a width of the bone opening in up to 5 times, for example up to 3 times, up to 2 times, compared to the maximal width of the forwardly facing end of the bone borer. In some embodiments, the bone borer is tilted in an angle in a range of 0-180° degrees, for example 0-45° degrees, 15-90° degrees, 45-135° degrees or any intermediate, smaller or larger angles range. In some embodiments, the bone borer sideways extends to a distance of up to 10 mm, for example up to 8 mm, up to 6 mm or any intermediate, smaller or larger distance, from the drilling device.

A potential advantage of having a bone removal device with a tilting bone borer is that this may allow a one-size-fits-all instrument useful for generating openings in the bone in different sizes using a single device.

An aspect of some embodiments relates to a bone borer for both forward drilling and sideways bone cutting. According to some embodiments, the bone borer comprises one or more drilling sections also termed herein as "drilling tip" or "drilling end", for example 1, 2, 3 or any larger number of drilling sections. Additionally, the bone borer comprises a reaming portion having one or more reaming edges, for example 1, 2, 3 or any larger number of reaming edges, spaced-apart and separate from the drilling sections. In some embodiments, the drilling sections are located at a distal end of the bone borer, and are optionally forwardly facing drilling sections, for example when the bone borer is axially aligned with the longitudinal axis of the drilling device. In some embodiments, the reaming edges are located at a proximal end of the bone borer.

According to some embodiments, the one or more reaming edges, are shaped and sized to remove bone fragments, for example when the bone borer is in one or more opening states. In some embodiments, the one or more reaming edges are shaped and sized to remove bone fragments when the bone borer is in an open state and is retracted within bone tissue. In some embodiments, the one or more drilling sections are configured to remove bone fragments, for example as the bone borer is axially advanced into the bone tissue. In some embodiments, the one or more drilling sections are integral elements of the bone borer, and are optionally stationary relative to the bone borer.

According to some embodiments, the one or more reaming edges are integral parts of the bone borer. In some embodiments, the one or more reaming edges are stationary relative to the bone borer. In some embodiments, the one or more reaming edges are sideways facing reaming edges, optionally located on a circumference of said bone borer close to, for example at a distance of up to 5 mm, for example 4 mm, 3 mm, 2 mm, 1 mm or any intermediate, smaller or larger value from a proximal end of the bone borer. In some embodiments, the reaming edges are shaped and sized to cut bone fragments when the bone borer is rotated and tilted. In some embodiments, when the bone borer is tilted, at least some of the one or more reaming edges are placed in contact with bone tissue. Optionally, when the bone borer is tilted, at least some of the reaming edges extend sideways against the bone tissue, for example as the bone borer is retracted within bone tissue.

An aspect of some embodiments relates to tilting a bone borer of a bone removal device to a closed position during or after retrograde reaming. In some embodiments, the bone borer is easily tilted to a closed position into an opening in a body of the bone removal device, by removing bone fragments from the body opening. Alternatively or additionally, the bone borer is easily tilted into the opening in the shaft by pushing one or more curved reaming edges at a proximal end of the bone borer by a bone tissue surface contacting the curved reaming edges as the device is retracted from the bone tissue.

According to some embodiments, the opening is located near the bone cutting site. In some embodiments, the opening is configured to move between closed and open positions. In some embodiments, during axial drilling the opening is closed. In some embodiments, during reaming, also termed herein as "widening", removed bone fragments are accumulated on one side of the bone removal device, the opening is opened, for example to allow passage of at least some of the removed bone fragments through the opening to an opposite side of the bone removal device.

According to some embodiments, the bone borer is positioned at least partly within the opening. Optionally, the bone borer is pivotally connected to the bone cutting device, at least partly within the opening. In some embodiments, during drilling, for example axial drilling, the opening is closed, for example at least 95%, at least 97%, at least 99% of the opening is closed, optionally by the bone borer. In some embodiments, during reaming, the opening is at least partially opened, for example at least 10%, at least 30%, at least 50% or any intermediate, smaller or larger percentage value of the opening is opened. In some embodiments, the opening is opened by movement, for example tilting, of the bone borer relative to the device. In some embodiments, the bone borer tilts at least 5° degrees relative to the device, for example at least 10° degrees, at least 25° degrees, at least 40° degrees or any intermediate, smaller or larger tilting angle relative to the device.

According to some embodiments, the bone borer comprises one or more curved reaming edges located at a proximal end of the bone borer. In some embodiments, the one or more curved reaming edges have an angle of less than 90° degrees, for example less than 45° degrees, less than 30° degrees or any intermediate, smaller or larger angle, relative to a surface of bone tissue contacting the bone borer during retraction of the bone borer from the bone.

An aspect of some embodiments relates to applying force on a drilling device for adjusting bone opening cutting width in a direction different from a rotation direction of the drilling device. In some embodiments, a bone borer adjusting mechanism, for example a bone cutting tooth adjusting mechanism of a drilling device rotates around an axis which is different from a drilling rotation axis of the device. In some embodiments, the cutting tooth adjusting mechanism rotates around an axis that is substantially perpendicular to a drilling rotation axis of the device. In some embodiments, the cutting tooth adjusting mechanism rotates around an axis positioned in an angle in a range of 10-90° degrees, for example 10-45° degrees, 30-70° degrees, 40-90° degrees or any intermediate, smaller or larger range of angles, relative to a drilling rotation axis of the device.

A potential advantage of rotating a bone cutting adjusting mechanism around an axis which is different from a rotating axis of the drilling device, may be reducing a risk that the rotation of the drilling device will affect the bone cutting adjusting mechanism.

An aspect of some embodiments relates to alignment of a bone cutting adjusting mechanism, of a drilling device, comprising a cutting tooth tilting angle adjuster positioned in a discrete retaining state, for example a discrete stopping state, with a selected position, for a selected tilting angle of a bone borer, for example a bone cutting tooth of the drilling device. As used herein, the word discrete means specific. In some embodiments, an adjusting mechanism formed at least partly from a polymer is aligned with a bone cutting tooth made from metal. In some embodiments, the bone cutting adjusting mechanism is fixedly coupled to the cutting tooth when the tooth is in the selected position and the adjusting mechanism is in the discrete retaining state. In some embodiments, the bone cutting adjusting mechanism is aligned with a selected position of the cutting tooth during the manufacturing of the drilling device According to some embodiments, a pusher element coupled to the cutting tooth is fixedly connected to the bone cutting adjusting mechanism, when the tooth is in the selected position and the adjusting mechanism is in the discrete retaining state. In some embodiments, the bone cutting adjusting mechanism comprises a rotating adjuster. In some embodiments, the rotating adjuster moves between a plurality of discrete retaining states, for example discrete stopping states. In some embodiments, the pusher element is fixedly connected to the rotating adjuster when said rotating adjuster is positioned at a selected discrete retaining state and said cutting tooth is positioned in said selected position.

According to some embodiments, for example during the manufacturing of the bone removal device, a movable cutting tooth placed in a selected tilting angle relative to an axis of the bone removal device is aligned with a cutting tooth tilting angle adjuster, positioned in a selected stopping state. In some embodiments, once the cutting tooth is aligned with the tilting angle adjuster, the aligned cutting tooth is functionally coupled to said aligned tilting angle adjuster. Optionally, the aligned cutting tooth and the aligned titling angle adjuster are mechanically coupled to a pusher element.

An aspect of some embodiments relates to holding a bone borer, for example a bone cutting tooth by at least two spaced-apart protrusions of a tooth holding element, each is attached to a sidewall of the bone borer, such that the bone borer is held from two sides, for example two opposite sides. In some embodiments, a portion of the spaced-apart protrusions contacting the sidewall of the bone cutting tooth is curved or angled. In some embodiments, the tooth holding element, for example a crank, is coupled, for example pivotally coupled, on a first end to the tooth, and on a second end to a movable rod, for example a pusher element. In some embodiments, the crank is pivotally connected to the movable rod by two spaced apart protrusions. Optionally, the two spaced-apart protrusions connecting the movable rod to the crank are straight.

A potential advantage of holding a movable tooth by two angled protrusions may be to increase the resistance of the bone borer against twisting forces, for example twisting forces that are applied on the bone borer during rotation of the bone borer while contacting bone tissue.

According to some embodiments of the invention, the drilling device when the bone cutting tooth is in a closed position, for example axially aligned with the longitudinal axis of device, drills a hole in a bone by a forwardly facing drilling tip. In some embodiments, the width of the drilled hole in the bone is defined by the maximal width of the drilling tip or the maximal width of the distal end of the cutting tooth. In some embodiments, in order to increase the width of the hole, the cutting tooth is used as a reamer.

According to some embodiments, for example during reaming, the cutting tooth is tilted between two or more pre-determined retaining states, for example pre-determined stopping states. In some embodiments, during reaming, for example retrograde reaming, the tooth is tilted in order to place in contact a sideways bone cutting edge, for example a proximal bone cutting edge, with the bone. In some embodiments, each pre-determined retaining state defines a different sideways extension distance of the bone cutting edge. In some embodiments, rotation of the drilling device, for example rotation of the cutting tooth in a closed position generates a bone opening with a width in a range of 2-4.5 mm, for example 2-3 mm, 2.5-4 mm, 3.5-4.5 mm or any intermediate, smaller or larger diameter. In some embodiments, rotation of the drilling device, for example when the cutting edge is in a maximal sideways extension distance, allows to form a bone opening having a width of 9-16 mm, for example 9-12 mm, 11-14 mm, 12-16 mm or any intermediate, smaller or larger width.

According to some embodiments, each pre-determined retention state of the bone cutting tooth relates to a different selected width of the opening, for example the bone opening. In some embodiments, a movable adjuster of the drilling device, controlling the titling angle of the tooth moves between the discrete pre-determined retaining states. In some embodiments, moving the adjuster between two successive retaining states, changes a width of the bone opening in 0.5-3 mm, for example 0.5-1.5 mm, 1-2 mm, 1.5-3 mm or any intermediate, smaller or larger value.

An aspect of some embodiments relates to adjusting a size of a drilling and reaming portion of a drilling device by replacing a bone borer and/or the bone borer adjusting mechanism. In some embodiments, a drilling and/or a reaming portion of the drilling device is removably coupled to an adjusting mechanism of the drilling device. In some embodiments, a bone borer is removably coupled to a body of the drilling device or to an adjusting mechanism, for example to allow easy replacement of the bone borer. Additionally or alternatively, a body of the drilling device, for example a shaft optionally comprising a bone borer, is removably coupled to an adjusting mechanism of the drilling device, for example to allow easy replacement of the body with the bone borer.

A potential advantage of having a replaceable bone borer or shaft may be to allow easy adjustment of the drilling device to different pediatric and/or veterinary applications that need to have a shorter and/or a wider body or a bone borer in different sizes.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

Exemplary Process for Drilling and Reaming of a Bone Opening

According to some exemplary embodiments, an opening is formed in a bone, for example in Femur/Tibia, shoulder—scapula, clavicle, humerus or any other type of bone for that matter. In some embodiments, the opening is formed in two stages, a drilling stage, in which a drill penetrates into a bone, for example to form an initial bore within the bone, and a reaming stage, in which the bore is widened to a desired width. Reference is now made to FIG. 1A, depicting a process for forming an opening in a bone by drilling and reaming using a bone borer, according to some exemplary embodiments of the invention.

According to some exemplary embodiments, desired bone opening dimensions are determined at block 101. In some embodiments, the desired bone opening properties are determined based on a clinical application, an anatomical location of the bone opening, relative distance to other tissues, for example blood and nerve tissues and clinical condition of the patient.

In some embodiments, the bone opening properties comprise bone opening maximal depth, bone opening minimal and/or maximal width and/or bone opening shape and/or based on the size of the ligament or the root of the meniscus.

According to some exemplary embodiments, a bone borer, for example a bone borer of a bone removal device is used to drill into the bone to form an initial bore, at block 103. In some embodiments, the bone borer drills to a desired depth into the bone. In some embodiments, a drilling tip, for example a distal forwardly facing drilling tip of the bone borer is used for the drilling at block 103.

According to some exemplary embodiments, sideways extension of the bone borer is adjusted at block 105. In some embodiments, the sideways extension of the bone borer is adjusted by modifying a tilting angle of the bone borer relative to the drilling device, for example relative to a longitudinal axis of the drilling device. In some embodiments, a portion of the bone borer extends sideways, for example radially extends, relative to a perimeter of the drilling device, for example relative to a drilling device shaft. In some embodiments, the sideways extension of the bone borer determines a reaming width, for example a reaming diameter of the bone opening. In some embodiments, sideways extension of the bone borer positions one or more reaming edges on the periphery of the bone borer, optionally close, or at a proximal end of the bone borer, in contact with bone tissue.

According to some exemplary embodiments, the bone borer is used for widening, for example reaming the bone opening at block 109. In some embodiments, during reaming, the bone borer is rotated while at least a portion of the bone borer extends sideways and contacts bone tissue. Optionally, during reaming at block 109 the bone borer is retracted. In some embodiments, during reaming, the bone borer sideways extension are adjusted, for example to modify the reaming width, for example increase or decrease reaming width.

According to some exemplary embodiments, the bone borer is retracted at block 111. In some embodiments, the bone borer is retracted during the reaming process, for example as explained at block 111. Alternatively, the bone borer is retracted once the reaming process is over, for example when forming an inner wide void in the bone tissue that has a narrow opening. In some embodiments, once the bone borer is retracted, reaming is repeated at block 109.

Exemplary Cutting States During Drilling and Reaming

Figure 1B:
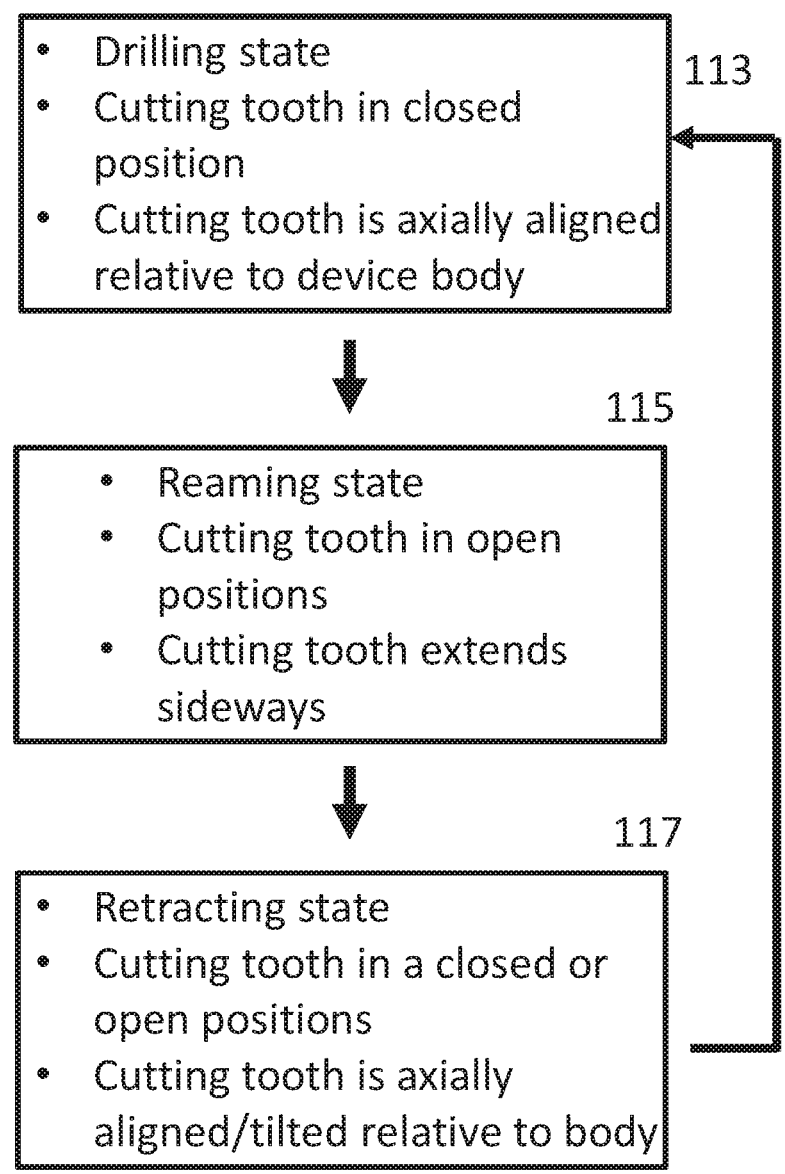
FIG. 1B is a state diagram describing bone borer states during drilling, reaming and retracting states, according to some embodiments of the invention.

According to some exemplary embodiments, a bone borer, for example a cutting tooth, of a bone removal device is mechanically coupled to a body, for example an elongated shaft, having a distal end, a proximal end and a longitudinal axis, of the bone removal device. In some embodiments, the bone borer is movable, relative to the body. In some embodiments, the bone borer is configured to move between a closed state in which the bone borer is aligned with a longitudinal axis of the body, and one or more sideways extending states, for example one or more radial extending states, in which the bone borer is tilted relative to the longitudinal axis of the body. In some embodiments, in the closed state, the bone borer is located within a perimeter defined by the body external surface. In some embodiments, in the one or more sideways extending states, the bone borer extends out from the perimeter. Reference is now made to FIG. 1B, depicting changes in the bone borer orientation relative to the body of the bone removal device during the bone boring process, according to some exemplary embodiments of the device.

According to some exemplary embodiments, during drilling through bone tissue, for example during a drilling state at block 113, the cutting tooth is in a closed position. In some embodiments, in a closed position, the cutting tooth is aligned, for example axially aligned with a longitudinal axis of the device body. In some embodiments, in a closed position, the cutting tooth is positioned within a perimeter defined by the external surface of the device body. Alternatively, in a closed position, the cutting tooth is axially aligned with the body of the device and extends from the perimeter defined by the device body, for example when a width of a distal end of the cutting tooth containing one or more drilling heads is larger than a width of the device body. In some embodiments, during a drilling state, the cutting tooth rotates and the width of the bore is determined by the maximal width of the distal end of the cutting tooth.

According to some exemplary embodiments, during a reaming state at block 115, the cutting tooth is in one or more open positions, for example 2, 3, 4, 5 open positions. Optionally, the one or more open positions are predetermined open positions. In some embodiments, when the cutting tooth is in an open position the cutting tooth is tilted with respect to the body of the device, for example with respect to the longitudinal axis of the body of the device. In some embodiments, each open position corresponds to a selected tilting angle of the cutting tooth. In some embodiments, when the cutting tooth is in one or more open position, at least a portion of the cutting tooth extends sideways from the body of the device. In some embodiments, during reaming the cutting tooth is retracted.

According to some exemplary embodiments, during a retracting state at block 117, the cutting tooth is in a closed position, for example when forming a void in the bone having a narrow opening or entrance point. Alternatively, during a retracting state, the cutting tooth is in one or more open positions, for example when forming a void in the bone having a wide opening or entrance point. In some embodiments, when the cutting tooth is in a closed position, the cutting tooth is axially aligned with a body of the device, for example as described as block 113. In some embodiments, when the cutting tooth is in one or more opening positions, the cutting tooth is tilted relative to the body of the device or relative to the longitudinal axis of the body.

Exemplary General Bone Removal Device

Figure 1C:
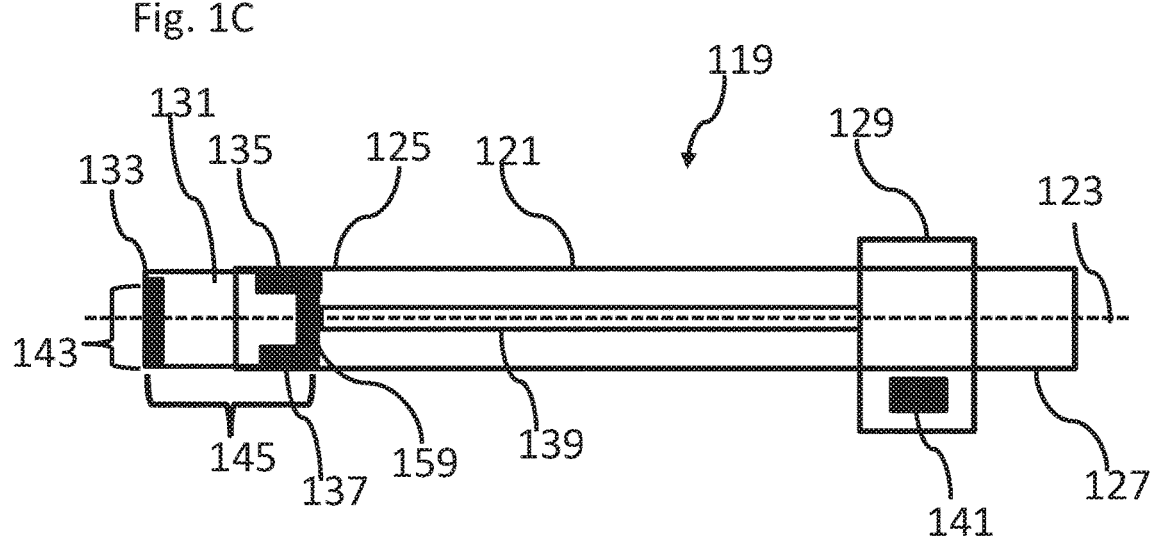
FIGS. 1C-1E are schematic illustrations of a bone removal device, according to some embodiments of the invention.
Figure 1D:
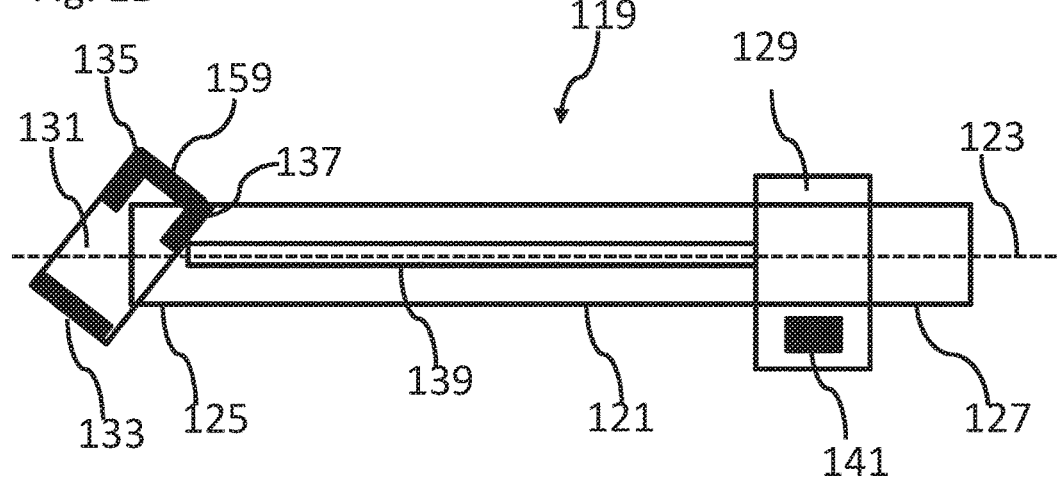

According to some exemplary embodiments, a bone removal device, for example a drilling device is used for both drilling an initial bore in the bone, and for widening the bore, for example to form an opening in the bone. In some embodiments, changing an orientation of a bone borer of the device, for example a tilting angle of the bone borer relative to the device body, moves the device between a drilling state and a widening, for example reaming state. In some embodiments, a tilting angle of a drilling portion, for example a drilling end or a drilling tip of the bone borer changes between a drilling state, when the drilling end is axially aligned with the body of the device, to a reaming state, when the drilling tip is tilted in an angle relative to the device body. Reference is now made to FIGS. 1C and 1D, depicting a bone removal device having a movable bone borer, according to some exemplary embodiments of the invention.

According to some exemplary embodiments, a bone removal device, for example device 119 comprises a body, for example an elongated shaft 121 having a longitudinal axis 123, a distal end 125 and a proximal end 127. As used herein, distal refers to a position close to bone tissue, and proximal refers to a position located away from the bone tissue. In some embodiments, the elongated shaft 121 is hollow. Optionally, the elongated shaft is shaped as a cylinder. In some embodiments, a maximal width of the distal end 125 of the shaft 121 is in a range of 1.5-4.5 mm, for example 1.5-2.5 mm, 2-4 mm, 3-3.5 mm or any intermediate, smaller or larger value.

According to some exemplary embodiments, the device 119 comprises a bone borer, for example cutting tooth 131, mechanically coupled to the distal end 125 of the body 121. In some embodiments, the bone borer comprises one or more distal drilling portions 133, for example a drilling tip. In some embodiments, the one or more distal drilling portions comprises Nirosta, Titanium or any other hardened biocompatible material. In some embodiments, the one or more drilling portions are forwardly facing portions, for example to allow drilling into a bone tissue, when the tooth 131 is axially aligned with the longitudinal axis 123 of the shaft 121. Optionally, the one or more drilling portions are used also for widening of the bone opening, for example during the reaming process. Additionally, the tooth 131 comprises one or more proximal bone cutting edges, for example cutting edges 135 and 137. In some embodiments, the bone cutting edges are located one a periphery of the cutting tooth 131. In some embodiments, the one or more proximal bone cutting edges are angled edges. Optionally, the bone cutting edges are positioned in opposite locations on the periphery of the cutting tooth 131.

According to some exemplary embodiments, a length of the shaft 121, for example an elongated shaft, between a distal end and a proximal end of the shaft, is in a range of 5-40 cm, for example 5-20 cm, 15-30 cm, 25-40 cm or any intermediate, smaller or larger range of values. In some embodiments, a maximal width of the shaft 121 is in a range of 0.5-8 mm, for example 0.5-3 mm, 1-5 mm, 3-8 mm or any intermediate, smaller or larger range of values.

According to some exemplary embodiments, a maximal width 143 of the cutting tooth 131, is equal or larger than the maximal width of the distal end 125 of the shaft 121. In some embodiments, a maximal width 143 is in a range of 1.5-4.5 mm, for example 1.5-2.5 mm, 2-4 mm, 3-3.5 mm or any intermediate, smaller or larger value. In some embodiments, a length 145 of the cutting tooth 131 is in a range of 1-12 mm, for example 1-4 mm, 2-8 mm, 5-12 mm or any intermediate, smaller or larger value. In some embodiments, the length 145 is in a range of 6-9.5 mm, for example 7 mm, 8 mm, 9 mm or any intermediate, smaller or larger range of values. In some embodiments, the cutting tooth 131 is formed from Nirosta, Titanium, Zirconium. Optionally, both the drilling tip 133 and the one or more bone cutting edges, for example cutting edges 135 and 137 are integral portions of the cutting tooth 131.

According to some exemplary embodiments, the bone removal device, for example device 119 comprises a bone borer sideways extending adjuster, for example an adjuster 129 mechanically coupled to the shaft 121, and functionally coupled to the cutting tooth 131. In some embodiments, the adjuster 129 is configured to adjust a sideways extension and/or a tilting angle of the bone borer, for example the cutting tooth 131, optionally by rotation of the adjuster in a selected rotation angle. In some embodiments, each rotation angle corresponds to a selected bone borer extension distance or to a selected bone borer tilting angle, of the cutting tooth 131. Optionally, the adjuster 129 is rotated to predetermined rotation angles which correspond to pre-determined bone borer extension distances or pre-determined bone borer titling angles.

According to some exemplary embodiments, a rotation axis of the adjuster 129 is parallel to the longitudinal axis 123 of the device body. Optionally, the rotation axis of the adjuster is the longitudinal axis 123 of the device body. Alternatively, a rotation axis of the adjuster 129 crosses or is perpendicular to the longitudinal axis of the 123 of the device body. In some embodiments, during drilling and/or reaming, the device 119 rotates around the longitudinal axis 123 of the device body. A potential advantage of rotating the adjuster 129 around an axis that crosses or is perpendicular to the rotation axis of the device 119 is that it may help to avoid rotation of the adjuster as the device rotates during drilling and/or reaming.

According to some exemplary embodiments, the adjuster 129 is functionally coupled to the cutting tooth 131 by a movable coupler 139, for example a pusher element. In some embodiments, a pusher element is used as a puller element. In some embodiments, the movable coupler 139 is coaxially coupled to the elongated shaft 121. Optionally, the movable coupler 139 is positioned within the elongated shaft, for example coaxially coupled within the elongated shaft 121. In some embodiments, the movable coupler 139 is configured to translate a rotation movement of the adjuster 129 into movement of the cutting tooth 131, for example into sideways extension and/or tilting of the cutting tooth 131. In some embodiments, the movable coupler 139 axially moves, for example forwardly advanced towards the cutting tooth 131 or retracted towards the adjuster 129, in response to rotation of the adjuster 129. Alternatively or additionally, the movable coupler 139 rotates clockwise or counterclockwise in response to rotation of the adjuster 129.

According to some exemplary embodiments, the adjuster 129 comprises one or more markings, for example marking 141, configured to provide a human detectable indication, for example a visual indication regarding the rotation state, rotation extent, and/or rotation angle of the adjuster. Alternatively or additionally, the marking 141 is configured to deliver a human detectable indication regarding the opening state, the sideways extension, for example radial extension, and/or the tilting angle of the cutting tooth 131. Optionally, the human detectable indication is provided by an alignment between the marking 141 and an additional marking on the device 119, for example on the body of the device.

According to some exemplary embodiments, for example as shown in FIG. 1D, rotation of the adjuster 129 changes the orientation of the cutting tooth 131 from an axial alignment along the longitudinal axis 123, for example as shown in FIG. 1C, to a tilting orientation, for example to an open position of the cutting tooth, with respect to the longitudinal axis 123 or the body of the device. In some embodiments, in a tilting orientation, the distal drilling portion 133 turn to a first direction while the cutting edges, for example cutting edges 135 and 137 turn to an opposite direction. In some embodiments, in an open position, one or both of the distal drilling portion and the cutting edges 135 and 137 extend at least partly sideways, optionally at different directions. In some embodiments, further turning of the adjuster at the same turning direction or in an opposite direction, increases the extension distance of the cutting edges from the shaft 121.

Figure 1E:
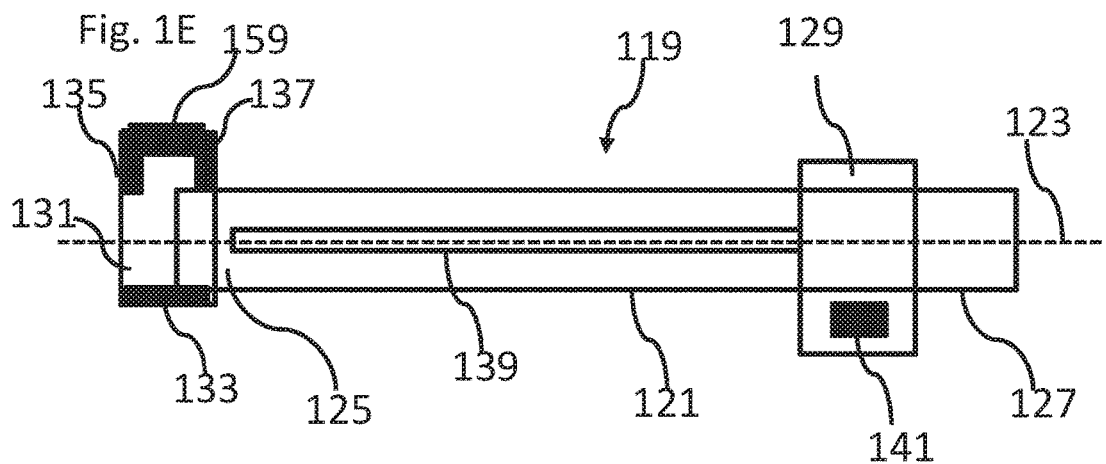
Figure 1K:
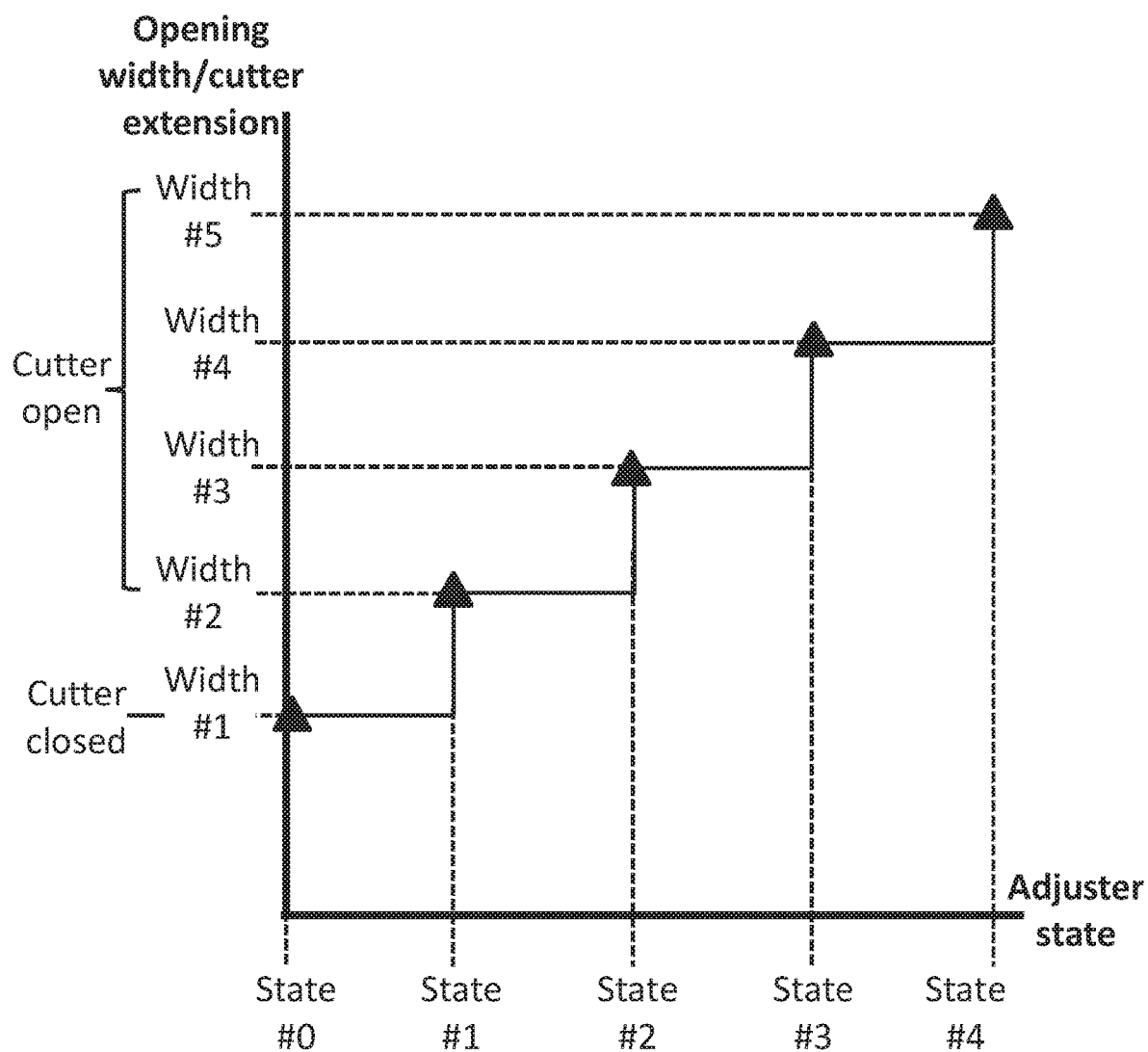
FIG. 1K is a diagram showing changes between predetermined bone borer positions relative to a shaft of a bone removal device, according to some embodiments of the invention.

According to some exemplary embodiments, for example as shown in FIG. 1E, the cutting tooth 131 extends sideways to maximal extension distance of the one or more cutting edges 135 and 137 of up to 10 mm, for example up to 7 mm, up to 5 mm, or any intermediate, smaller or larger value from the shaft 121. In some embodiments, the extension distance of the one or more cutting edges is larger than the extension distance of the distal drilling portion 133. Alternatively, the extension distance of the cutting edges 135 and 137, and the distal drilling portion 133 from the shaft 121 is similar, for example with a deviation of less than 5%, for example less than 3%, less than 2% or any intermediate, smaller or larger deviation percentage. In some embodiments, when the one or more cutting edges, for example cutting edges 135 and 137 are in a maximal extension distance, the cutting tooth 131 is substantially perpendicular to the shaft 121 and/or to the longitudinal axis 123.

According to some exemplary embodiments, for example as shown in FIG. 1F, a bone borer, for example a cutting tooth 161 having a distal end and a proximal end comprises one or more distal drilling portions at the drilling end, for example drilling tip 163, and at least one reaming edge at the proximal end, for example reaming end 165. Optionally, the cutting tooth comprises one or more additional reaming edge 167. In some embodiments, reaming edges 165 and 167 are positioned on opposite sides of the cutting tooth 165. Optionally, the reaming edges 165 and 167 are converging to a single point. In some embodiments, for example as shown in FIG. 1F, the cutting tooth 161 comprises an additional reaming edge at the distal end of the cutting tooth 161, for example reaming edge 169 connecting the two reaming edges 165 and 167. Alternatively, the reaming edge 169 is connected to either reaming edge 165 or reaming edge 167.

According to some exemplary embodiments, for example as shown in FIG. 1G, a bone borer, for example a cutting tooth 171 having a distal end and a proximal end, comprises one or more distal drilling portions at the drilling end, for example drilling tip 173, and at least one reaming edge at the proximal end, for example reaming edge 175. In some embodiments, the cutting tooth, for example cutting tooth 171 comprises an additional reaming edge 177 at the proximal end of the cutting tooth 171. In some embodiments, reaming edges 175 and 177 converge to a single point, which is optionally a contacting point between the two reaming edges, for example contacting point 179.

According to some exemplary embodiments, the reaming edges located at, or near, a proximal end of the cutting tooth form a reamer portion of the cutting tooth. In some embodiments, when the cutting tooth is tilted relative to the shaft or body of the device, different reaming edges are placed in contact with the bone as the device is retracted.

Exemplary Bone Fragments Removal Opening

According to some exemplary embodiments, when the cutting tooth is in an open position, at least one portion of the cutting tooth extent sideways from the body of the bone removal device, and is placed in contact with bone tissue. In some embodiments, during a reaming stage, the cutting tooth, which is pivotally connected to the body, rotates and chopped bone fragments accumulate. In some embodiments, in order to remove the bone fragments from the cutting site, an opening is formed in the body of the bone removal device. Reference is now made to FIGS. 1H-1J, depicting a side-to-side, crossing window, according to some exemplary embodiments of the invention.

According to some exemplary embodiments, for example as shown in FIG. 1H, a body of a bone removal device, for example an elongated shaft 147 comprises a distal end 149 and a proximal end 151. In some embodiments, the shaft 149 comprises a side-to-side, crossing opening, for example opening 153. In some embodiments, the opening 153 is formed by two or more opposite cut-outs in the distal end 149 of the shaft 147.

According to some exemplary embodiments, for example as shown in FIG. 1I, a bone borer, for example cutting tooth 155 is pivotally coupled to the distal end 149 of the shaft 147, at least partly within the opening 153. In some embodiments, when the cutting tooth is in a closed position, for example during drilling, the opening, for example the opening volume, is at least 90% closed, for example at least 90%, at least 95%, at least 98% or any intermediate, smaller or larger percentage value of the opening is closed.

According to some exemplary embodiments, for example as shown in FIG. 1J, in an open position, the cutting tooth 155 tilts, and at least a portion of the cutting tooth extends sideways from the shaft 147. In some embodiments, the tilting of the cutting tooth 155 opens the opening 153 is at least 20%, for example at least 25%, at least 40%, at least 50% or any intermediate, smaller or larger value. In some embodiments, when the opening 153 is opened bone fragments chopped at one side of the shaft 147, for example during reaming, can cross through shaft to the other side of the shaft 147. Alternatively or additionally, when the shaft is a hollow shaft, bone fragments chopped by the cutting tooth, for example during reaming, can enter through the opening into the inner lumen of the hollow shaft.

Exemplary Selecting Pre-Determined Opening Widths

According to some exemplary embodiments, during a drilling process, for example to form an initial bore, the width of the bore is based on the width of the drill or one or more drilling portions. In some embodiments, when widening, for example reaming the initial formed bore to a desired opening width, a pre-determined state of a bone borer sideways extending adjuster is selected, which is associated with the desired bone opening width. In some embodiments, the adjuster rotates incrementally, when moving between the pre-determined states.

Reference is now made to FIG. 1I, depicting selection of adjuster state which correspond with pre-determined bone opening widths or bone borer extension distances, according to some exemplary embodiments of the invention.

According to some exemplary embodiments, during drilling, for example to form an initial bore, the bone borer is closed. In some embodiments, during drilling the bone borer is located within a perimeter defined by the external surface of the shaft. In some embodiments, when the bone borer is closed, the adjuster is at a first state, for example state #0. In some embodiments, when the adjuster is at a first state, rotation of the bone borer forms a bone opening having a width in a range of 3-4 mm, for example 3 mm, 3.5 mm, 4 mm or any intermediate, smaller or larger value.

According to some exemplary embodiments, when moving the adjuster to a second pre-determined state, for example by turning the adjuster to state #1, the bone borer is opened to a pre-determine extension distance, which is associated with a pre-determined width #2 of the bone opening. In some embodiments, when the adjuster is at a second state (state #1), rotation of the bone borer forms a bone opening having width #2 which is in a range of 5-7 mm, for example 5 mm, 5.5 mm, 6 mm or any intermediate, smaller or larger value.

According to some exemplary embodiments, when moving the adjuster to a third predetermined state, for example by turning the adjuster to state #2, the bone borer is opened to a pre-determined extension distance. In some embodiments, when the adjuster is at the third state (state #2), rotation of the bone borer forms a bone opening having width #3 which is in a range of 6-8 mm, for example, 6 mm, 7 mm, 8 mm or any intermediate, smaller or larger value.

According to some exemplary embodiments, when moving the adjuster to a fourth pre-determined state, for example by turning the adjuster to state #3, the bone borer is opened to a pre-determined extension distance. In some embodiments, when the adjuster is at state #3, rotation of the bone borer forms a bone opening with a width #4, which is in a range of 7-9 mm, for example 7.5 mm, 8 mm, 8.5 mm or any intermediate, smaller or larger value.

According to some exemplary embodiments, when moving the adjuster to the fifth pre-determined state, for example by turning the adjuster to state #4, the bone borer is opened to a pre-determined extension distance. In some embodiments, when the adjuster is at state #4, rotation of the bone borer forms a bone opening with a width #5, which is in a range of 10-12 mm, for example 10 mm, 11 mm, 12 mm or any intermediate, smaller or larger value.

According to some exemplary embodiments, in the last pre-determined state of the adjuster, the bone borer moves to be substantially perpendicular to the shaft of the device, for example as shown in FIG. 1E. In some embodiments, when the bone borer is substantially perpendicular to the shaft of the device, the bone borer extends to the largest distance, which allows, for example to form, when the bone borer is rotated, a bone opening with a width of up to 15 mm, for example up to 14 mm, up to 13 mm, up to 12 mm or any intermediate smaller or larger width.

Exemplary Bone Removal Devices and Portions Thereof.

A bone removal device, for example a drilling device is disclosed herein, which is particularly useful for drilling a bore within a bone of a patient, whereas the diameter of the bore can be adjusted by the user.

Figure 1L:
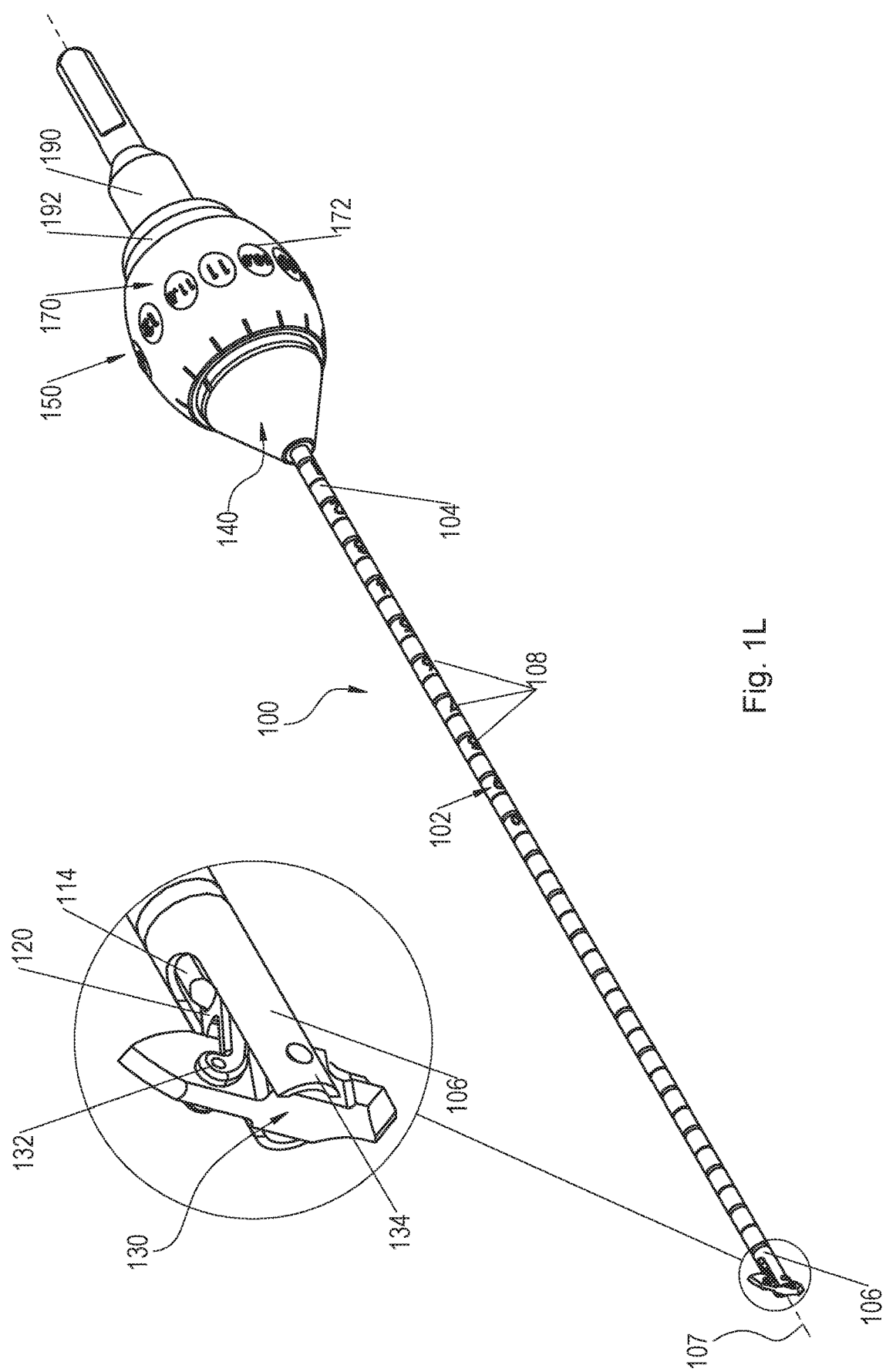

Reference is now made to FIGS. 1L & 1M, which are respective simplified pictorial illustrations of an assembled view and an exploded view of a drilling device, constructed and operative in accordance with some exemplary embodiments of the present invention.

According to some exemplary embodiments, a drilling device, for example drilling device 100 is seen in FIGS. 1L & 1M. In some embodiments, for example as seen in FIGS. 1L & 1M, the drilling device 100 includes a shaft element 102 having a proximal end 104 and a distal end 106. In some embodiments, the shaft 102 is being arranged along a longitudinal axis 107. In some embodiments, the shaft element 102 includes a visual scale marking, for example visual scale markings 108, on the outer surface thereof, for example to enable identifying the depth of penetration of the drilling device 100 into the bone of the patient.

According to some exemplary embodiments, for example as shown in FIG. 1L, the device 100 comprises a pusher element, for example pusher element 110. In some embodiments, the pusher element 110 is adapted to be coaxially received within shaft element 102 and also defines a proximal end 112 and a distal end 114.

According to some exemplary embodiments, the device 100 comprises a crank, for example crank 120 pivotably connected to both the distal end 106 of the shaft element 102 and the distal end 114 of the pusher element 110, for example by means of a pivoting pin 122. In some embodiments, the crank 120 is in turn pivotably connected to a bone borer, for example cutting tooth 130, for example by means of a pivoting pin 132. In some embodiments, the cutting tooth is additionally pivotably connected to the distal end 106 of the shaft element 102, for example by means of an additional pivoting pin 134.

According to some exemplary embodiments, the proximal end 104 of the shaft element 102 is fixedly connected to a cover element 140. In some embodiments, the proximal end 104 of the shaft element 102 is moveably connected to a pusher element displacer, for example pusher element displacing mechanism 150.

According to some exemplary embodiments, the pusher element displacing mechanism 150 comprises a guiding element, for example guiding element 160 which is fixedly attached to the proximal end 112 of the pusher element 110, and is optionally coaxially arranged therewith. In some embodiments, the guiding element 160 is adapted to be partially received within cover element 140. In some embodiments, the guiding element 160 comprises a plunger enclosing socket 162, which is adapted to receive therein a plunger 164.

According to some exemplary embodiments, the device 100 comprises an adjuster, for example an adjusting element, for example an adjusting element 170, coaxially arranged with the guiding element 160 and/or at least partially surrounds the guiding element 160. In some embodiments, the adjusting element 170 has visual scale markings 172 on the circumference thereof, for example to indicate the desired bore diameter to be formed within the bone of the patient.

According to some exemplary embodiments, the device 100 comprises a stopper, for example stopper element 180, configured to be supported against a portion of the adjusting element 170 and optionally being held in place by means of nut 182. In some embodiments, the nut 182 is biased distally under the force of spring 184.

According to some exemplary embodiments, for example as seen in FIG. 1M, the device comprises a spring, for example spring 184 coaxially arranged with guiding element 160, and is optionally configured to be received within a socket formed in the rotating element 190, which is arranged, for example, along the mutual longitudinal axis 107. In some embodiments, a rear cover 192 is adapted to be mounted onto a portion of the rotating element 190 and is optionally partially received within adjusting element 170.

According to some exemplary embodiments, the rotating element 190 is adapted to be attached to a power tool imparting rotational movement thereto.

According to some exemplary embodiments, that drilling device 100 provides for creating undercut bores of various diameters, for example by opening cutting tooth 130 of the drilling device 100 to a different radial extent, for example as is described in detail hereinbelow. In some embodiments, the adjusting element 170 is rotatably by the user and is adapted to cooperate with the guiding element 160 and with the pusher element 110, for example to allow opening of the cutting tooth 130 to various radial extents and thus optionally forming various diameters of undercut bores in the bone of the patient.

Exemplary Cutting Tooth

Figure 19C:
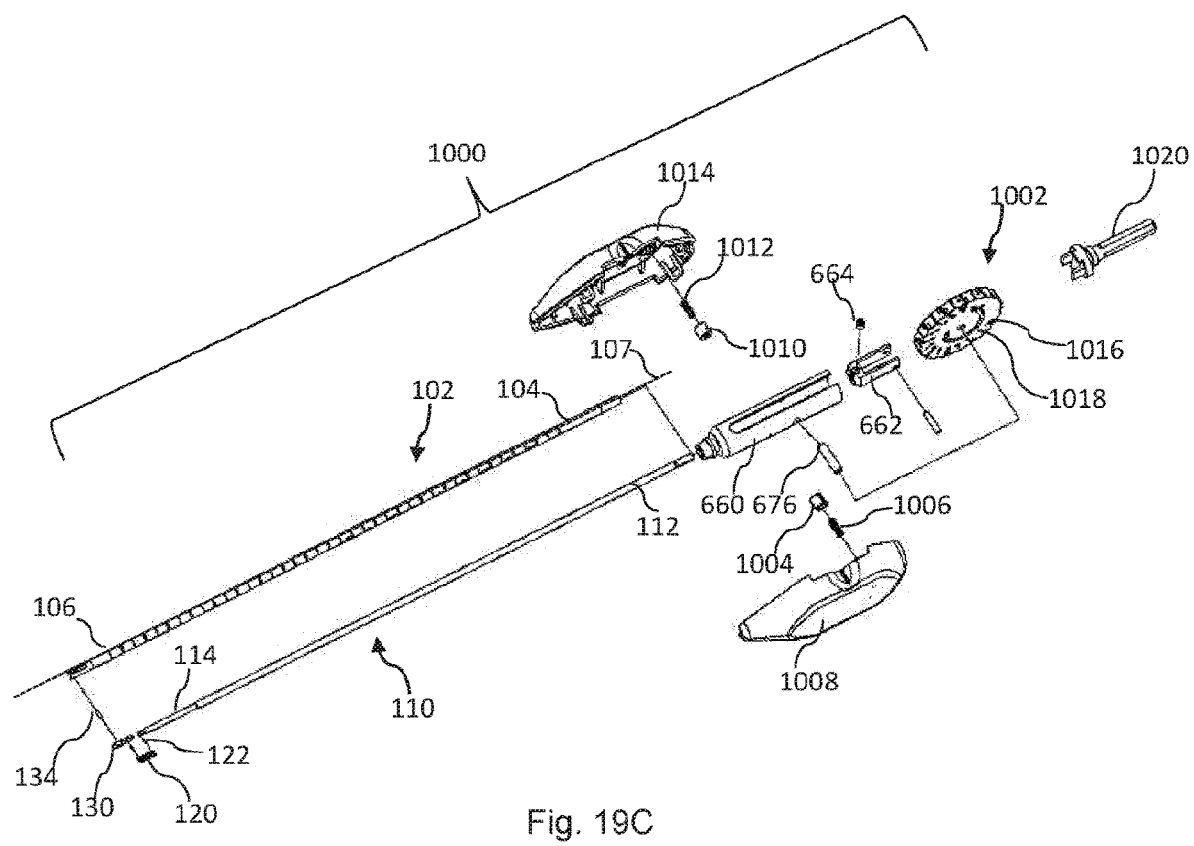
FIG. 19C is a respective simplified pictorial illustration of an exploded view of a drilling device having one or more plungers, constructed and operative according to some embodiments of the invention.

Reference is now made to FIGS. 2A-2C, which are a respective simplified pictorial illustration and two different plan views of a cutting tooth, for example the cutting tooth 130, forming part of the drilling device 100 of FIGS. 1L & 1M, the drilling device 600 of FIGS. 19A & 19B, the drilling device 1000 of FIG. 19C, and according to some exemplary embodiments of the invention.

According to some exemplary embodiments, a cutting tooth, for example cutting tooth 130 is integrally made generally flat element, for example from a bio-compatible metal and is optionally arranged along longitudinal axis 201. In some embodiments, for example as seen in FIGS. 2A-2C, the cutting tooth 130 has a drilling end 200 at the distal end thereof and a reaming end 202 at the proximal end thereof. In some embodiments, the drilling end 200 preferably includes a plurality of facets 204, which optionally facilitate effective drilling of the bone of the patient while advancing in a distal direction. In some embodiments, the reaming end 202 preferably has two cutting edges 206, which are generally mutually facing opposite directions. In some embodiments, at least one of these cutting edges 206 is adapted to facilitate reaming of the bore resulting from drilling of the bone, for example, while advancing the drilling device 100 in a distal direction. In some embodiments, reaming of the bore is provided for example, for enlarging the diameter of the bore drilled within the bone, while optionally retracting the drilling device 100 in a proximal direction.

According to some exemplary embodiments, an aperture 210 is formed in cutting tooth 130 and optionally extends along axis 212, which is generally perpendicular to longitudinal axis 201. In some embodiments, the aperture 210 serves as a seat for the pivoting axis of the cutting tooth 130. In some embodiments, a pivot, for example pivoting pin 134, shown in FIG. 1M, serves as the pivoting axis of the cutting tooth 130. In some embodiments, the aperture 210 is disposed generally closer to the drilling end 200 than to the reaming end 202.

According to some exemplary embodiments, an additional aperture 212 is formed in cutting tooth 130, which is adapted for receiving the pivoting pin 132, shown in FIG. 1M, and configured for pivotable connection of the cutting tooth 130 to the crank 120.

Exemplary Crank

Figure 3B:
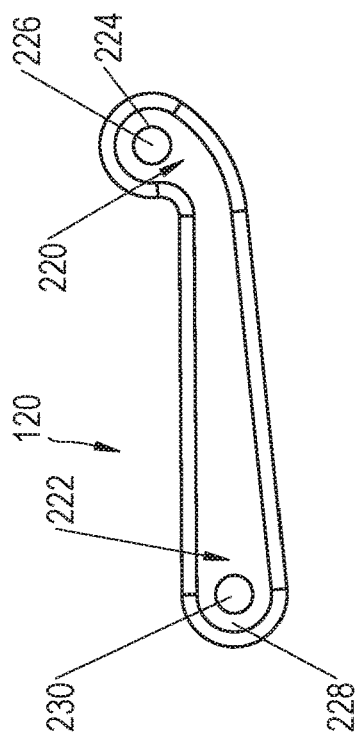
FIGS. 3A-3C are a respective simplified pictorial illustration and two different plan views of a crank, forming part of the drilling device of FIGS. 1L & 1M, and according to some embodiments of the invention.
Figure 3C:
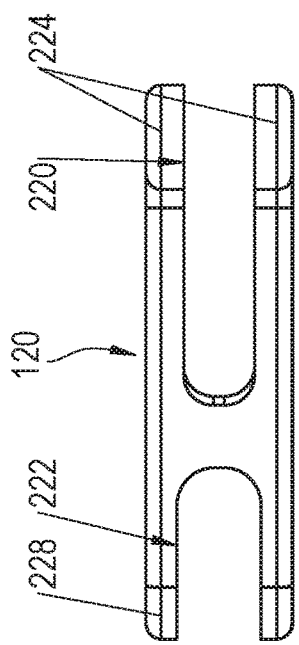
Figure 3A:
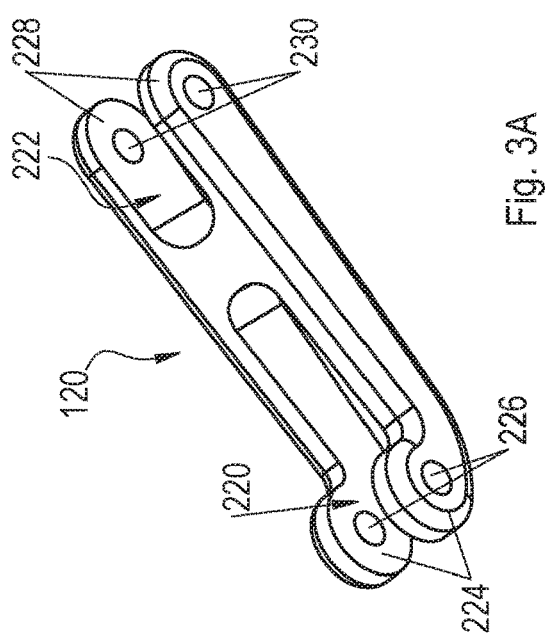

Reference is now made to FIGS. 3A-3C, which are a respective simplified pictorial illustration and two different plan views of a crank, for example the crank 120, forming part of the drilling device 100 of FIGS. 1L & 1M, the drilling device 600 of FIGS. 19A & 19B, the drilling device 1000 of FIG. 19C, and according to some exemplary embodiments of the invention.

According to some exemplary embodiments, the crank 120 is an integrally made element, for example made of a bio-compatible metal. In some embodiments, the crank 120 has a distal end 220 and a proximal end 222. In some embodiments, the distal end 220 has a pair of mutually spaced apart hooks 224. In some embodiments, each of the hooks 224 has an aperture 226 therein. In some embodiments, the proximal end 222 also comprises a pair of mutually spaced apart hooks 228. In some embodiments, each of the hooks comprises an aperture 230 therein.

According to some exemplary embodiments, the apertures 226 are configured for receiving pivoting pin 132, for example as shown in FIG. 1M, for connection thereof with the cutting tooth 130. In some embodiments, the apertures 230 are configured for receiving a pivot, for example the pivoting pin 122, as shown in FIG. 1M, for example, for connection thereof with the pusher element 110 and the shaft element 102.

Exemplary Pusher

Reference is now made to FIGS. 4A-4C, which are a respective simplified pictorial illustration and two different plan views of a pusher element, for example the pusher element 110, forming part of the drilling device 100 of FIGS. 1L & 1M, the drilling device 600 of FIGS. 19A & 19B, the drilling device 1000 of FIG. 19C, and according to some exemplary embodiments of the invention.

According to some exemplary embodiments, a pusher, for example pusher element 110 is integrally made cylindrical element, optionally made of a bio-compatible metal. In some embodiments, the pusher element 110 is arranged along longitudinal axis 107. In some embodiments, the pusher element 110 comprises a proximal end 112, a distal end 114 and optionally a flange 240. In some embodiments, the flange 240 is distally extending from distal end 114 along longitudinal axis 107. In some embodiments, an aperture 242 is formed through flange 240 and extends along an axis, which optionally is generally perpendicular to axis 107. In some embodiments, aperture 242 is configured to receive the pivoting pin 122, for example, for connection of the pusher element 110 with crank 120, and thus optionally with the cutting tooth 130.

Exemplary Shaft

Reference is now made to FIGS. 5A-5D, which are a respective simplified pictorial illustration and three different plan views of a shaft element, for example the shaft element 102, forming part of the drilling device 100 of FIGS. 1L & 1M, the drilling device 600 of FIGS. 19A & 19B, the drilling device 1000 of FIG. 19C, and according to some embodiments of the invention.

According to some exemplary embodiments, a shaft, for example a shaft element 102 is an integrally made hollow cylindrical element, optionally made of a bio-compatible metal and arranged along longitudinal axis 107. In some embodiments, the shaft element 102 has a proximal end 104, and distal end 106, for example as mentioned above. In some embodiments, the shaft element 102 includes visual scale markings 108 on the outer surface thereof, for example, to enable identifying the depth of penetration of the drilling device 100 into the bone of the patient.

According to some exemplary embodiments, the shaft element 102 has a relatively long first cut-out 250 disposed at the distal end 106 thereof, and optionally extends from the distal end 106 proximally. In some embodiments, a second cut-out 252, which is optionally shorter than the first cut-out 250, is located generally diametrically opposite to the first cut-out 250. In some embodiments, a pair of apertures 254 are formed at the distal end 106 of shaft element 102, disposed between the cut-outs 250 and 252. In some embodiments, the pair of apertures 254 are arranged along an axis that is generally perpendicular to longitudinal axis 107. In some embodiments, the apertures 254 are adapted for receiving a pivot, for example a pivoting pin 122, as shown in FIG. 1M, for example, for connection of the crank 120 to the pusher element 110 and to the shaft element 102.

According to some exemplary embodiments, a distal end of the shaft, for example distal end 106 of the shaft 102, comprises a separate distal portion having an opening shaped and sized to position a movable bone borer within said opening. In some embodiments, the separate distal portion is fixedly coupled to the said shaft by welding, adhesion and/or soldering. In some embodiments, the separate distal portion is formed from a material which is different from the material used to form the shaft. In some embodiments, the distal portion is formed from a hardened material, for example to allow increased resistance of the distal portion against twisting forces. In some embodiments, the separate distal portion is formed from different Nirosta, Titanium, Zarconium, other medical grade metals.

Exemplary Cover

Reference is now made to FIGS. 6A-6C, which are a respective simplified pictorial illustration, a plan view and a sectional view of a cover element, for example the cover element 140, forming part of the drilling device 100 of FIGS. 1L & 1M, the sectional view being taken along lines C-C in FIG. 6B, and according to some exemplary embodiments of the invention.

According to some exemplary embodiments, a cover, for example a cover element 140 is an integrally made element, which is optionally made of plastic. In some embodiments, the cover 140 is arranged along longitudinal axis 107. In some embodiments, the cover element 140 has a distal generally conical portion 270 and a proximal generally cylindrical portion 272. In some embodiments, a marking 274 is formed on the outer surface of the cylindrical portion 272. In some embodiments, the marking 274 is adapted to cooperate with scale markings 172 formed on the adjusting element 170.

According to some exemplary embodiments, for example as seen in FIG. 6C, a bore, for example a bore 280 is formed in conical portion 270 and extends along longitudinal axis 107, for example, for receiving the proximal end 112 of the pusher element 110. In some embodiments, bore 280 has a first diameter sized to the shaft.

According to some exemplary embodiments, A bore 282 is formed proximally to bore 280, optionally within the cylindrical portion 272 and communicating with bore 280. In some embodiments, the bore 282 has a second diameter. In some embodiments, the second diameter is generally greater than the first diameter. In some embodiments, the bore 282 extends along longitudinal axis 107 and is adapted to partially receive the guiding element 160.

According to some exemplary embodiments, an additional bore 284 is disposed laterally to bore 282. In some embodiments, the bore 284 extends partially along the longitudinal extent of bore 282 and along an axis, which is generally parallel to axis 107. In some embodiments, bore 284 is configured to communicate with bore 282 and is optionally adapted for receiving the plunger enclosing socket 162 of the guiding element 160.

Exemplary Guiding Element

Figure 7A:
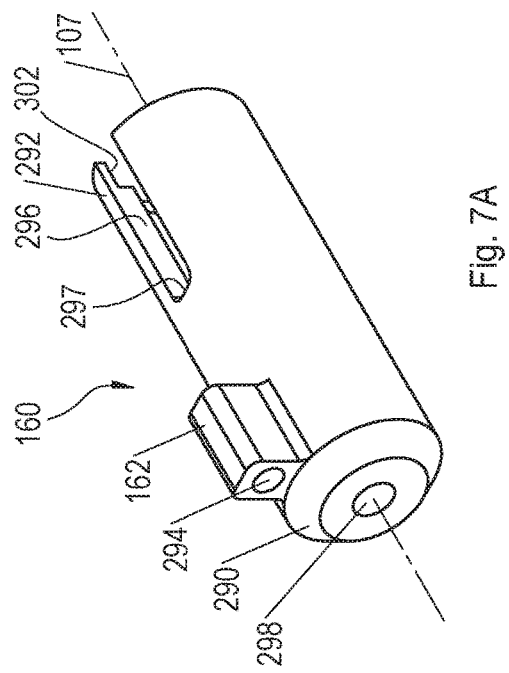
FIGS. 7A-7C are a respective simplified pictorial illustration, a plan view and a sectional view of a guiding element, forming part of the drilling device of FIGS. 1L & 1M, the sectional view being taken along lines C-C in FIG. 7B, and according to some embodiments of the invention.
Figure 7C:
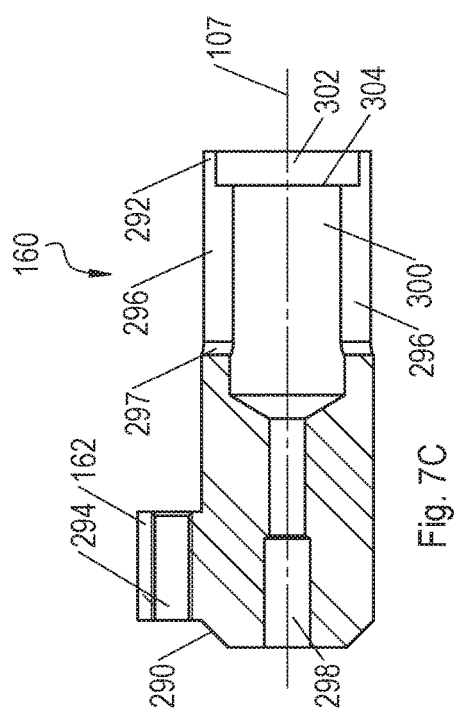
Figure 7B:
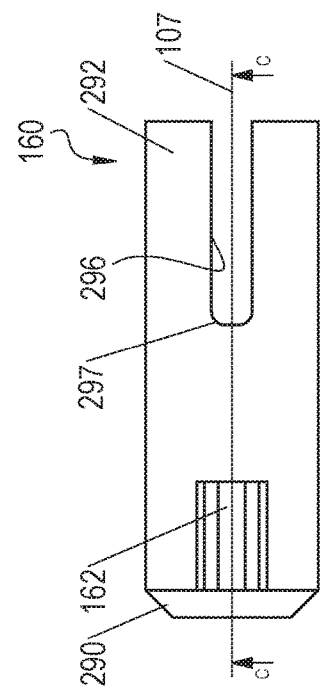

Reference is now made to FIGS. 7A-7C, which are a respective simplified pictorial illustration, a plan view and a sectional view of a guiding element, for example the guiding element 160, forming part of the drilling device 100 of FIGS. 1L & 1M, the sectional view being taken along lines C-C in FIG. 7B, and according to some exemplary embodiments of the invention.

According to some exemplary embodiments, a guiding element, for example guiding element 160 is an integrally made element, which is optionally made of metal and arranged along longitudinal axis 107.

In some embodiments, the guiding element 160 is a generally cylindrical element having a distal end 290, a proximal end 292 and optionally a plunger enclosing socket 162. In some embodiments, the plunger enclosing socket 162 is formed on the circumference of the guiding element 160, optionally adjacent the distal end 290 thereof.

In some embodiments, the plunger enclosing socket 162 defines a through bore 294, which is optionally adapted to fixedly hold the plunger 164 therewithin, for example, for operative cooperation with the adjusting element 170.

In some embodiments, for example as seen in FIG. 7C, the guiding element 160 has two diametrically opposed guiding cut-outs 296 extending distally from the proximal end 292 thereof. In some embodiments, the two diametrically opposed guiding cut-outs 296 are adapted for receiving a portion of the stopper element 180. In some embodiments, at least one of the cut-out terminates at an arcuate end surface 297.

According to some exemplary embodiments, for example as seen in FIG. 7C, a bore 298 extends proximally from the distal end 290 of the guiding element 160. In some embodiments, the bore 298 extends along longitudinal axis 107. In some embodiments, the bore 298 has a first diameter and is optionally adapted for receiving a portion of the proximal end 112 of the pusher element 110. In some embodiments, a bore 300 is formed proximally to bore 298 and communicates therewith. In some embodiments, the bore 300 extends along longitudinal axis 107 from bore 298 proximally toward the proximal end 292 of the guiding element 160 and has a second diameter, which is optionally greater than the first diameter. In some embodiments, the second diameter of the bore 300 is adapted for receiving a portion of the rotating element 190. In some embodiments, a wider bore portion 302 is formed at the proximal end of bore 300, which optionally defines a proximally facing shoulder 304.

Exemplary Adjusting Element

Reference is now made to FIGS. 8A-8E, which are a respective simplified pictorial illustration, three different plan views and a sectional view of an adjusting element, for example the adjusting element 170, forming part of the drilling device 100 of FIGS. 1L & 1M, the sectional view being taken along lines E-E in FIG. 8C, and according to some exemplary embodiments of the invention.

According to some exemplary embodiments, an adjuster, for example an adjusting element, for example adjusting element 170 is an integrally made element, which is optionally made of plastic and arranged along longitudinal axis 107.

In some embodiments, the adjusting element 170 is a generally cylindrical or a barrel-shaped element having a distal end 320 and a proximal end 322. In some embodiments, the adjusting element has an outer gripping surface 324 having the scale markings 172 formed thereon, for example to indicate the desired diameter of the resulting bore. In some embodiments, there are also scale marks 326 adjacent the distal end 320 of the adjusting element 170, which are optionally adapted in cooperation with the marking 274 of the cover element 140, for example to indicate to the user what is the selected diameter.

According to some exemplary embodiments, a varying diameter bore, for example varying diameter bore 330 is formed along adjusting element 170 and optionally extends along longitudinal axis 107. In some embodiments, the bore 330 has a distal bore portion 332, a central bore portion 334 and a proximal bore portion 336.

In some embodiments, the proximal bore portion 336 and the distal bore portion 332 both have substantially similar first diameter and the central bore portion 334 has optionally a second diameter, which is generally smaller than the first diameter.

In some embodiments, the proximal bore portion 336 defines a proximally facing circumferential shoulder 340, optionally adapted for engagement with the stopper element 180. In some embodiments, the distal bore portion 332 defines distally facing spiral adjusting path 350. In some embodiments, the spiral adjusting path 350 includes a plurality of steps 352, each successive step has a different height and each successive step 352 is optionally spaced a different distance from the distal end 320 of the adjusting element 170. In some embodiments, the adjusting path 350 includes the first step 352 which is closest to the distal end 320 of the adjusting element 170, and optionally each successive step 352 is incrementally further away from the distal end 320. In some embodiments, the range of the height difference between any of the successive steps is in a range of 0.5 mm-5 mm, for example 0.5 mm-3 mm, 2 mm-4 mm, 2 mm-5 mm or any intermediate, smaller or larger range of values. Alternatively, the range of the height difference between each of the steps 352 is smaller or larger, in accordance with the required medical application.

In some embodiments, for example as seen in FIGS. 8A and 8C each of the steps 352 includes a recess 354, optionally adapted for engagement with a portion of the plunger 164, shown in FIG. 1M.

Exemplary Stopper Element

Figure 9B:
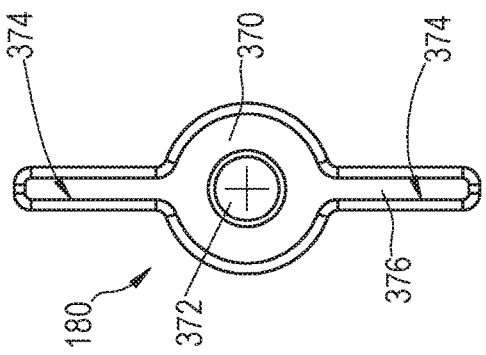
FIGS. 9A-9B are a respective simplified pictorial illustration and a plan view of a stopper element, forming part of the drilling device of FIGS. 1L & 1M, and according to some embodiments of the invention.
Figure 9A:
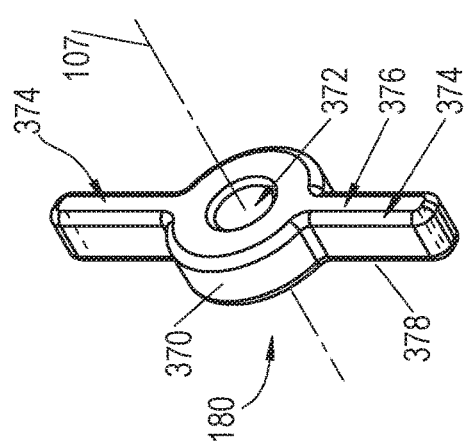

Reference is now made to FIGS. 9A-9B, which are a respective simplified pictorial illustration and a plan view of a stopper element, for example the stopper element 180, forming part of the drilling device 100 of FIGS. 1L & 1M, and according to some exemplary embodiments of the invention.

According to some exemplary embodiments, a stopper element, for example stopper element 180 is an integrally made flat element, which is optionally made of plastic and arranged along longitudinal axis 107.

According to some exemplary embodiments, the stopper element 180 has a central generally annular portion 370, having a bore 372 formed therethrough and optionally extending along longitudinal axis 107. In some embodiments, two longitudinal arms 374 extend radially from the annular portion 370. In some embodiments, the stopper element defines a distally facing surface 376 and a proximally facing surface 378.

Exemplary Rotating Element

Figure 10A:
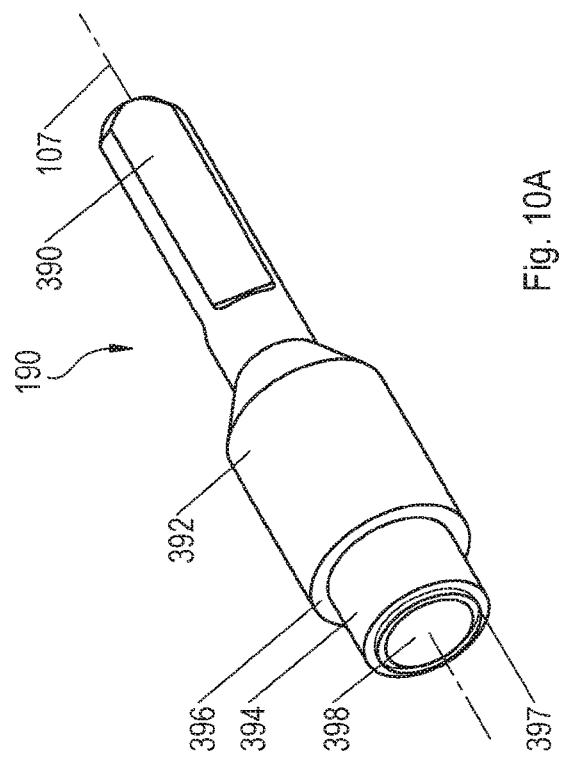
FIGS. 10A-10C are a respective simplified pictorial illustration, a plan view and a sectional view of a rotating element, forming part of the drilling device of FIGS. 1L & 1M, the sectional view being taken along lines C-C in FIG. 10B, and according to some embodiments of the invention.
Figure 10B:
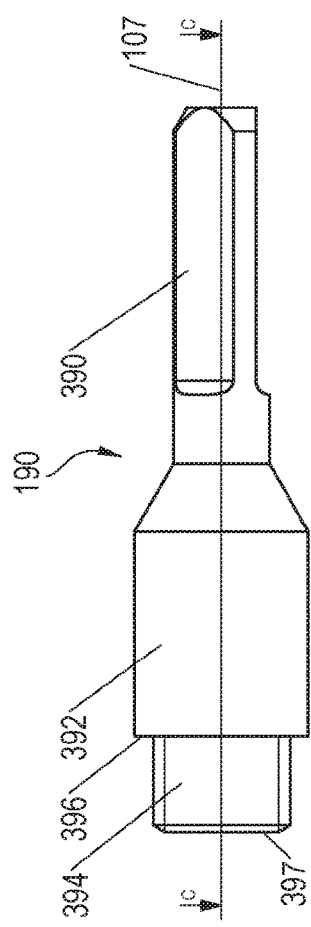
Figure 10C:
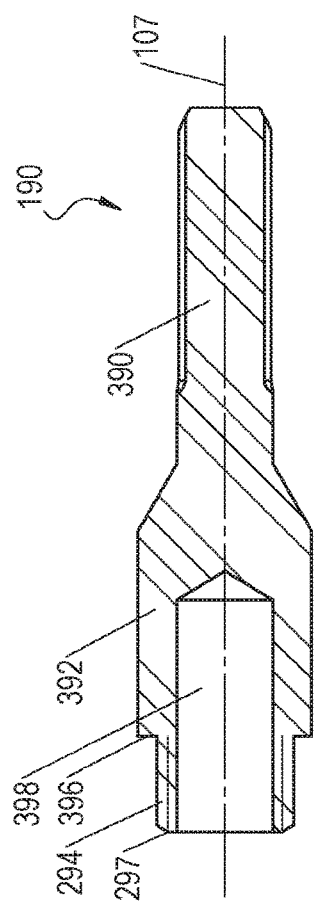

Reference is additionally made to FIGS. 10A-10C, which are a respective simplified pictorial illustration, a plan view and a sectional view of the rotating element 190, forming part of the drilling device 100 of FIGS. 1L & 1M, the sectional view being taken along lines C-C in FIG. 10B, according to some embodiments of the invention.

According to some exemplary embodiments, a rotating element, for example rotating element 190 is an integrally made element, which is optionally made of and arranged along longitudinal axis 107.

In some embodiments, the rotating element 190 has a proximal portion 390 of a first diameter, optionally adapted to be connected to a power tool, for example, for imparting rotational movement from the power tool to the drilling device 100. In some embodiments, the rotating element 190 further has a central portion 392 of a second diameter, which is substantially larger than the first diameter and optionally a distal portion 394 of a third diameter, which is substantially smaller of the second diameter and optionally larger than the first diameter. In some embodiments, the distal portion 394 is adapted to be fixedly connected to the guiding element 160, for example in order to enable impartation of rotation from the power tool to the drilling device 100.

According to some exemplary embodiments, a distally facing shoulder 396 is defined between the central portion 392 and the distal portion 394. In some embodiments, the distal end portion further defines a distally facing end surface 397.

In some embodiments, for example as seen in FIG. 10C, a longitudinal blind bore 398 is formed in rotating element 190 and extends longitudinally along axis 107 through the distal portion 394 and through at least a portion of the central portion 392. In some embodiments, the bore 398 is adapted for accommodating spring 184 therewithin, for example as shown in FIG. 1M.

Exemplary Drilling Device

Reference is now made to FIGS. 11A-11C, which are respective simplified two different plan views and a sectional view of a sub-assembly of a drilling device, for example the drilling device 100 of FIGS. 1L & 1M not showing the adjusting element 170 of FIGS. 8A-8E, the sectional view being taken along lines C-C in FIG. 11B, and according to some exemplary embodiments of the invention.

According to some exemplary embodiments, for example as seen in FIGS. 11A-11C, the cutting tooth 130 is in its closed operative orientation.

According to some exemplary embodiments, the guiding element 160 is partially received within cover element 140, optionally such that the distal end 290 of the guiding element 160 is seated within bore 282 of cover element 140. In some embodiments, a plunger enclosing socket 162 of the guiding element 160 is seated within bore 284 of the cover element 140. In some embodiments, the proximal end 292 of the guiding element 160 is fixedly connected to the distal portion 394 of the rotating element and the rear cover 192 is optionally fixedly coupled to the central portion 392 of the rotating element 190. In some embodiments, a shaft element 102 is fixedly connected to the cover element 140, optionally such that the proximal end 104 of the shaft element 102 is inserted into bore 280 of the cover element 140. In some embodiments, the pusher element 110 is partially enclosed within the shaft element 102 and optionally disposed such that the proximal end 112 of the pusher element extends proximally with respect to the proximal end 104 of the shaft element 102.

According to some exemplary embodiments, for example as seen in FIG. 11C, the stopper element 180 is fixedly connected to the pusher element 110 and the pusher element optionally extends through bore 372 of the stopper element 180. In some embodiments, the stopper element 180 is threaded onto the pusher element 110 (not shown) and fixedly mounted thereon by means of nut 184, which optionally engages proximally facing surface 378 of the stopper element 180. In some embodiments, spring 184 is seated within bore 398 of the rotating element 190 and is configured to bias the stopper element 180 distally. In some embodiments, the distal end 106 of the shaft and the distal end 114 of the pusher element 110 are connected with the crank 120, for example by means of pivoting pin 122. In some embodiments, the crank 120 is pivotably connected to the cutting tooth 130, for example by means of pivoting pin 132. In some embodiments, the cutting tooth 130 is pivotably connected to the distal end 106 of the shaft element 102, which optionally has two cut-outs 250 and 252, which enable, for example, radial extension of the cutting tooth 130.

According to some exemplary embodiments, the stopper element 180 and the pusher element 110 are fixedly attached and thus are moveable together in some embodiments, the stopper element 180 and the pusher element 110 are together slidably axially moveable with respect to guiding element 160. Optionally, the longitudinal arms 374 of the stopper element 180 are slidably moveable along cut-outs 296 of the guiding element. In some embodiments, upon engagement of the longitudinal arms 374 with end surfaces 297 of cut-outs 296, the cutting tooth 130 is disposed in its fully open operative orientation.

According to some exemplary embodiments, the cutting tooth 130 is the distalmost component of the drilling device 100, it extends distally with respect to the distal end 106 of the shaft element 102. In some embodiments, the cutting tooth 130 serves as the drilling tip.

Reference is now made to FIGS. 12A & 12B, which are respective plan view and sectional view illustrations of a drilling device, for example the drilling device 100 of FIGS. 1L & 1M shown in a closed operative orientation, before insertion into a bone of a patient, sectional view is taken along lines B-B in FIG. 12A, and according to some exemplary embodiments of the invention.

According to some exemplary embodiments, FIGS. 12A & 12B show the drilling device in a closed operative orientation, where the cutting tooth 130 does not radially extend from the outer surface of the shaft element 102 and is optionally adapted in this orientation for drilling an initial bore within bone 500 of the patient, for example using drilling end 200, optionally while advancing the drilling device 100 in a distal direction through bone 500 of the patient.

In some embodiments, all spatial relationships between the different components of the drilling device 100 remain substantially the same as described with reference to FIGS. 11A-11C, other than the following relationships:

In some embodiments, the adjusting element 170 is coaxially mounted over the guiding element 160, such that the guiding element 160 extends through distal bore portion 332, central bore portion 334 and proximal bore portion 336 of the adjusting element 170. In some embodiments, proximally facing circumferential shoulder 340 of the adjusting element 170 is supported against 3 distally facing surface 376 of stopper element 180 optionally at all times and longitudinal arms 374 of the stopper element 180 are disposed within cut-outs 296 of the guiding element 160 and are optionally slidably moveable therealong. In some embodiments, the stopper element 180 is biased into engagement with shoulder 340 of the adjusting element 170, for example under the force of spring 184, which exerts force on the proximally facing surface 378 of the stopper element 180.

According to some exemplary embodiments, axial displacement of the adjusting element 170, and in turn of the stopper element 180 are urged by the axial force exerted by the spring 184 on the stopper element 180 and thus also on the pusher element 110. In some embodiments, the axial force of spring 184 permits radial extension of the cutting tooth 130 with respect to shaft element 102, and optionally, the extent of the radial extension of the cutting tooth is defined by the extent of rotation of the adjusting element 170, In some embodiments, the adjusting element 170 is mounted over the guiding element 160 in such a manner that the plunger 164, which is seated within the plunger enclosing socket 162 of the guiding element 160 engages one of the steps 352 of the spiral adjusting path 350 of the adjusting element 170.

According to some exemplary embodiments, the plunger 164 includes a housing 502, inside which is disposed a ball 504, optionally biased proximally under the force of a spring 506 and thus are tightly engaged with a certain step of the spiral adjusting path 350. It is appreciated that any other type of plunger may be used for selective operative engagement with one of the steps 352 of the adjusting path 350.

According to some exemplary embodiments, the adjusting element 170 is freely rotatable with respect to the other components of the drilling device 100. In some embodiments, once the adjusting element 170 is rotated relative to the guiding element 160, the plunger 164 engages another one of the steps 352 of the spiral adjusting path 350 of the adjusting element 350, which is optionally disposed at a different height than the previous step 352, thus providing for axial displacement of the adjusting element 170 with respect to the guiding element 160.

In some embodiments, upon each incremental rotation of the adjusting element 170 by the user, the plunger 164 engages another one of the steps 352 of the adjusting path 350, for example, due to engagement of the ball 504 of the plunger 164 with the recess 354 formed on step 352. Thus, in some embodiments, the height of step 352 with which the plunger 164 operatively cooperates at any given moment in time defines the extent of radial extension of the cutting tooth with respect to the outer circumference of the shaft element 102.

According to some exemplary embodiments, upon axial displacement of the adjusting element 170 relative to the guiding element 160, the stopper element 180, which is operatively engaged with shoulder 340 of the adjusting element 170 is urged to be displaced together with the adjusting element 170, optionally, such that the longitudinal arms 374 of the stopper element 180 are slidably moveable along cut-outs 296 of the guiding element 160. In some embodiments, axial displacement of the stopper element 170 in turn urges axial displacement of the pusher element 110, and thereby, optionally, causing corresponding pivoting of the crank 120 and in turn of the cutting tooth 130, which defines the resulting diameter of a bore in bone 500 of the patient upon proximal displacement of the drilling device 100 within the bone 500 of the patient.

According to some exemplary embodiments, the adjusting element 170 is disposed between the stopper element 180 and the plunger 164 formed on guiding element 160. In some embodiments, while rotating the adjusting element 170, and thus altering the axial position of the adjusting element 170 relative to the guiding element 160 due to the engagement of the plunger 164 with the spiral adjusting path 350, the adjusting element 170 urges axial displacement of the stopper element 180 along the cut-outs 296 of the guiding element 160 and thus, optionally, causing axial displacement of the pusher element 110, which in turn controls the radial orientation of the cutting tooth 130.

In some embodiments, the pusher element displacing mechanism 150 of the adjustable drilling device 100 is based on an axial displacement of the components of the drilling device 100 along longitudinal axis 107.

According to some exemplary embodiments, for example as seen in FIGS. 12A & 12B, in a closed operative orientation, the stopper element 180 is proximally spaced from the edges 297 of cut-outs 296 of the guiding element 160, thus, optionally, the pusher element 110 is disposed in its distal position, and, optionally, the cutting tooth 130 in this position is closed and does not extend from the outer perimeter of the shaft element 102. In some embodiments, this position is adapted for distally advancing the drilling device 100 and performing an initial bore in bone 500 of the patient.

According to some exemplary embodiments, an alignment between mark 274 formed on the cover element 140 with the scale markings 172 on the adjusting element 170 indicate to the user what diameter is currently adjusted.

In some embodiments, during assembly of the drilling device, the stopper element 180 is threaded onto the pusher element 110 at any desired longitudinal extent, for example to allow initial calibration of the adjustable drilling device 100.

Reference is now made to FIGS. 13A & 13B, which are respective simplified planar and sectional view illustrations of a drilling device, for example the drilling device 100 of FIGS. 1L & 1M shown in the closed operative orientation, following forward drilling into the bone 500 of the patient, sectional view is taken along lines B-B in FIG. 13A, and according to some exemplary embodiments of the invention.

According to some exemplary embodiments, FIGS. 13A & 13B show the drilling device 100 in a closed operative orientation, where the cutting tooth 130 does not radially extend from the outer surface of the shaft element 102 and is optionally adapted in this orientation for drilling an initial bore within bone 500 of the patient, for example using drilling end 200, while advancing the drilling device 100 forwardly in a distal direction through bone 500 of the patient. In some embodiments, for example as seen in FIGS. 13A & 13B, the drilling device 100 is now advanced forwardly in a distal direction through the bone 500 of the patient and an initial bore 510 of a first diameter is formed in bone 500.

It is noted that in some embodiments, all other spatial relationships between the different components of the drilling device 100 remain substantially the same as described with reference to FIGS. 12A & 12B.

In some embodiments, the drilling of the initial bore 510 is performed using the drilling end 200 of the cutting tooth 130.

Reference is now made to FIGS. 14A & 14B, which are respective simplified planar and sectional view illustrations of a drilling device, for example the drilling device 100 of FIGS. 1L & 1M shown in a first partially open operative orientation inserted into the bone 500 of the patient, sectional view is taken along lines B-B in FIG. 14A, and according to some exemplary embodiments of the invention.

According to some exemplary embodiments, for example as seen in FIGS. 14A & 14B the drilling device 100 is in a first partially open operative orientation, where the cutting tooth 130 slightly radially extends from the outer surface of the shaft element 102 and is adapted in this orientation for reaming an undercut bore having a diameter of 6 mm within the bone 500 of the patient, for example using the reaming end 202, while optionally advancing the drilling device 100 rearwardly in a proximal direction through bone 500 of the patient.

In some embodiments, for example as seen in FIGS. 14A & 14B, the adjusting element 170 is now rotated by the user, such that the scale markings 326 of the adjusting element indicate that the desired diameter is 6 mm, since marking 326 that corresponds with 6 mm is aligned with marking 274 on the cover element 140. In some embodiments, once the adjusting element 170 is rotated, the plunger 164 operatively engages another one of the steps 352 of the adjusting path 350, for example as is described in detail with reference to FIGS. 12A & 12B, thus the adjusting element 170 is slightly displaced axially in a distal direction, thereby optionally causing distal axial displacement of the stopper element 180 under the force of spring 184, and optionally in turn the pusher element 110, which moves together with the stopper element 180 is displaced distally as well.

In some embodiments, for example as seen in FIG. 14B, as compared with FIG. 12B, the stopper element 180 is now less spaced distally from the edges 297 of cut-outs 296 of the guiding element 160.

According to some exemplary embodiments, upon distal displacement of the pusher element 110, the crank 120 is pivoted about pin 122, and optionally the cutting tooth 130 is in turn pivoted about its pivoting axis, being the pivoting pin 134. In some embodiments, upon pivoting of the cutting tooth 130 about pivoting pin 134, the reaming end 202 of the cutting tooth 130 now engages the bone 500 of the patient and thus optionally widens the diameter of the initial bore 510 to an undercut bore 520 during proximal advancement of the drilling device 100. The undercut bore 520 has a diameter of 6 mm in this particular example.

In some embodiments, it is noted that the pivoting axis 134 is disposed closer to the drilling end 200 than to the reaming end 202, thus the reaming end of the cutting tooth is longer than the drilling end 200, thereby for example allowing effective engagement of the reaming end 202 with the initial bore 510.

In some embodiments, upon pivoting of the cutting tooth about pivoting axis 134, the cutting tooth 130 extends radially from the outer perimeter of the shaft element 102. In some embodiments, the drilling end 200 of the cutting tooth 130 extends radially through cut-out 250 of the shaft element 102 and the reaming end 202 simultaneously extends radially through cut-out 252 of the shaft element 102.

In some embodiments, it is noted that the fact that the cutting tooth 130 is the most distal component of the drilling device 100 allows for accurate forming of the undercut bore 520.

In some embodiments, it is noted that all other spatial relationships between the different components of the drilling device 100 remain substantially the same as described with reference to FIGS. 12A & 12B.

Reference is now made to FIGS. 15A & 15B, which are respective simplified planar and sectional view illustrations of a drilling device, for example the drilling device 100 of FIGS. 1L & 1M shown in a second partially open operative orientation inserted into the bone 500 of the patient, sectional view is taken along lines B-B in FIG. 15A, and according to some exemplary embodiments of the invention.

According to some exemplary embodiments, for example as seen in FIGS. 15A & 15B the drilling device 100 in a second partially open operative orientation, where the cutting tooth 130 is optionally more radially extends from the outer surface of the shaft element 102 and is adapted in this orientation for reaming an undercut bore having a diameter of 9 mm within the bone 500 of the patient, for example, using the reaming end 202, while optionally advancing the drilling device 100 rearwardly in a proximal direction through bone 500 of the patient.

According to some exemplary embodiments, for example as seen in FIGS. 15A & 15B the adjusting element 170 is now rotated by the user, such that the scale markings 326 of the adjusting element indicate that the desired diameter is 9 mm, for example, since marking 326 that corresponds with 9 mm is aligned with marking 274 on the cover element 140. In some embodiments, once the adjusting element 170 is rotated, the plunger 164 is optionally operatively engages another one of the steps 352 of the adjusting path 350, as is described, for example, in detail with reference to FIGS. 12A & 12B, thus the adjusting element 170 is optionally slightly more displaced axially in a distal direction, thereby, optionally, causing distal axial displacement of the stopper element 180 under the force of spring 184, and in turn the pusher element 110, which moves together with the stopper element 180 is displaced distally as well.

In some embodiments, for example as seen in FIG. 15B, as compared with FIG. 14B, that the stopper element 180 is now even less spaced distally from the edges 297 of cut-outs 296 of the guiding element 160.

In some embodiments, upon distal displacement of the pusher element 110, the crank 120 is pivoted about pin 122, and the cutting tooth 130 is in turn pivoted about its pivoting axis, being the pivoting pin 134. In some embodiments, upon pivoting of the cutting tooth 130 about pivoting pin 134, the reaming end 202 of the cutting tooth 130 now optionally engages the bone 500 of the patient and thus widens the diameter of the initial bore 510 to an undercut bore 530 during proximal advancement of the drilling device 100. The undercut bore 530 has a diameter of 9 mm in this particular example.

In some embodiments, the pivoting axis 134 is disposed closer to the drilling end 200 than to the reaming end 202, thus the reaming end of the cutting tooth is optionally longer than the drilling end 200, thereby allowing effective engagement of the reaming end 202 with the initial bore 510.

In some embodiments, upon pivoting of the cutting tooth about pivoting axis 134, the cutting tooth 130 extends radially from the outer perimeter of the shaft element 102. In some embodiments, the drilling end 200 of the cutting tooth 130 extends radially through cut-out 250 of the shaft element 102 and the reaming end 202 optionally simultaneously extends radially through cut-out 252 of the shaft element 102.

In some embodiments, the fact that the cutting tooth 130 is the most distal component of the drilling device 100 allows for example, accurate forming of the undercut bore 530.

In some embodiments, it is noted that all other spatial relationships between the different components of the drilling device 100 remain substantially the same as described with reference to FIGS. 12A & 12B.

Reference is now made to FIGS. 16A & 16B, which are respective simplified planar and sectional view illustrations of a drilling device, for example the drilling device 100 of FIGS. 1L & 1M shown in a fully open operative orientation inserted into the bone 500 of the patient, sectional view is taken along lines B-B in FIG. 16A, and according to some exemplary embodiments of the invention.

According to some exemplary embodiments, for example as seen in FIGS. 16A & 16B the drilling device 100 is in a fully open operative orientation, where optionally the cutting tooth 130 even more radially extends from the outer surface of the shaft element 102 and is optionally adapted in this orientation for reaming an undercut bore having a diameter of 12 mm within the bone 500 of the patient, using the reaming end 202, while advancing the drilling device 100 rearwardly in a proximal direction through bone 500 of the patient.

In some embodiments, for example as seen in FIGS. 16A & 16B, the adjusting element 170 is now rotated by the user, such that the scale markings 326 of the adjusting element indicate that the desired diameter is 12 mm, for example since marking 326 that corresponds with 12 mm is aligned with marking 274 on the cover element 140. In some embodiments, once the adjusting element 170 is rotated, the plunger 164 optionally operatively engages another one of the steps 352 of the adjusting path 350, for example, as is described in detail with reference to FIGS. 12A & 12B, thus the adjusting element 170 is more displaced axially in a distal direction, thereby optionally causing distal axial displacement of the stopper element 180 under the force of spring 184, and in turn the pusher element 110, which moves together with the stopper element 180 is displaced distally as well.

In some embodiments, for example as seen in FIG. 16B, as compared with FIG. 15B, the stopper element 180 now engages the edges 297 of cut-outs 296 of the guiding element 160.

In some embodiments, upon distal displacement of the pusher element 110, the crank 120 is pivoted about pin 122, and the cutting tooth 130 is in turn optionally pivoted about its pivoting axis, being the pivoting pin 134. In some embodiments, upon pivoting of the cutting tooth 130 about pivoting pin 134, the reaming end 202 of the cutting tooth 130 now engages the bone 500 of the patient and thus optionally widens the diameter of the initial bore 510 to an undercut bore 540, for example, during proximal advancement of the drilling device 100. In some embodiments, the undercut bore 540 has a diameter of 12 mm in this particular example.

In some embodiments, the pivoting axis 134 is disposed closer to the drilling end 200 than to the reaming end 202, thus the reaming end of the cutting tooth is optionally longer than the drilling end 200, thereby allowing for example effective engagement of the reaming end 202 with the initial bore 510.

In some embodiments, upon pivoting of the cutting tooth about pivoting axis 134, the cutting tooth 130 optionally extends radially from the outer perimeter of the shaft element 102. In some embodiments, the drilling end 200 of the cutting tooth 130 extends radially through cut-out 250 of the shaft element 102 and the reaming end 202 simultaneously extends radially through cut-out 252 of the shaft element 102.

In some embodiments, it is noted that the fact that the cutting tooth 130 is the most distal component of the drilling device 100 allows, for example, for accurate forming of the undercut bore 540.

In some embodiments, it is noted that all other spatial relationships between the different components of the drilling device 100 remain substantially the same as described with reference to FIGS. 12A & 12B.

Reference is now made to FIGS. 17A & 17B, which are respective simplified planar and sectional view illustrations of a drilling device, for example the drilling device 100 of FIGS. 1L & 1M shown in a closed operative orientation before removal from the bone 500 of the patient, sectional view is taken along lines B-B in FIG. 17A, and according to some exemplary embodiments of the invention.

According to some exemplary embodiments, for example as seen in FIGS. 17A & 17B the drilling device 100 in a fully closed operative orientation, where the cutting tooth 130 does not radially extend from the outer surface of the shaft element 102, adapted for withdrawal of the drilling device 100 from the bone 500 of the patient, while retracting the drilling device 100 proximally. FIGS. 17A & 17B show the drilling device 100 before retraction from the bone 500 of the patient.

In some embodiments, for example as seen in FIGS. 17A & 17B, the adjusting element 170 is now rotated by the user, such that the scale markings 326 of the adjusting element indicate that the desired diameter is 3.5 mm, since marking 326 that corresponds with 3.5 mm is aligned with marking 274 on the cover element 140. In some embodiments, once the adjusting element 170 is rotated, the plunger 164 operatively engages another one of the steps 352 of the adjusting path 350, for example, as is described in detail with reference to FIGS. 12A & 12B, thus optionally the adjusting element 170 is displaced axially in a proximal direction, thereby causing proximal axial displacement of the stopper element 180, and in turn the pusher element 110, which moves together with the stopper element 180 is displaced proximally as well.

In some embodiments, for example as seen in FIG. 17B, as compared with FIG. 16B, the stopper element 180 is now proximally spaced from edges 297 of cut-outs 296 of the guiding element 160.

In some embodiments, it is noted that all other spatial relationships between the different components of the drilling device 100 remain substantially the same as described for example, with reference to FIGS. 12A & 12B.

Reference is now made to FIGS. 18A & 18B, which are respective simplified planar and sectional view illustrations of a drilling device, for example the drilling device 100 of FIGS. 1L & 1M shown in a closed operative orientation following removal from the bone 500 of the patient, sectional view is taken along lines B-B in FIG. 18A, and according to some exemplary embodiments of the invention.

According to some exemplary embodiments, for example as seen in FIGS. 18A & 18B, the drilling device 100 is in a fully closed operative orientation, where the cutting tooth 130 does not radially extend from the outer surface of the shaft element 102, adapted for withdrawal of the drilling device 100 from the bone 500 of the patient, while optionally retracting the drilling device 100 proximally. FIGS. 18A & 18B show the drilling device 100 following retraction from the bone 500 of the patient, whereas the resulting initial bore 510 and undercut bore 520 are clearly seen, as formed within bone 500 of the patient.

Reference is now made to FIGS. 19A & 19B, which are respective simplified pictorial illustrations of an assembled view and an exploded view of a drilling device, constructed and operative in accordance with some exemplary embodiments of the present invention;

In some embodiments, a drilling device 600 is seen in FIGS. 19A & 19B.

According to some exemplary embodiments, for example as seen in FIGS. 19A & 19B, the drilling device 600 includes a shaft element 102 having a proximal end 104 and a distal end 106. In some embodiments, the shaft 102 is being arranged a long a longitudinal axis 107. In some embodiments, the shaft element 102 includes visual scale markings 108 on the outer surface thereof, for example, to enable identifying the depth of penetration of the drilling device 600 into the bone of the patient.

According to some exemplary embodiments, a pusher element 110 is adapted to be coaxially received within shaft element 102 and also defines a proximal end 112 and a distal end 114. In some embodiments, a crank 120 is pivotably connected to cutting tooth 130 and to the distal end 114 of the pusher element 110, for example, by means of a pivoting pin 122. In some embodiments, the crank 120 is in turn pivotably connected to a cutting tooth 130, for example by means of a pivoting pin 132. In some embodiments, the cutting tooth is additionally pivotably connected to the distal end 106 of the shaft element 102, for example, by means of an additional pivoting pin 134.

According to some exemplary embodiments, the proximal end 104 of the shaft element 102 is fixedly connected to the retainer 660 and is optionally partially inserted into cover element 640. In some embodiments, the proximal end 112 of the pusher element 110 is fixedly connected to at least a portion of the pusher element displacing mechanism 650, whereas the pusher element 110 is moveable with respect to the shaft element 102.

According to some exemplary embodiments, the pusher element displacing mechanism 650 includes a retainer 660.

In some embodiments, the proximal end 112 of the pusher 110 is at least partially inserted through an opening formed in the retainer 660. In some embodiments, the pusher element 110 is moveable with respect to the retainer 660 and is optionally coaxial therewith. In some embodiments, the retainer 660 is adapted to be received between the two parts of the cover element 640. In some embodiments, the retainer 660 is adapted to receive a cam connector 662 therewithin. In some embodiments, the cam connector 662 is moveable with respect to the retainer 660 and is optionally arranged coaxially therewith. In some embodiments, the cam connector 662 is adapted to be fixedly attached to the proximal end 112 of the pusher element 110, for example by means of fastener 664.

According to some exemplary embodiments, an adjuster, for example an adjusting element 670 is partially mounted within the cam connector 662, and is optionally coupled thereto in a cam-interface manner by means of pin 674. In some embodiments, the adjusting element 670 has visual scale markings 672 on the circumference thereof, for example to indicate the desired bore diameter to be formed within the bone of the patient. In some embodiments, the center of the adjusting element 670 is fixedly attached to the retainer 660 by means of pin 676. In some embodiments, the device comprises one or more adjuster retainers, for example a leaf spring 680, adapted to be positioned at each side of the adjusting element 670 and configured for tightly retaining the adjusting element 670 in place. Alternatively, the one or more adjuster retainers comprise a plunger that can be adapted to be positioned at each side of the adjusting element 670 and configured for tightly retaining the adjusting element 670 in place.

In some embodiments, a bit connector 690 is adapted to be fixedly connected to the retainer 660 at its distal end and is adapted to be attached to a power tool at its proximal end. In some embodiments, the power tool is configured to impart rotational movement to the bit connector, and further to the shaft element 102.

In some embodiments, the drilling device 600 provides for creating undercut bores of various diameters, for example by opening cutting tooth 130 of the drilling device 600 to a different radial extent as is described in detail hereinbelow. In some embodiments, the adjusting element 670 is preferably rotatable by the user in the direction of the longitudinal axis 107 and is optionally adapted to cooperate with the cam connector 662 and thereby with the pusher element 110, which cooperation enables opening of the cutting tooth 130 to various radial extents and thus forming various diameters of undercut bores in the bone of the patient.

Reference is now made to FIG. 19C, which is a respective simplified pictorial illustration of an exploded view of a drilling device having an adjuster retainer, for example a plunger interacting with an adjusting element, according to some exemplary embodiments of the invention.

According to some exemplary embodiments, for example as seen in FIG. 19C, a drilling device, for example drilling device 1000 comprises a shaft, for example the shaft element 102 having a distal end 106 and a proximal end 104, as further described in FIGS. 19A and 19B.

According to some exemplary embodiments, the device 1000 further comprises a movable coupler, for example pusher element 110 coupled to the shaft element 102. In some embodiments, the pusher element 110 is adapted to be coaxially received within shaft element 102 and also defines a proximal end 112 and a distal end 114. In some embodiments, the device 1000 comprises a crank, for example a crank 120, pivotably connected to a bone borer, for example a cutting tooth 130. In some embodiments, the crank 120 is pivotably connected to the distal end 114 of the pusher element 110, for example, by means of a pivoting pin 122. In some embodiments, the crank 120 is in turn pivotably connected to a cutting tooth 130, for example by means of a pivoting pin 132. In some embodiments, the cutting tooth is additionally pivotably connected to the distal end 106 of the shaft element 102, for example, by means of an additional pivoting pin 134.

According to some exemplary embodiments, the shaft 102, for example the proximal end 104 of the shaft 102 is fixedly connected to a retainer, for example retainer 660. Optionally, the proximal end 104 is at least partly inserted into a cover, for example a cover 1029 shown in FIG. 24I, formed from cover portions 1008 and 1014, which are optionally complimentary cover portions. In some embodiments, the proximal end 112 of the pusher element 110 is connected, for example fixedly connected, to at least a portion of a pusher element displacing mechanism comprising the retainer 660. In some embodiments, the pusher element 110 is moveable with respect to the retainer 660, and is optionally coaxial therewith.

According to some exemplary embodiments, the pusher element displacing mechanism further comprises a cam connector, for example cam connector 662. In some embodiments, the retainer 660 is adapted to receive the cam connector 662 therewithin. In some embodiments, the cam connector 662 is moveable with respect to the retainer 660 and is optionally arranged coaxially therewith. In some embodiments, the cam connector 662 is adapted to be fixedly attached to the proximal end 112 of the pusher element 110, for example by means of fastener 664.

According to some exemplary embodiments, an adjuster, for example an adjusting element 1002 is at least partially mounted within the cam connector 662, and is optionally coupled thereto in a cam-interface manner by means of pin 674. In some embodiments, the adjusting element 1002 has visual scale markings 1016 and 1018 arranged on the circumference of one or two of the side walls of the adjusting element 1002, for example to provide a visual indication regarding a desired bore diameter to be formed within the bone of the patient. In some embodiments, the adjusting element 1002, for example a center of the adjusting element 670 is fixedly attached to the retainer 660 by means of pin 676.

According to some exemplary embodiments, for example as described in relation to device 600, at least one plunger, for example a spring plunger, is positioned at one or both sides of the adjusting element 1002. In some embodiments, for example as shown in FIG. 19C, the device 1000 comprises two plungers, for example spring plungers. In some embodiments, each of the plungers comprises a plunger housing, for example plunger housings 1004 and 1010, and a spring, for example springs 1006 and 1012 respectively. In some embodiments, each of the plunger housing comprises a tip placed in contact with a side wall of the adjusting element, for example adjusting element 1002. In some embodiments, the tip of the housing is shaped and sized to enter, at least partly, into a plurality, for example 2, 3, 4, 5, 6, 7, 8, 9, 10, 11 or any larger number of indentations formed in the side wall. In some embodiments, each of the plungers are positioned between a cover portion, for example cover portions 1008 and 1014 and a side wall of the adjusting element 1002.

According to some exemplary embodiments, the adjusting element, for example, adjusting element 1002 is a movable adjusting element, optionally a rotationable adjusting element. In some embodiments, rotation of the adjusting element repositions the plunger housing tip from one indentation to another indentation of the side wall of the adjusting element 1002. In some embodiments, the spring of each plunger pushes the plunger housing tip against the side wall of the adjusting element 1002, for example against the indentations of the adjusting element 1002. In some embodiments, friction forces applied by the plunger on the side wall of the adjusting element, for example on an indentation on the side wall of the adjusting element 1002, hold the adjusting element in a selected rotation orientation. In some embodiments, each selected rotation orientation matches a discrete position of the bone borer, for example cutting tooth 130 relative to the shaft 102 or a longitudinal axis of the shaft 102.

According to some exemplary embodiments, the device, for example device 1000 is connectable to a power tool, for example a motor, configured to rotate the device 1000 or at least the cutting tooth 130 in up to 2000 rounds per minute (RPM), for example 500 RPM, 1000 RPM, 1500 RPM or any intermediate, smaller or larger value. In some embodiments, the device comprises a bit connector, for example a bit connector 1020, shaped and sized to be fixedly connected to the retainer 660 at its distal end and is adapted to be attached to a power tool at its proximal end. In some embodiments, a proximal end of the bit connector 1020 has a rectangular cross-section that is optionally complimentary with a cross-section of a drilling device connector of the power tool. In some embodiments, as described previously, the power tool is configured to impart rotational movement to the bit connector, and further to the shaft element 102.

According to some exemplary embodiments, the drilling device 600 is for creating undercut bores of various diameters, for example by opening cutting tooth 130 of the drilling device 600 to a different radial extent as is described in detail hereinbelow. In some embodiments, the different radial extent of the cutting tooth is pre-determined by the discrete positions of the cutting tooth and the selected rotation orientations of the adjusting element 1002. In some embodiments, the adjusting element 1002 is configured to be rotatable by the user in the direction of the longitudinal axis of the shaft and is optionally adapted to cooperate with the cam connector 662 and thereby with the pusher element 110, which cooperation enables opening of the cutting tooth 130 to various radial extents, for example various pre-determined radial extents and thus forming various diameters of undercut bores in the bone of the patient.

According to some exemplary embodiments, for example as shown in FIGS. 19D-19F, the drilling device comprises a pin, for example pin 677 for coupling the adjusting element 670 is to the retainer 660, for example instead of pin 676. In some embodiments, for example as shown in FIGS. 19E and 19F, the pin 677 comprises one or more interference locking portions, for example Christmas tree locks 679 and 681 at both ends of the pin 677. In some embodiments, the interference locking portions are spaced apart, and are configured to secure the pin 677 within the retainer 660.

Exemplary Drilling Device with a Replaceable Shaft

Reference is now made to FIGS. 19G and 19H depicting a drilling device with a removable, for example a replaceable shaft, according to some exemplary embodiments of the invention.

According to some exemplary embodiments, the drilling device, for example drilling device 680 is provided as a kit, having a replaceable shaft 682, removably coupled to an adjusting mechanism, optionally positioned within a cover 684, for example a cover formed from cover portions 1008 and 1014, shown in FIG. 19C. In some embodiments, the removable shaft comprises a pusher element and a movable bone borer. In some embodiments, the removable shaft is configured to be removably coupled to the cover and/or to the adjusting mechanism by at least one reversibly coupling connector, for example a snap connector or at least one screw. In some embodiments, the snap connecter is part of the retainer, for example retainer 660. Alternatively, the snap connector is part of the cover. In some embodiments, the snap connector is part of the cam element 662. Alternatively, the removable shaft 682 is configured to be coupled to the cover 684 via a threading 686 located at a proximal end of the shaft 682.

According to some exemplary embodiments, each replaceable shaft has a different shaft length and/or a different shaft diameter. Additionally or alternatively, each replaceable shaft has a bone borer with a different size, for example a different width, a different length, a different drilling tip and/or a different reamer.

According to some exemplary embodiments, a user of the drilling device determines a treatment type, for example ACL/PCL reconstruction and meniscus root repair and/or a treatment region, for example bones, knees, shoulders and other joints. In some embodiments, the user selects the removable shaft according to the determined treatment type and/or according to the determined target region.

According to some exemplary embodiments, the selected shaft and/or the bone borer is removably coupled to an adjusting mechanism of a bone borer, for example a bone borer movement adjuster or a bone borer tilting adjuster, and/or to a cover of the drilling device. Additionally, a pusher mechanism in the shaft is removably coupled to the adjusting mechanism. In some embodiments, a different shaft is selected for pediatric uses, and/or for veterinary uses. In some embodiments, the selected shaft is configured for a single use. In some embodiments, the adjusting mechanism is configured to be reused. In some embodiments, the selected shaft and/or the bone borer of the selected shaft are decoupled from the adjusting mechanism, for example when a bone opening is formed and/or when a reaming process is over. Alternatively, the selected shaft and/or the bone borer of the selected shaft are decoupled from the adjusting mechanism, for example when a different shaft or a different bone borer is needed during the reaming process.

Figure 20A:
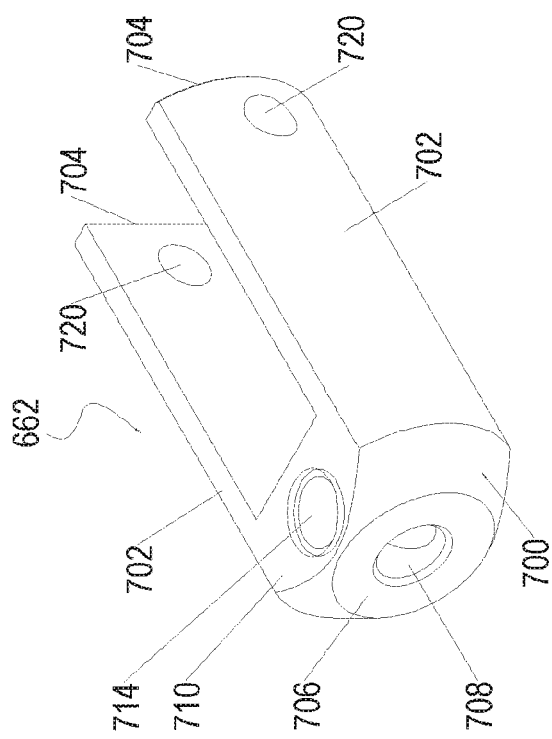
FIGS. 20A-20C are a respective simplified pictorial illustration and two different plan views of a cam connector, forming part of the drilling device of FIGS. 19A & 19B, and according to some embodiments of the invention.
Figure 20B:
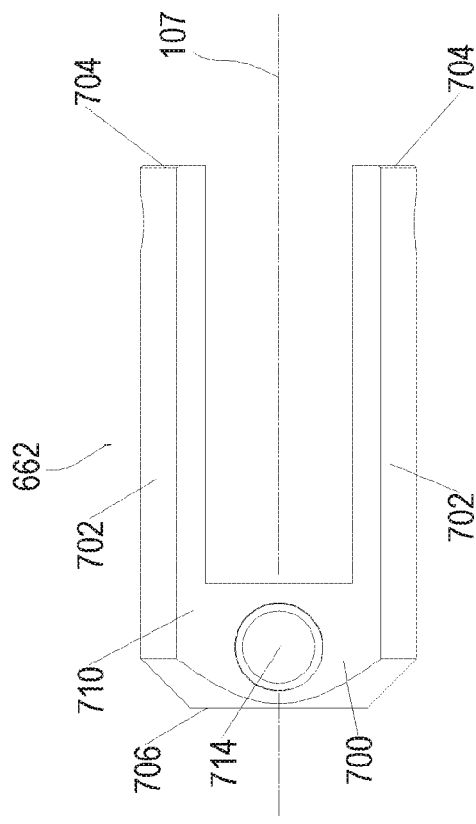
Figure 20C:
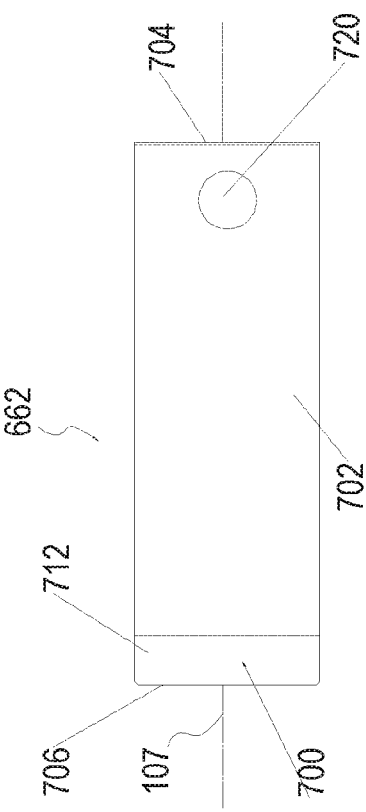

Reference is now made to FIGS. 20A-20C, which are a respective simplified pictorial illustration and two different plan views of a cam connector, for example the cam connector 662, forming part of the drilling device 600 of FIGS. 19A & 19B, and according to some exemplary embodiments of the invention.

According to some exemplary embodiments, the cam connector 662 is an integrally formed element, optionally arranged along longitudinal axis 107.

In some embodiments, the cam connector 662 is generally U-shaped and has a distal hub portion 700 and optionally two proximally extending longitudinal arms 702 extending therefrom, each ending at a proximally facing edge 704. In some embodiments, Hub portion 700 has a distally facing surface 706 and an opening 708 extending along longitudinal axis 107. In some embodiments, Hub portion 700 additionally defines an upwardly facing surface 710 and a downwardly facing surface 712. In some embodiments, a bore 714 extends downwardly from the upwardly facing surface 710 and is arranged generally transversely with respect to opening 708.

According to some exemplary embodiments, openings 720 are formed through each of the longitudinal arms 702 and positioned generally adjacent to the proximally facing edges 704. In some embodiments, openings 720 generally extend transversely with respect to longitudinal axis 107.

Reference is now made to FIGS. 21A-21C, which are a respective simplified pictorial illustration and two different plan views of a retainer, for example the retainer 660, forming part of the drilling device 600 of FIGS. 19A & 19B, and according to some exemplary embodiments of the invention.

According to some exemplary embodiments, the retainer 660 is an integrally formed element, optionally arranged along longitudinal axis 107.

In some embodiments, the retainer 660 is generally U-shaped and has a distal hub portion 740 and two proximally extending longitudinal arms 742 extending therefrom, each ending at a proximally facing edge 744. In some embodiments, Hub portion 740 has a distally facing wall 746 and a sleeve 748 distally extending therefrom. In some embodiments, a bore 750 extends through the sleeve 748 and the hub portion 740 and arranged along longitudinal axis 107. In some embodiments, the longitudinal arms 742 are arcuate in shape and each defines an inner-facing arcuate wall 752 and an outer facing arcuate wall 754. In some embodiments, two elongated tunnels 756 are formed between the longitudinal arms 742.

According to some exemplary embodiments, openings 760 are formed through each of the longitudinal arms 742 and positioned generally in an intermediate location along the longitudinal extent of arms 742. In some embodiments, openings 720 generally extend transversely with respect to longitudinal axis 107.

Figure 22A:
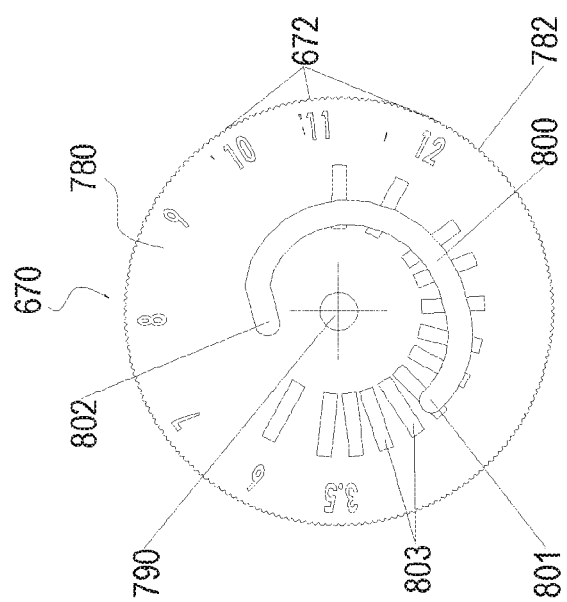
FIGS. 22A-22C are a respective simplified pictorial illustration and two different plan views of a cam element, forming part of the drilling device of FIGS. 19A & 19B, and according to some embodiments of the invention.
Figure 22C:
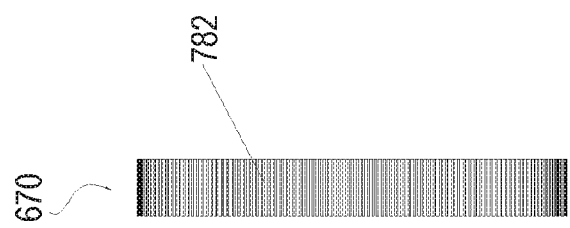
Figure 22B:
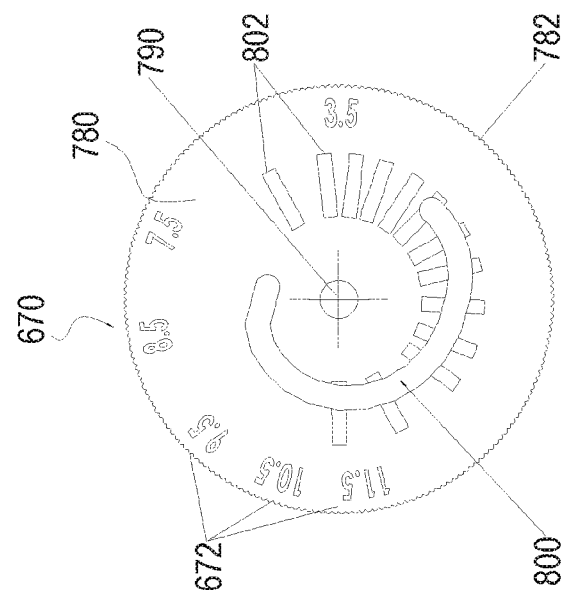

Reference is now made to FIGS. 22A-22C, which are a respective simplified pictorial illustration and two different plan views of a cam element, for example the cam element 670, forming part of the drilling device 600 of FIGS. 19A & 19B, and according to some exemplary embodiments of the invention.

According to some exemplary embodiments, cam element 670 is an integrally formed disc-shaped element, having a first and second side walls 780 and a circumferential rim gripping surface 782. In some embodiments, the gripping surface 782 is corrugated to facilitate user's finger interaction therewith. In some embodiments, and as noted hereinabove, visual scale markings 672 are provided on both side walls 780 of the cam element 670, markings 672 are optionally located at the vicinity of the rim gripping surface 782.

According to some exemplary embodiments, a central opening 790 is formed in the middle of the cam element. In some embodiments, a cam tunnel 800 is formed through the cam element 670 and arranged preferably at least partially around central opening 790, optionally forms an eccentric shape with respect to the central opening 790. In some embodiments, the cam tunnel 800 includes a first end 801 and a second end 802.

It is additionally seen in FIGS. 22A & 22B that a plurality of recesses 803 is formed on each of the side walls 780 and arranged at least partially around central opening 790 and concentrically therewith.

Reference is now made to FIGS. 22D-22F, depicting an adjuster, for example an adjusting element, configured to interacts with one or more plungers, according to some exemplary embodiments of the invention.

According to some exemplary embodiments, an adjuster, for example an adjusting element 1002, is optionally shaped as a disc with a thin cross-section, for example as shown in FIG. 22E. In some embodiments, the adjusting element 1002 comprises two opposite side walls, for example side walls 1021 and 1023 and a circumferential rim, optionally having a gripping surface 1017. In some embodiments, the adjusting element 1002 comprises an opening 1019, for example a central opening, crossing through the adjusting element and connecting the two opposite side walls 1021 and 1023. In some embodiments, the opening is shaped and sized to allow the insertion of a pivot, for example pin 676 shown in FIG. 19C, for connecting the adjusting element 1002 to the drilling device, for example the drilling device 1000 shown in FIG. 19C.

According to some exemplary embodiments, the adjusting element 1002 comprises on at least one side wall, a plurality of indentations or sockets, for example indentations 1015 and 1017 on side wall 1021 and indentations 1016 and 1018 on side wall 1023. In some embodiments, the indentations are arranged on the circumference of the side wall, for example in an arc or a circular pattern. In some embodiments, the indentations are shaped and sized to fit a plunger, for example a tip of a plunger placed in contact with the indentations.

According to some exemplary embodiments, the adjusting element 1002 comprises one or more human detectable markings, for example marking 1013, on at least one side wall of the adjusting element 1002. In some embodiments, the one or more markings are used to mark a specific rotation orientation or rotation position of the adjusting element 1002, for example relative to a fixed marking on the device. In some embodiments, each specific rotation orientation and marking indicates a discrete position of a bone borer of the device, for example cutting tooth 131 relative to the shaft, for example shaft 106. In some embodiments, the discrete position comprises a close position of the bone borer, where the bone borer is aligned with the longitudinal axis of the shaft for example during drilling into the tissue, and a plurality of open positions, where the bone borer is tilted relative to the shaft, for example during reaming, optionally retrograde reaming, of an opening in the tissue. In some embodiments, each of the one or more human detectable markings, for example marking 1013, indicates a specific width of the tissue opening formed by the drilling device, when the cutting tooth is positioned in a discrete position which correlates with the specific human detectable marking on the adjusting element 1002.

According to some exemplary embodiments, for example as shown in FIG. 22E, the adjusting element 1002 comprises a circumferential rim comprising a gripping surface 1017. In some embodiments, the gripping surface 1017 is optionally corrugated to facilitate user's finger interaction therewith. In some embodiments, the markings, for example markings 1013 are located at the vicinity of the rim gripping surface 1017.

Reference is now made to FIGS. 24F-24I, which are a respective simplified pictorial illustrations, of a cover, forming part of the drilling device 1000 of FIG. 19C, and according to some exemplary embodiments of the invention.

According to some exemplary embodiments, a cover, for example cover 1029 includes two generally identical cover portions, for example cover portions 1008 and 1014, also shown in FIG. 19C. In some embodiments, each of the cover portions 1008 and 1014 is optionally made of plastic. In some embodiments, the cover portions are adapted to be fastened to each other for example by screws or snaps or any other suitable fastening means.

In some embodiments, each cover portion of the cover 1029 generally extends along a longitudinal axis 107 and defines an outer surface, for example outer surface 1045, and an inner surface, for example inner surface 1047.

In some embodiments, the cover portions when fastened together are forming the cover 1029, which defines a proximal end 1049 and a distal end 1051. In some embodiments, an opening 1024 is formed through the proximal end 1049 and extends along longitudinal axis 107. In some embodiments, an additional opening 1022 is formed through the distal end 1051 and also extends along the longitudinal axis 107. In some embodiments, an aperture 1041 is formed at an intermediate location of each of the cover portions, together adapted for receiving a portion of the adjuster, for example the adjusting element 1002. In some embodiments, at least one of the covers comprises a visual marking, for example marking 1043 located on an external surface of at least one of the covers and proximal to, or at the aperture 1041. In some embodiments, the visual marking is configured to at least partially aligned with a marking on a side wall of the adjusting element 1002, for example marking 1013, for example for indicating a discrete position of the cutting tooth and/or a specific tissue opening width setup of the drilling device.

According to some exemplary embodiments, one or more inwardly extending flexible protrusions, for example protrusions 1042 and 1044, are formed on and extending from an inner surface of at least one of the cover portions. Optionally, the protrusions are snap-fit protrusions. In some embodiments, the protrusions, for example protrusions 1042 and 1044 are configured to interlock the two cover portions 1014 and 1008.

According to some exemplary embodiments, an inwardly facing socket, for example socket 1026, is formed on an inner surface of at least one or both of the cover portions, for example cover portions 1008 and 1014. In some embodiments, the socket is shaped and sized to hold a plunger, for example a spring plunger. In some embodiments, the socket 1026 comprises an inner inwardly extending protrusion, shaped and sized to penetrate through an inner lumen of a spring of the plunger, while optionally, the plunger housing is positioned within the socket 1026.

Reference is now made to FIGS. 24J-24M depicting a spring plunger positioned in a socket formed in a cover portion and interacting with an adjuster, for example an adjusting element, according to some exemplary embodiments of the invention;

According to some exemplary embodiments, for example as shown in FIG. 24K, the adjuster, for example adjusting element 1002 is positioned within cover 1029, while at least a portion of the adjusting element 1002 extends through aperture 1041. In some embodiments, the adjusting element is retained tightly within the cover 1029 by one or more plungers, for example one or more spring plungers pressed against the side walls of the adjusting element 1002.

According to some exemplary embodiments, the plunger, for example the spring plunger comprising a spring 1012 and a plunger housing is shaped and sized to be positioned within a socket, for example socket 1026 formed in an inner surface of a cover portion. In some embodiments, an inward protrusion within the socket 1026, for example protrusion 1025 is shaped and sized to penetrate at least partly through a central lumen of the spring 1012. In some embodiments, for example as shown in FIGS. 24L and 24M, a plunger housing 1010 having a tip 1032 is positioned around the spring, between the spring and the socket 1026 walls, while the tip 1032 is inwardly directed towards the adjuster, for example adjusting element 1002.

According to some exemplary embodiments, for example as shown in FIGS. 24L and 24M, the spring 1012 is configured to push the housing tip 1032 against a side wall of the adjusting element 1002, for example into an indentation 1016 formed in the side wall. In some embodiments, rotation of the adjusting element 1002 presses the plunger and allows rotation of the adjusting element 1002 until the housing tip 1032 penetrates into a new indentation in the side wall of the adjusting element 1002.

According to some exemplary embodiments, for example as shown in FIG. 24L, at least two plungers, are pressed against the side walls of the adjusting element 1002. In some embodiments, each of the plungers press a plunger housing tip into an indentation in both of the opposite side walls of the adjusting element 1002.

Reference is now made to FIGS. 23A-23C, which are a respective simplified pictorial illustration and three different plan views of a bit connector, for example the bit connector 690, forming part of the drilling device 600 of FIGS. 19A & 19B, and according to some exemplary embodiments of the invention.

According to some exemplary embodiments, a Bit connector 690 is an integrally made element, which is arranged along longitudinal axis 107.

In some embodiments, the bit connector 690 has a proximal portion 810 of a first diameter, adapted to be connected to a power tool, for example for imparting rotational movement from the power tool to the drilling device 600. In some embodiments, the bit connector 690 further has a generally circular distal portion 812 of a second diameter, which is optionally substantially larger than the first diameter. In some embodiments, the distal portion 812 defines a distally facing surface 814, a proximally facing surface 815 and two generally diametrically opposed protrusions 816 extend distally from the distally facing surface 814.

Reference is now made to FIGS. 24A-24E, which are a respective simplified pictorial illustration, two different plan views, and two sectional views of a cover element, for example the cover element 640, forming part of the drilling device 600 of FIGS. 19A & 19B, the sectional views being taken along lines E-E in FIG. 24B, and according to some exemplary embodiments of the invention.

According to some exemplary embodiments, cover element 640 includes two generally identical cover portions, optionally made of plastic, which are adapted to be fastened to each other for example by screws or snaps or any other suitable fastening means.

In some embodiments, each cover portion of the cover element 640 generally extends along longitudinal axis 107 and defines an outer surface 830 and an inner surface 832.

In some embodiments, the cover portions when fastened together are forming the cover element 640, which defines a proximal end 834 and a distal end 836. In some embodiments, an opening 838 is formed through the proximal end 834 and extends along longitudinal axis 107. In some embodiments, an additional opening 840 is formed through the distal end 836 and also extends along the longitudinal axis 107. In some embodiments, an aperture 841 is formed at an intermediate location of each of the cover portions, together adapted for receiving a portion of the adjusting element 670.

According to some exemplary embodiments, a radially inwardly extending protrusion 842 is formed on each of the cover portions and is optionally disposed adjacent the proximal end 834. In some embodiments, an additional radially inwardly extending protrusion 844 is formed on each of the cover portions and is generally distally spaced from protrusion 842.

Reference is now made to FIGS. 25A-25C, which are a respective simplified pictorial illustration, and two different plan views of a leaf spring, for example the leaf spring 680, forming part of the drilling device 600 of FIGS. 19A & 19B, and according to some exemplary embodiments of the invention.

According to some exemplary embodiments, the leaf spring 680 is an integrally made element, which has two retaining portions 860, each having an opening 862 formed thereon, adapted for example, for enabling attachment of the spring leaf 680 to the cover element 640.

In some embodiments, a protruding curved portion 864 is formed between the two retaining portions 860.

In some embodiments, it is noted that the remaining components of the drilling device 600 are generally identical to the components of drilling device 100, as described in detail hereinabove, for example, components such as the cutting tooth 130, crank 120, pusher element 110 and shaft element 102.

Reference is now made to FIGS. 26A-26C, which are respective two different plan views and a sectional view illustration of a drilling device, for example the drilling device 600 of FIGS. 19A & 19B shown in a closed operative orientation, before insertion into a bone of a patient, sectional view is taken along lines B-B in FIG. 26B, and according to some exemplary embodiments of the invention.

According to some exemplary embodiments, for example as seen in FIGS. 26A-26C, the drilling device 600 is positioned in a closed operative orientation, whereas the cutting tooth 130 is in its closed operative orientation.

According to some exemplary embodiments, the cam connector 662 is adapted to be slidably coaxially mounted within the retainer 660. In some embodiments, the adjusting element 670 is adapted to be rotatably partially positioned within both the retainer 660 and the cam connector 662 and optionally adapted to extend between longitudinal arms 742 of the cam connector 662 and between longitudinal arms 742 of the retainer 660. In some embodiments, the retainer 660 is fixedly attached to the adjusting element 670, for example by means of pin 676, such that pin 676 extends along axis 850, that is generally perpendicular to axis 107 and optionally extends through the center of the adjusting element 670. In some embodiments, the pin 676 extends through openings 760 of the retainer 660 and through central opening 790 of the adjusting element 670.

Additionally, for example as seen in FIGS. 26A-26C, the cam connector 662 is moveably coupled to the adjusting element 670, for example by means of pin 674. In some embodiments, pin 674 extends through openings 720 of cam connector 662 and through cam tunnel 800 of adjusting element 670. In some embodiments, the cam connector 662 is further fixedly attached to the proximal end 112 of the pusher element 110, for example by means of fastener 664.

Additionally, for example as seen FIGS. 26A-26C, protrusions 816 of the bit connector 690 are inserted into elongated tunnels 756 formed between longitudinal arms 742 of retainer 660, and thus the bit connector 690 is adapted to transfer rotation from the power tool to the shaft 102.

According to some exemplary embodiments, pusher element displacing mechanism 650 is generally mounted within and enclosed by cover element 640, while rim gripping surface 782 of the adjusting element 670 optionally extends outwardly through opening 841 formed in each of the cover element 640 portions. In some embodiments, the longitudinal arms 742 of the retainer 660 are supported by protrusions 844 of the cover element 640 and distal portion 812 of the bit connector 690 is supported on protrusion 842 of the cover element 640, such that the proximally facing surface 815 engages the distally facing wall of protrusion 842 and thus the bit connector 690 is prevented from displacement in a proximal direction.

According to some exemplary embodiments, the leaf springs 680 are supported between each of the cover element 640 portions and one of the plurality of recesses 803 formed on each side of the adjusting element 670, adapted for retaining the adjusting element 670 in a single discrete position at each given point of time.

Alternatively, plungers, such as plunger 164, can be supported between each of the cover element 640 portions and one of a plurality of openings formed through the adjusting element 670, adapted for retaining the adjusting element 670 in a single discrete position at each given point of time.

According to some exemplary embodiments, the shaft element 102 is fixedly connected to the cover element 640, such that the proximal end 104 of the shaft element 102 is inserted into opening 840 of the cover element 640. In some embodiments, the pusher element 110 is partially enclosed within the shaft element 102 and disposed such that the proximal end 112 of the pusher element extends proximally with respect to the proximal end 104 of the shaft element 102.

According to some exemplary embodiments, for example as seen in FIGS. 26A-26C, the distal end 106 of the shaft and the distal end 114 of the pusher element 110 are connected with the crank 120, for example by means of pivoting pin 122. In some embodiments, the crank 120 is pivotably connected to the cutting tooth 130, for example by means of pivoting pin 132. In some embodiments, the cutting tooth 130 is pivotably connected to the distal end 106 of the shaft element 102, which optionally has two cut-outs 250 and 252, which enable radial extension of the cutting tooth 130.

According to some exemplary embodiments, the cam connector 662 and the pusher element 110 are fixedly attached and thus optionally are moveable together. In some embodiments, the cam connector 662 and the pusher element 110 are together slidably axially moveable with respect to the center of the adjusting element 670. In some embodiments, displacement of pin 674 along cam tunnel 800 when the adjusting element 670 is rotated by the user, optionally urges longitudinal displacement of the cam connector 662 along the longitudinal axis 107. In some embodiments, longitudinal displacement of the cam connector 662 in turn urges longitudinal displacement of the pusher element 110. In some embodiments, upon displacement of the pusher element in the distal direction, the cutting tooth 130 is pivoted and the resulting bore diameter is thereby enlarged.

According to some exemplary embodiments, the cutting tooth 130 is the distalmost component of the drilling device 600. In some embodiments, the cutting tooth 130 extends distally with respect to the distal end 106 of the shaft element 102. In some embodiments, the cutting tooth 130 serves as the drilling tip.

In some embodiments, the adjusting element 670 is rotatable in the direction of longitudinal axis 107.

According to some exemplary embodiments, for example as seen in FIGS. 26A-26C the drilling device is disposed in the closed operative orientation, where the cutting tooth 130 does not radially extend from the outer surface of the shaft element 102 and is optionally adapted in this orientation for drilling an initial bore within bone 500 of the patient, using drilling end 200, for example, while advancing the drilling device 600 in a distal direction through bone 500 of the patient.

According to some exemplary embodiments, rotation of the adjusting element 670, and in turn of the cam connector 662 urge axial displacement of the pusher element 110, which optionally in turn causes radial extension of the cutting tooth 130 with respect to shaft element 102. In some embodiments, the extent of the radial extension of the cutting tooth is defined by the extent of rotation of the adjusting element 670.

In some embodiments, the leaf springs 680 are biased radially inwardly to be seated within one of a plurality of recesses 803 of the adjusting element 670 and thus optionally retain the adjusting element 670 in a single discrete rotational orientation, thus in turn retaining the cutting tooth 130 extended to a certain discrete radial extent. In some embodiments, other one or more types of biasing mechanisms retaining the adjusting element 670 in place are being used.

According to some exemplary embodiments, the adjusting element 670 is freely rotatable with respect to the other components of the drilling device 600. In some embodiments, once the adjusting element 670 is rotated relative to the cam connector 662, the pin 674 which couples the adjusting element 670 with the cam connector 662 is displaced along the cam tunnel 800 and thus optionally urges axial displacement of the cam connector 662.

According to some exemplary embodiments, upon each incremental rotation of the adjusting element 670 by the user, the cam connector 662 is axially displaced along axis 107 and thus optionally displaces the pusher element 110 and defines the extent of radial extension of the cutting tooth 130 with respect to the outer circumference of the shaft element 102.

According to some exemplary embodiments, upon axial rotation of the adjusting element 670, the cam connector 662 is displaced relative to the retainer 660. In some embodiments, axial displacement of the cam connector 662 in turn urges axial displacement of the pusher element 110, and thereby optionally causing corresponding pivoting of the crank 120 and in turn of the cutting tooth 130, which defines, for example, the resulting diameter of a bore in bone 500 of the patient upon proximal displacement of the drilling device 600 within the bone 500 of the patient.

According to some exemplary embodiments, for example as seen in FIGS. 26A-26C in this closed operative orientation, the distal hub 700 of the cam connector 662 is proximally spaced from the distal hub portion 740 of the retainer 600, thus the pusher element 110 is disposed in its distal position, and the cutting tooth 130 in this position is closed and does not extend from the outer perimeter of the shaft element 102. In some embodiments, this position is adapted for distally advancing the drilling device 600 and performing an initial bore in bone 500 of the patient. In some embodiments, for example as seen in FIG. 26C, the pin 674 is disposed at the first end 801 of the cam tunnel 800 of the adjusting element 670 in this closed operative orientation, thus positioning the cam connector at its proximal operative orientation.

According to some exemplary embodiments, an alignment between mark that may be formed on the cover element 640 with the scale markings 672 on the adjusting element 670 indicate to the user what diameter is currently adjusted.

Reference is now made to FIGS. 27A-27C, which are respective two different plan views and a sectional view illustration of a drilling device, for example the drilling device 600 of FIGS. 19A & 19B shown in the closed operative orientation, following forward drilling into the bone 500 of the patient, sectional view is taken along lines B-B in FIG. 27B, and according to some exemplary embodiments of the invention.

According to some exemplary embodiments, for example as seen in FIGS. 27A-27C, the drilling device 600 is positioned in a closed operative orientation, whereas the cutting tooth 130 is in its closed operative orientation.

According to some exemplary embodiments, for example as seen in FIGS. 26A-26C, the drilling device is disposed in the closed operative orientation, where the cutting tooth 130 does not radially extend from the outer surface of the shaft element 102 and in this orientation an initial bore 510 of a first diameter is formed within bone 500 of the patient, using, for example, drilling end 200, while optionally advancing the drilling device 600 in a distal direction through bone 500 of the patient.

In some embodiments, the rotation of the adjusting element 670, and in turn of the cam connector 662 urge axial displacement of the pusher element 110, which in turn causes radial extension of the cutting tooth 130 with respect to shaft element 102. In some embodiments, the extent of the radial extension of the cutting tooth is defined by the extent of rotation of the adjusting element 670. In some embodiments, in this operative orientation, the diameter of the initial bore 510 is set in a range of 1.5 mm-5.5 mm, for example, 3 mm, 3.5 mm, 4 mm, 4.5 mm or any intermediate, smaller or larger diameter or range of diameters. In some embodiments, any other suitable diameter for an initial bore can be formed using drilling device 600 in the closed operative orientation.

According to some exemplary embodiments, for example as seen in FIG. 27A, an alignment between mark that may be formed on the cover element 640 with the scale markings 672 on the adjusting element 670 indicate to the user what diameter is currently adjusted. In some embodiments, all other spatial relationships between the different components of the drilling device 600 remain substantially the same as described for example with reference to FIGS. 26A-26C.

Reference is now made to FIGS. 28A-28C, which are respective two different plan views and a sectional view illustration of a drilling device, for example the drilling device 600 of FIGS. 19A & 19B shown in a first partially open operative orientation inserted into the bone 500 of the patient, sectional view is taken along lines B-B in FIG. 28B, and according to some exemplary embodiments of the invention.

According to some exemplary embodiments, for example as seen in FIGS. 28A-28C, the drilling device 600 is in a first partially open operative orientation, where the cutting tooth 130 slightly radially extends from the outer surface of the shaft element 102 and is adapted in this orientation for example, for reaming an undercut bore having a diameter in a range of 4-8 mm, for example 5 mm, 5.5 mm, 6 mm or any intermediate, smaller or larger diameter or range of diameters within the bone 500 of the patient, using for example the reaming end 202, while optionally advancing the drilling device 600 rearwardly in a proximal direction through bone 500 of the patient.

According to some exemplary embodiments, rotation of the adjusting element 670, and in turn of the cam connector 662 urge axial displacement of the pusher element 110, which axially displaces and pivots the crank 120 and in turn causes radial extension of the cutting tooth 130 with respect to shaft element 102, and the extent of the radial extension of the cutting tooth is defined by the extent of rotation of the adjusting element 670. In some embodiments, in this particular operative orientation, the diameter of the undercut bore 520 is set in a range of 4-8 mm, for example 5 mm, 5.5 mm, 6 mm or any intermediate, smaller or larger diameter or range of diameters. In some embodiments, any other suitable diameter for the undercut bore can be formed using drilling device 600 in the first partially open operative orientation.

According to some exemplary embodiments, for example as seen in FIG. 28A, an alignment between mark that may be formed on the cover element 640 with the scale markings 672 on the adjusting element 670 indicate to the user what diameter is currently adjusted.

According to some exemplary embodiments, for example as seen in FIG. 28A, the distal hub portion 700 of the cam connector 662 is proximally spaced from the distal hub portion 740 of the retainer 660. In some embodiments, for example as seen in FIG. 28C, a pin 674 is slightly displaced along cam tunnel 800 away from the first end 801 thereof. Optionally, due to fixed connection between pin 674 and cam connector 662, following displacement of pin 674 along the cam tunnel 800, the cam connector 662 is displaced distally, thereby, for example, urging distal displacement of the pusher element 110 and thus opening of the cutting tooth 130 to the diameter set by the user.

According to some exemplary embodiments, the adjusting element 670 is held in a certain orientation by means of leaf springs 680 that are optionally seated within one of the recesses 803 of the adjusting element 670 and thus optionally prevent inadvertent rotation thereof.

According to some exemplary embodiments, upon distal displacement of the pusher element 110, the crank 120 is pivoted about pin 122, and the cutting tooth 130 is in turn pivoted about its pivoting axis, being the pivoting pin 134. In some embodiments, upon pivoting of the cutting tooth 130 about pivoting pin 134, the reaming end 202 of the cutting tooth 130 now engages the bone 500 of the patient and thus widens the diameter of the initial bore 510 to an undercut bore 520 during proximal advancement of the drilling device 100. In some embodiments, the undercut bore 520 has a diameter of 6 mm in this particular example.

According to some exemplary embodiments, the pivoting axis 134 is disposed closer to the drilling end 200 than to the reaming end 202, thus, optionally, the reaming end of the cutting tooth is longer than the drilling end 200, thereby allowing effective engagement of the reaming end 202 with the initial bore 510.

According to some exemplary embodiments, upon pivoting of the cutting tooth about pivoting axis 134, the cutting tooth 130 extends radially from the outer perimeter of the shaft element 102. In some embodiments, the drilling end 200 of the cutting tooth 130 extends radially through cut-out 250 of the shaft element 102 and the reaming end 202 simultaneously extends radially through cut-out 252 of the shaft element 102.

In some embodiments, the fact that the cutting tooth 130 is the most distal component of the drilling device 600 allows for example, accurate forming of the undercut bore 520.

In some embodiments, all other spatial relationships between the different components of the drilling device 600 remain substantially the same as described for example, with reference to FIGS. 27A-27C.

Reference is now made to FIGS. 29A-29C, which are respective two different plan views and a sectional view illustration of a drilling device, for example the drilling device 600 of FIGS. 19A & 19B shown in a second partially open operative orientation inserted into the bone 500 of the patient, sectional view is taken along lines B-B in FIG. 29B, and according to some exemplary embodiments of the invention.

According to some exemplary embodiments, for example as seen in FIGS. 29A-29C, the drilling device 600 is in a second partially open operative orientation, where the cutting tooth 130 more radially extends from the outer surface of the shaft element 102 and is optionally adapted in this orientation for reaming an undercut bore having a diameter of 8-10 mm, for example 8.5 mm, 9 mm, 9.5 mm or any intermediate, smaller or larger diameter or range of diameters, within the bone 500 of the patient, using the reaming end 202, while optionally advancing the drilling device 600 rearwardly in a proximal direction through bone 500 of the patient.

According to some exemplary embodiments, rotation of the adjusting element 670, and in turn of the cam connector 662 urge optionally axial displacement of the pusher element 110, which in turn causes radial extension of the cutting tooth 130 with respect to shaft element 102. In some embodiments, the extent of the radial extension of the cutting tooth is defined by the extent of rotation of the adjusting element 670. In some embodiments, in this particular operative orientation, the diameter of the undercut bore 530 is set for 9 mm. In some embodiments, any other suitable diameter for the undercut bore can be formed using drilling device 600 in the second partially open operative orientation.

In some embodiments, for example as seen in FIG. 29A, an alignment between mark that may be formed on the cover element 640 with the scale markings 672 on the adjusting element 670 indicate to the user what diameter is currently adjusted.

In some embodiments, for example as seen in FIG. 29A, the distal hub portion 700 of the cam connector 662 is less proximally spaced from the distal hub portion 740 of the retainer 660 as compared to FIG. 28A.

According to some exemplary embodiments, for example as seen in FIG. 29C, the pin 674 is further displaced along cam tunnel 800 away from the first end 801 thereof as compared to FIG. 28C. Optionally, due to fixed connection between pin 674 and cam connector 662, following further displacement of pin 674 along the cam tunnel 800, the cam connector 662 is further displaced distally, thereby optionally urging further distal displacement of the pusher element 110, axially displaces and pivots the crank 120 and thus further opening of the cutting tooth 130 to the diameter set by the user.

According to some exemplary embodiments, the adjusting element 670 is held in a certain orientation by means of leaf springs 680 that are optionally seated within one of the recesses 803 of the adjusting element 670 and thus optionally prevent inadvertent rotation thereof.

According to some exemplary embodiments, upon distal displacement of the pusher element 110, the crank 120 is pivoted about pin 122, and the cutting tooth 130 is optionally in turn pivoted about its pivoting axis, being the pivoting pin 134. In some embodiments, upon pivoting of the cutting tooth 130 about pivoting pin 134, the reaming end 202 of the cutting tooth 130 now engages the bone 500 of the patient and thus further widens the diameter of the initial bore 510 to an undercut bore 530 during proximal advancement of the drilling device 100. In some embodiments, the undercut bore 530 has a diameter in a range of 8-10 mm, for example 8 mm, 8.5 mm, 9 mm or any intermediate, smaller or larger diameter or range of diameters. In some embodiments, the pivoting axis 134 is disposed closer to the drilling end 200 than to the reaming end 202, thus for example, the reaming end of the cutting tooth is longer than the drilling end 200, thereby optionally allowing effective engagement of the reaming end 202 with the initial bore 510.

According to some exemplary embodiments, upon pivoting of the cutting tooth about pivoting axis 134, the cutting tooth 130 extends radially from the outer perimeter of the shaft element 102. In some embodiments, the drilling end 200 of the cutting tooth 130 extends radially through cut-out 250 of the shaft element 102 and the reaming end 202 simultaneously extends radially through cut-out 252 of the shaft element 102.

In some embodiments, the cutting tooth 130 is the most distal component of the drilling device 100, which optionally allows for accurate forming of the undercut bore 530.

In some embodiments, all other spatial relationships between the different components of the drilling device 600 remain substantially the same as described, for example, with reference to FIGS. 28A-28C.

Reference is now made to FIGS. 30A-30C, which are respective two different plan views and a sectional view illustration of a drilling device, for example the drilling device 600 of FIGS. 19A & 19B shown in a fully open operative orientation inserted into the bone 500 of the patient, sectional view is taken along lines B-B in FIG. 30B, and according to some exemplary embodiments of the invention.

According to some exemplary embodiments, for example as seen in FIGS. 30A-30C, the drilling device 600 is in a fully open operative orientation, where optionally the cutting tooth 130 even more radially extends from the outer surface of the shaft element 102 and is adapted in this orientation for reaming an undercut bore having a diameter in a range of 10-14 mm, for example 11 mm, 12 mm, 12.5 or any intermediate, smaller or larger diameter or range of diameters, within the bone 500 of the patient, using, for example, the reaming end 202, while optionally advancing the drilling device 600 rearwardly in a proximal direction through bone 500 of the patient.

According to some exemplary embodiments, rotation of the adjusting element 670, and in turn of the cam connector 662 urge axial displacement of the pusher element 110, axially displaces and pivots the crank 120, which in turn optionally causes radial extension of the cutting tooth 130 with respect to shaft element 102. In some embodiments, the extent of the radial extension of the cutting tooth is defined by the extent of rotation of the adjusting element 670. In some embodiments, and in this particular operative orientation, the diameter of the undercut bore 540 is set for 12 mm. In some embodiments, it is noted that any other suitable diameter for the undercut bore can be formed using drilling device 600 in the fully open operative orientation. In some embodiments, in this fully open operative orientation, the cutting tooth 130 extends transversely with respect to longitudinal axis 107.

In some embodiments, for example as seen in FIG. 30A, an alignment between mark that may be formed on the cover element 640 with the scale markings 672 on the adjusting element 670 indicate to the user what diameter is currently adjusted.

In some embodiments, for example as seen in FIG. 30A, the distal hub portion 700 of the cam connector 662 is further distally displaced and is now disposed adjacent to the distal hub portion 740 of the retainer 660, for example as compared to FIG. 29A.

In some embodiments, for example as seen in FIG. 30C, the pin 674 is further displaced along cam tunnel 800 away from the first end 801 thereof, for example as compared to FIG. 29C and is now disposed adjacent to the second end 802. Optionally, due to fixed connection between pin 674 and cam connector 662, following further displacement of pin 674 along the cam tunnel 800, the cam connector 662 is further displaced distally, thereby, optionally, urging further distal displacement of the pusher element 110, axially displaces and pivots the crank 120, and thus optionally further opening of the cutting tooth 130 to the diameter set by the user.

In some embodiments, the adjusting element 670 is held in a certain orientation by means of leaf springs 680 that are optionally seated within one of the recesses 803 of the adjusting element 670 and thus prevent inadvertent rotation thereof.

According to some exemplary embodiments, upon distal displacement of the pusher element 110, the crank 120 is pivoted about pin 122, and the cutting tooth 130 is in turn pivoted about its pivoting axis, being the pivoting pin 134. In some embodiments, upon pivoting of the cutting tooth 130 about pivoting pin 134, the reaming end 202 of the cutting tooth 130 now engages the bone 500 of the patient and thus, optionally, widens the diameter of the initial bore 510 to an undercut bore 540 during proximal advancement of the drilling device 600. The undercut bore 540 has a diameter of 12 mm in this particular example and in some embodiments of the invention.

In some embodiments, the pivoting axis 134 is disposed closer to the drilling end 200 than to the reaming end 202, thus optionally the reaming end of the cutting tooth is longer than the drilling end 200, thereby, for example, allowing effective engagement of the reaming end 202 with the initial bore 510.

In some embodiments, upon pivoting of the cutting tooth about pivoting axis 134, the cutting tooth 130 extends radially from the outer perimeter of the shaft element 102. In some embodiments, the drilling end 200 of the cutting tooth 130 extends radially through cut-out 250 of the shaft element 102 and the reaming end 202 simultaneously extends radially through cut-out 252 of the shaft element 102.

In some embodiments, the cutting tooth 130 is the most distal component of the drilling device 100 which allows, for example, accurate forming of the undercut bore 540.

In some embodiments, all other spatial relationships between the different components of the drilling device 600 remain substantially the same as described for example with reference to FIGS. 29A-29C.

Reference is now made to FIGS. 31A-31C, which are respective two different plan views and a sectional view illustration of a drilling device, for example the drilling device 600 of FIGS. 19A & 19B shown in a closed operative orientation before removal from the bone 500 of the patient, sectional view is taken along lines B-B in FIG. 31B, and according to some exemplary embodiments of the invention.

According to some exemplary embodiments, for example as seen in FIGS. 31A-31C, the drilling device 600 is in a fully closed operative orientation, where the cutting tooth 130 does not radially extend from the outer surface of the shaft element 102, adapted for withdrawal of the drilling device 600 from the bone 500 of the patient, while retracting the drilling device 600 proximally. FIGS. 31A-31C show the drilling device 600 before retraction from the bone 500 of the patient.

In some embodiments, rotation of the adjusting element 670, and in turn of the cam connector 662 urge axial displacement of the pusher element 110 proximally, which optionally in turn causes radial retraction of the cutting tooth 130 with respect to shaft element 102.

In some embodiments, for example as seen in FIG. 30A, an alignment between mark that may be formed on the cover element 640 with the scale markings 672 on the adjusting element 670 indicate to the user what diameter is currently adjusted.

In some embodiments, for example as seen in FIG. 31C the pin 674 is now disposed adjacent the first end 801 of the cam tunnel 800, thereby optionally urging proximal displacement of the pusher element 110 and thus closing of the cutting tooth 130.

In some embodiments, the adjusting element 670 is held in a certain orientation by means of leaf springs 680 that are optionally seated within one of the recesses 803 of the adjusting element 670 and thus prevent inadvertent rotation thereof.

Reference is now made to FIGS. 32A-32C, which are respective two different plan views and a sectional view illustration of a drilling device, for example the drilling device 600 of FIGS. 19A & 19B shown in a closed operative orientation following removal from the bone 500 of the patient, sectional view is taken along lines B-B in FIG. 32B, and according to some exemplary embodiments of the invention.

According to some exemplary embodiments, for example as seen in FIGS. 32A-32C, the drilling device 600 is in a fully closed operative orientation, where the cutting tooth 130 does not radially extend from the outer surface of the shaft element 102. FIGS. 32A-32C show the drilling device 100 following retraction from the bone 500 of the patient, whereas the resulting initial bore 510 and undercut bore 520/530/540 are clearly seen, as formed within bone 500 of the patient.

It will be appreciated by persons skilled in the art that the present invention is not limited by what has been particularly shown and described hereinabove. Rather the scope of the present invention includes both combinations and subcombinations of various features described hereinabove as well as variations and modifications thereof which are not in the prior art.

As used herein with reference to quantity or value, the term "about" means "within ±20% of".

The terms "comprises", "comprising", "includes", "including", "has", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular forms "a", "an" and "the" include plural references unless the context clearly dictates otherwise. For example, the term "a compound" or "at least one compound" may include a plurality of compounds, including mixtures thereof throughout this application, embodiments of this invention may be presented with reference to a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as "from 1 to 6" should be considered to have specifically disclosed subranges such as "from 1 to 3", "from 1 to 4", "from 1 to 5", "from 2 to 4", "from 2 to 6", "from 3 to 6", etc.; as well as individual numbers within that range, for example, 1, 2, 3, 4, 5, and 6. This applies regardless of the breadth of the range.

Whenever a numerical range is indicated herein (for example "10-15", "10 to 15", or any pair of numbers linked by these another such range indication), it is meant to include any number (fractional or integral) within the indicated range limits, including the range limits, unless the context clearly dictates otherwise. The phrases "range/ranging/ranges between" a first indicate number and a second indicate number and "range/ranging/ranges from" a first indicate number "to", "up to", "until" or "through" (or another such range-indicating term) a second indicate number are used herein interchangeably and are meant to include the first and second indicated numbers and all the fractional and integral numbers therebetween.

Unless otherwise indicated, numbers used herein and any number ranges based thereon are approximations within the accuracy of reasonable measurement and rounding errors as understood by persons skilled in the art As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting. In addition, any priority document(s) of this application is/are hereby incorporated herein by reference in its/their entirety.

What is claimed is:

1. A bone removal device, comprising:
   an outer elongated shaft having a longitudinal axis, a distal end and a proximal end;
   a bone borer having a distal drilling tip configured to drill into a bone tissue and at least one proximal reamer, wherein said bone borer is movably coupled to the distal end of said outer elongated shaft, wherein said bone borer is configured to move between a drilling state, in which said drilling tip is placed in contact with bone tissue, and reaming states, in which said at least one proximal reamer is placed in contact with the bone tissue; and
   a rotatable adjuster configured to rotate between two or more predetermined stopping states each defining a different tilting angle of said bone borer relative to said longitudinal axis of said outer elongated shaft, wherein said rotation of said rotatable adjuster between said two or more predetermined stopping states is associated with a corresponding axial movement of said rotatable adjuster relative to said outer elongated shaft longitudinal axis;
   wherein said rotatable adjuster comprises a plurality of indentations, each of said plurality of indentations corresponds to a single said stopping state, and said device comprises at least one elastic element configured to engage said plurality of indentations.

2. A device according to claim 1, comprising a pusher element mechanically coupled to said outer elongated shaft and to said bone borer, wherein said pusher element is configured to tilt said bone borer relative to said longitudinal axis of said outer elongated shaft so as to provide said distal drilling tip in a forwardly facing position during said drilling state, and said at least one reamer in a radially extending position during said reaming states.

3. A device according to claim 2, wherein said rotatable adjuster is coupled to said pusher element, wherein said two or more predetermined stopping states each defines a different tilting angle of said bone borer relative to said longitudinal axis of said outer elongated shaft.

4. A device according to claim 1, wherein said bone borer is configured to rotate around a rotation axis that is coaxial with said outer elongated shaft longitudinal axis.

5. A device according to claim 1, wherein said rotatable adjuster is a disc-shaped adjuster, and wherein said plurality of indentations are located on at least one side wall of said disc-shaped adjuster.

6. A device according to claim 2, comprising a crank having a longitudinal axis, a distal end with at least two spaced-apart distal protrusions shaped and sized to be pivotally connectable to said bone borer, and a proximal end with at least two spaced apart proximal protrusions shaped and sized to be pivotally connectable to said pusher element.

7. A device according to claim 6, wherein said two distal protrusions are angled relative to said longitudinal axis of said crank.

8. A device according to claim 1, wherein said outer elongated shaft has an opening crossing side to side through said outer elongated shaft and said bone borer is at least partly within said opening, and wherein in each of said reaming states said opening is closed more than in said drilling state.

9. A device according to claim 8, wherein said opening is shaped and sized to allow bone fragments to move from one side of said outer elongated shaft to an opposite side of said outer elongated shaft through said opening during reaming.

10. A device according to claim 8, wherein said bone borer comprises one or more curved reaming edges, at a proximal end of said bone borer, configured to contact a bone tissue surface when said bone borer is in one of said reaming states.

11. A device according to claim 10, wherein said reamer comprises two or more bone cutting edges, each of said two or more bone cutting edges is positioned on an opposite side wall of said proximal end.

12. A device according to claim 11, wherein at least some of said two or more bone cutting edges converge to a single location.

13. A bone removal kit, comprising the bone removal device according to claim 1, wherein said outer elongated shaft is removable, said bone removal device including at least one reversibly coupling connector coupled to said outer elongated shaft and/or to said rotatable adjuster; wherein said proximal end of said outer elongated shaft is removably coupled to said rotatable adjuster by said at least one reversibly coupling connector.

14. A kit according to claim 13, wherein said outer elongated shaft comprises a pusher element coupled to said bone borer, wherein said pusher element is configured to be removably coupled to said rotatable adjuster.

15. A device according to claim 8, wherein in said drilling state said bone borer closes at least 90% of said opening in said outer elongated shaft.

16. A device according to claim 8, wherein in each of said reaming states said bone borer defines a window of at least 10% of said opening.

17. A device according to claim 1 wherein, in said drilling state, said proximal reamer is located proximal to said shaft distal end.

18. A device according to claim 1, wherein said at least one proximal reamer is configured to move between said drilling state and said reaming states by pivoting about a pivot element attached to said distal end of said outer elongated shaft.

19. A device according to claim 2, wherein said rotatable adjuster is coupled to said pusher element and wherein said axial movement of said rotatable adjuster causes a corresponding axial movement of said pusher element.

* * * * *